(12) United States Patent
Cetti et al.

(10) Patent No.: US 11,334,694 B2
(45) Date of Patent: *May 17, 2022

(54) PERSONAL CARE COMPOSITIONS COMPRISING MALODOR REDUCTION COMPOSITIONS

(71) Applicant: The Procter & Gamble Company, Cincinnati, OH (US)

(72) Inventors: Jonathan Robert Cetti, Mason, OH (US); Gayle Marie Frankenbach, Cincinnati, OH (US); Steven Anthony Horenziak, Cincinnati, OH (US); Judith Ann Hollingshead, Batavia, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 171 days.

This patent is subject to a terminal disclaimer.

(21) Appl. No.: 14/865,257

(22) Filed: Sep. 25, 2015

(65) Prior Publication Data

US 2016/0089318 A1    Mar. 31, 2016

Related U.S. Application Data

(60) Provisional application No. 62/143,862, filed on Apr. 7, 2015, provisional application No. 62/055,844, filed on Sep. 26, 2014.

(51) Int. Cl.
*A61Q 19/00* (2006.01)
*C11B 9/00* (2006.01)
(Continued)

(52) U.S. Cl.
CPC ............... *G06F 30/23* (2020.01); *A61K 8/11* (2013.01); *A61K 8/31* (2013.01); *A61K 8/33* (2013.01); *A61K 8/34* (2013.01); *A61K 8/342* (2013.01); *A61K 8/35* (2013.01); *A61K 8/36* (2013.01); *A61K 8/361* (2013.01); *A61K 8/368* (2013.01); *A61K 8/37* (2013.01); *A61K 8/494* (2013.01); *A61K 8/498* (2013.01); *A61K 8/4926* (2013.01); *A61K 8/4966* (2013.01); *A61K 8/4973* (2013.01); *A61K 8/58* (2013.01); *A61K 8/731* (2013.01); *A61K 8/8152* (2013.01); *A61L 2/18* (2013.01); *A61L 9/01* (2013.01); *A61L 9/012* (2013.01); *A61L 9/03* (2013.01); *A61L 9/122* (2013.01); *A61L 9/127* (2013.01); *A61L 15/20* (2013.01); *A61L 15/28* (2013.01); *A61L 15/46* (2013.01); *A61Q 5/02* (2013.01); *A61Q 13/00* (2013.01); *A61Q 15/00* (2013.01); *A61Q 19/00* (2013.01); *A61Q 19/10* (2013.01); *B01J 20/24* (2013.01); *C08K 5/0008* (2013.01); *C11B 9/003* (2013.01); *C11B 9/008* (2013.01); *C11B 9/0015* (2013.01); *C11B 9/0019* (2013.01);
(Continued)

(58) Field of Classification Search
CPC ... A61K 8/11; A61K 8/31; A61K 8/33; A61K 8/34; A61K 8/342; A61K 8/35; A61K 8/36; A61K 8/361; A61K 8/368; A61K 8/37; A61K 8/4926; A61K 2800/56; A61K 2800/592; A61K 2800/5922; A61Q 5/02; A61Q 13/00; A61Q 15/00; A61Q 19/00; A61Q 19/10; B01J 20/24; C08K 5/0008; C11D 3/001; C11D 3/0068; C11D 3/184; C11D 3/2034; C11D 3/2068; C11D 3/2072; C11D 3/2079; C11D 3/2093; C11D 3/2096; C11D 3/222; C11D 3/30; C11D 3/43; C11D 3/50; C11D 3/505; C11D 11/0017; C11D 17/0043; C11D 17/042; C11D 17/047; C11D 17/06; D06B 1/02; A61L 2209/21; A61L 2300/62; A61L 9/122; A61L 9/127; A61L 15/20; A61L 15/28; A61L 15/46
See application file for complete search history.

(56) References Cited

U.S. PATENT DOCUMENTS 2,438,091 A   3/1948  Lynch
2,528,378 A  10/1950  Mannheimer
(Continued)

FOREIGN PATENT DOCUMENTS

BE    825146 A1   8/1975
CA   1164347 A    3/1984
(Continued)

OTHER PUBLICATIONS

McGinley et al. Performance Verification of Air Freshener Products and Other Odour Control Devices for Indoor Air Quality Malodours. Presented at The 8th Workshop on Odour and Emissions of Plastic Materials Universitat Kassel Institut fur Werkstofftechnik Kassel, Germany: Mar. 27-28, 2006. 13p.*
ASTM D3954-94, Reapproved 2010, vol. 15.04, Standard Test Method for Dropping Point of Waxes.
Todd, C., et al., Volatile silicone fluids for cosmetic formulations, Cosmetics and Toiletries, Jan. 1976, pp. 29-32, vol. 91.
Crepaldi, E.L., et al., Chemical, Structural, and Thermal Properties of Zn(II)-Cr(III) Layered Double Hydroxides Intercalated with Sulfated and Sulfonated Surfactants, Journal of Colloid and Interface Science, 2002, pp. 429-442, vol. 248.
(Continued)

*Primary Examiner* — Robert A Wax
*Assistant Examiner* — Olga V. Tcherkasskaya
(74) *Attorney, Agent, or Firm* — Kathleen Y. Carter; Carrie A. Morgan

(57) ABSTRACT

The present invention relates to personal care compositions comprising malodor reduction compositions and methods of making and using such personal care compositions. Such personal care compositions comprising the malodor control technologies disclosed herein provide malodor control without leaving an undesirable scent and when perfume is used to scent such compositions, such scent is not unduly altered by the malodor control technology.

4 Claims, No Drawings

(51) Int. Cl.

| | |
|---|---|
| *A61K 8/33* | (2006.01) |
| *A61K 8/35* | (2006.01) |
| *A61K 8/36* | (2006.01) |
| *A61K 8/37* | (2006.01) |
| *A61K 8/49* | (2006.01) |
| *A61K 8/58* | (2006.01) |
| *A61Q 15/00* | (2006.01) |
| *A61K 8/31* | (2006.01) |
| *A61K 8/34* | (2006.01) |
| *A61Q 5/02* | (2006.01) |
| *A61Q 19/10* | (2006.01) |
| *A61L 2/18* | (2006.01) |
| *A61L 9/03* | (2006.01) |
| *A61L 9/12* | (2006.01) |
| *D06B 1/02* | (2006.01) |
| *G06F 30/23* | (2020.01) |
| *G16C 10/00* | (2019.01) |
| *G16C 20/40* | (2019.01) |
| *A61L 9/01* | (2006.01) |
| *C08K 5/00* | (2006.01) |
| *A61L 9/012* | (2006.01) |
| *C11D 3/00* | (2006.01) |
| *C11D 3/18* | (2006.01) |
| *C11D 3/20* | (2006.01) |
| *C11D 3/43* | (2006.01) |
| *C11D 17/04* | (2006.01) |
| *C11D 3/22* | (2006.01) |
| *C11D 3/30* | (2006.01) |
| *C11D 3/50* | (2006.01) |
| *C11D 17/06* | (2006.01) |
| *A61K 8/368* | (2006.01) |
| *G06F 17/10* | (2006.01) |
| *G06Q 99/00* | (2006.01) |
| *A61Q 13/00* | (2006.01) |
| *C11D 11/00* | (2006.01) |
| *A61L 15/20* | (2006.01) |
| *A61L 15/28* | (2006.01) |
| *A61L 15/46* | (2006.01) |
| *B01J 20/24* | (2006.01) |
| *C11D 17/00* | (2006.01) |
| *G06F 17/11* | (2006.01) |
| *A61K 8/11* | (2006.01) |
| *A61K 8/73* | (2006.01) |
| *A61K 8/81* | (2006.01) |

(52) U.S. Cl.
CPC .......... *C11B 9/0034* (2013.01); *C11B 9/0038* (2013.01); *C11B 9/0042* (2013.01); *C11B 9/0049* (2013.01); *C11B 9/0053* (2013.01); *C11B 9/0061* (2013.01); *C11B 9/0076* (2013.01); *C11B 9/0092* (2013.01); *C11D 3/001* (2013.01); *C11D 3/0068* (2013.01); *C11D 3/184* (2013.01); *C11D 3/2034* (2013.01); *C11D 3/2068* (2013.01); *C11D 3/2072* (2013.01); *C11D 3/2079* (2013.01); *C11D 3/2093* (2013.01); *C11D 3/2096* (2013.01); *C11D 3/222* (2013.01); *C11D 3/30* (2013.01); *C11D 3/43* (2013.01); *C11D 3/50* (2013.01); *C11D 3/505* (2013.01); *C11D 11/0017* (2013.01); *C11D 17/0043* (2013.01); *C11D 17/042* (2013.01); *C11D 17/047* (2013.01); *C11D 17/06* (2013.01); *D06B 1/02* (2013.01); *G06F 17/10* (2013.01); *G06F 17/11* (2013.01); *G06Q 99/00* (2013.01); *G16C 10/00* (2019.02); *G16C 20/40* (2019.02); *A61K 2800/56* (2013.01); *A61K 2800/592* (2013.01); *A61K 2800/5922* (2013.01); *A61L 2209/21* (2013.01); *A61L 2300/62* (2013.01)

(56) References Cited

U.S. PATENT DOCUMENTS

| | | |
|---|---|---|
| 2,658,072 A | 11/1953 | Kosmin |
| 2,809,971 A | 10/1957 | Bernstein et al. |
| 3,236,733 A | 2/1966 | Karsten et al. |
| 3,753,196 A | 8/1973 | Kurtz et al. |
| 3,761,418 A | 9/1973 | Parran, Jr. |
| 3,792,068 A | 2/1974 | Luedders et al. |
| 3,887,692 A | 6/1975 | Gilman |
| 3,904,741 A | 9/1975 | Jones et al. |
| 4,049,792 A | 9/1977 | Elsnau |
| 4,120,948 A | 10/1978 | Shelton |
| 4,137,180 A | 1/1979 | Naik et al. |
| 4,237,155 A | 12/1980 | Kardouche |
| 4,323,683 A | 4/1982 | Bolich, Jr. et al. |
| 4,345,080 A | 8/1982 | Bolich, Jr. |
| 4,359,456 A | 11/1982 | Gosling et al. |
| 4,379,753 A | 4/1983 | Bolich, Jr. |
| 4,430,243 A | 2/1984 | Bragg |
| 4,470,982 A | 9/1984 | Winkler |
| 4,985,238 A | 1/1991 | Tanner et al. |
| 5,019,375 A | 5/1991 | Tanner et al. |
| 5,104,646 A | 4/1992 | Bolich, Jr. et al. |
| 5,106,609 A | 4/1992 | Bolich, Jr. et al. |
| 5,296,622 A | 3/1994 | Uphues et al. |
| 5,374,614 A | 12/1994 | Behan et al. |
| 5,429,816 A | 7/1995 | Hofrichter et al. |
| 5,486,303 A | 1/1996 | Capeci et al. |
| 5,489,392 A | 2/1996 | Capeci et al. |
| 5,516,448 A | 5/1996 | Capeci et al. |
| 5,565,422 A | 10/1996 | Del Greco et al. |
| 5,569,645 A | 10/1996 | Dinniwell et al. |
| 5,574,005 A | 11/1996 | Welch et al. |
| 5,576,282 A | 11/1996 | Miracle et al. |
| 5,595,967 A | 1/1997 | Miracle et al. |
| 5,597,936 A | 1/1997 | Perkins et al. |
| 5,691,297 A | 11/1997 | Nassano et al. |
| 5,714,137 A | 2/1998 | Trinh et al. |
| 5,879,584 A | 3/1999 | Bianchetti et al. |
| 5,891,424 A | 4/1999 | Bretzler et al. |
| 5,942,217 A | 8/1999 | Woo et al. |
| 5,976,514 A | 11/1999 | Guskey et al. |
| 6,180,121 B1 | 1/2001 | Gucnin et al. |
| 6,225,464 B1 | 5/2001 | Hiler, II et al. |
| 6,248,135 B1 | 6/2001 | Trinh et al. |
| 6,386,392 B1 | 5/2002 | Argentieri et al. |
| 6,413,920 B1 | 7/2002 | Bettiol et al. |
| 6,436,442 B1 | 8/2002 | Woo et al. |
| 6,488,943 B1 | 12/2002 | Beerse et al. |
| 6,656,923 B1 | 12/2003 | Trinh et al. |
| 6,716,805 B1 | 4/2004 | Sherry et al. |
| 6,794,356 B2 * | 9/2004 | Turner ............... C11D 1/62 510/516 |
| 6,814,088 B2 | 11/2004 | Barnabas et al. |
| 6,869,923 B1 | 3/2005 | Cunningham et al. |
| 7,172,099 B2 | 2/2007 | Höfte et al. |
| 7,202,198 B2 | 4/2007 | Gordon et al. |
| 7,223,361 B2 | 5/2007 | Kvietok et al. |
| 8,322,631 B2 | 12/2012 | Richardson et al. |
| 8,609,600 B2 * | 12/2013 | Warr ............... A61K 8/0237 424/401 |
| 8,709,337 B2 | 4/2014 | Gruenbacher et al. |
| 8,772,354 B2 | 7/2014 | Williams et al. |
| 8,931,711 B2 | 1/2015 | Gruenbacher et al. |
| 2003/0008787 A1 | 1/2003 | Mcgee et al. |
| 2004/0151793 A1 | 8/2004 | Paspaleeva-Kuhn et al. |
| 2005/0003980 A1 | 1/2005 | Baker et al. |
| 2005/0276831 A1 | 12/2005 | Dihora et al. |
| 2007/0003499 A1 | 1/2007 | Shen et al. |
| 2007/0020263 A1 | 1/2007 | Shitara et al. |
| 2007/0275866 A1 | 11/2007 | Dykstra |
| 2008/0003245 A1 | 1/2008 | Kroepke et al. |

(56) References Cited

U.S. PATENT DOCUMENTS

| | | | |
|---|---|---|---|
| 2008/0176780 A1* | 7/2008 | Warr | A61K 8/0237 510/103 |
| 2010/0009285 A1 | 1/2010 | Daems et al. | |
| 2010/0061946 A1 | 3/2010 | Schemer et al. | |
| 2010/0287710 A1 | 11/2010 | Denutte et al. | |
| 2010/0322878 A1 | 12/2010 | Stella et al. | |
| 2011/0098209 A1* | 4/2011 | Smets | B01J 13/02 510/405 |
| 2011/0245134 A1* | 10/2011 | Smets | C11D 3/373 510/375 |
| 2011/0303766 A1 | 12/2011 | Smith | |
| 2012/0004328 A1 | 1/2012 | Huchel et al. | |
| 2012/0009285 A1 | 1/2012 | Wei et al. | |
| 2012/0129924 A1 | 5/2012 | Park et al. | |
| 2012/0219610 A1 | 8/2012 | Smith, III et al. | |
| 2012/0237469 A1* | 9/2012 | Dente | A61L 9/01 424/76.1 |
| 2012/0246851 A1 | 10/2012 | Smith, III et al. | |
| 2012/0258150 A1 | 10/2012 | Rauckhorst et al. | |
| 2013/0043145 A1 | 2/2013 | Smith, III et al. | |
| 2013/0043146 A1 | 2/2013 | Smith, III et al. | |
| 2013/0043147 A1 | 2/2013 | Smith, III et al. | |
| 2013/0319463 A1 | 12/2013 | Policicchio | |
| 2014/0201927 A1 | 7/2014 | Bianchetti et al. | |
| 2015/0108163 A1 | 4/2015 | Smith et al. | |
| 2017/0249408 A1 | 8/2017 | Cetti et al. | |

FOREIGN PATENT DOCUMENTS

| | | |
|---|---|---|
| DE | 10 2004 023720 A1 | 12/2005 |
| DE | 10 2007 019369 A1 | 10/2008 |
| EP | 2 005 939 | 12/2008 |
| GB | 1347950 A | 2/1974 |
| GB | 2048229 A | 12/1980 |
| GB | 2144992 A | 3/1985 |
| GB | 2 450 727 A | 1/2009 |
| WO | WO 96/04937 | 2/1996 |
| WO | WO 00/32601 A2 | 6/2000 |
| WO | 2006043177 A1 | 4/2006 |
| WO | WO 2012/136651 | 10/2012 |

OTHER PUBLICATIONS

Morioka, H., et al., Effects of Zinc on the New Preparation Method of Hydroxy Double Salts, Inorganic Chemistry, 1999, pp. 4211-4216, vol. 38, No. 19.
Database WPI; Week 201459; Thomson scientific, London, GB; AN 2014-P66521; XP002752638.
International Search Report; International Application No. PCT/US2015/052088; dated Jan. 22, 2016; 16 pages.
International Search Report; International Application No. PCT/US2015/052090; dated Jan. 19, 2016; 13 pages.
International Search Report; International Application No. PCT/US2015/052092; dated Jan. 12, 2016; 13 pages.
International Search Report; International Application No. PCT/US2015/052219; dated Jan. 26, 2016; 13 pages.
International Search Report; International Application No. PCT/US2015/052093; dated Jan. 12, 2016; 13 pages.
International Search Report; International Application No. PCT/US2015/052094; dated Jan. 20, 2016; 11 pages.
International Search Report; International Application No. PCT/US2015/052119; dated Jan. 20, 2016; 13 pages.
International Search Report; International Application No. PCT/US2015/052225; dated Jan. 20, 2016; 16 pages.
International Search Report; International Application No. PCT/US2015/052130; dated Jan. 12, 2016; 13 pages.
International Search Report; International Application No. PCT/US2015/052084; dated Jan. 19, 2016; 13 pages.
International Search Report; International Application No. PCT/US2015/052089; dated Feb. 23, 2016; 11 pages.
Sep. 25, 2015 Frankenbach, et al. 13564M Yes.
Sep. 25, 2015 Scavone, et al. 14028 Yes.
Sep. 25, 2015 Hollingshead, et al. 14031 Yes.
Sep. 25, 2015 Frankenbach, et al. 14032 Yes.
Sep. 25, 2015 Frankenbach, et al. 14033 Yes.
Sep. 25, 2015 Cetti, et al. 14034 Yes.
Sep. 25, 2015 Frankenbach, et al. 14036 Yes.
Sep. 25, 2015 Frankenbach, et al. 14037 Yes.
Sep. 25, 2015 Frankenbach, et al. 14038 Yes.
Sep. 25, 2015 Frankenbach, et al. 14039 Yes.
Brattoli et al., Odour Detection Methods: Olfactometry and Chemical Sensors, Sensors 2011, 11, pp. 5290-5322.
All Office Actions; U.S. Appl. No. 15/597,391, filed May 17, 2017.
All Office Actions; U.S. Appl. No. 15/708,205, filed Sep. 19, 2017.

* cited by examiner

PERSONAL CARE COMPOSITIONS COMPRISING MALODOR REDUCTION COMPOSITIONS

FIELD OF THE INVENTION

The present invention relates to personal care compositions comprising malodor reduction compositions and methods of making and using such personal care compositions.

BACKGROUND OF THE INVENTION

Unscented or scented products are desired by consumers as they may be considered more natural and discreet than scented products. Manufacturers of unscented or scented products for controlling malodors rely on malodor reduction ingredients or other technologies (e.g. filters) to reduce malodors. However, effectively controlling malodors, for example, amine-based malodors (e.g. fish and urine), thiol and sulfide-based malodors (e.g. garlic and onion), $C_2$-$C_{12}$ carboxylic acid based malodors (e.g. body and pet odor), indole based malodors (e.g. fecal and bad breath), short chain fatty aldehyde based malodors (e.g. grease) and geosmin based malodors (e.g. mold/mildew) may be difficult, and the time required for a product to noticeably reduce malodors may create consumer doubt as to the product's efficacy on malodors. Often times, manufacturers incorporate scented perfumes to help mask these difficult malodors.

Unfortunately, malodor control technologies typically cover up the malodor with a stronger scent and thus interfere with the scent of the perfumed or unperfumed situs that is treated with the malodor control technology. Thus, limited nature of the current malodor control technologies is extremely constraining. Thus what is needed is a broader palette of malodor control technologies so the perfume community can deliver the desired level of character in a greater number of situations/applications. Surprisingly, Applicants recognized that in addition to blocking a malodor's access to a sensory cell, in order to achieve the desired goal, a malodor control technology must leave such sensor cell open to other molecules, for example scent molecules. Thus, personal care compositions comprising the malodor control technologies disclosed herein provide malodor control without leaving an undesirable scent and, when perfume is used to scent such compositions, such scent is not unduly altered by the malodor control technology.

SUMMARY OF THE INVENTION

The present invention relates to personal care compositions comprising malodor reduction compositions and methods of making and using such personal care compositions. Such personal care compositions comprising the malodor control technologies disclosed herein provide malodor control without leaving an undesirable scent and, when perfume is used to scent such compositions, such scent is not unduly altered by the malodor control technology.

DETAILED DESCRIPTION OF THE INVENTION

Definitions

"Personal care composition" refers to compositions intended for topical application to skin or hair and can be, for example, in the form of a liquid, semi-liquid cream, lotion, gel, or solid. Examples of personal care compositions can include, but are not limited to, bar soaps, shampoos, conditioning shampoos, body washes, moisturizing body washes, shower gels, skin cleansers, cleansing milks, in-shower body moisturizers, pet shampoos, shaving preparations, etc.

"Bar soap" refers to compositions intended for topical application to a surface such as skin or hair to remove, for example, dirt, oil, and the like. The bar soaps can be rinse-off formulations, in which the product is applied topically to the skin or hair and then subsequently rinsed within minutes from the skin or hair with water. The product could also be wiped off using a substrate. Bar soaps can be in the form of a solid (e.g., non-flowing) bar soap intended for topical application to skin. The bar soap can also be in the form of a soft solid which is compliant to the body. The bar soap additionally can be wrapped in a substrate which remains on the bar during use.

"Rinse-off" means the intended product usage includes application to skin and/or hair followed by rinsing and/or wiping the product from the skin and/or hair within a few seconds to minutes of the application step.

"STnS" refers to sodium trideceth(n) sulfate, wherein n can define the average number of moles of ethoxylate per molecule.

"Structured" refers to having a rheology that can confer stability on the personal care composition. A cleansing phase can be considered to be structured if the cleansing phase has one or more following characteristics: (a) Zero Shear Viscosity of at least 100 Pascal-seconds (Pa-s), at least about 200 Pa-s, at least about 500 Pa-s, at least about 1,000 Pa-s, at least about 1,500 Pa-s, or at least about 2,000 Pa-s; (b) A Structured Domain Volume Ratio as measured by the Ultra-centrifugation Method described hereinafter, of greater than about 40%, at least about 45%, at least about 50%, at least about 55%, at least about 60%, at least about 65%, at least about 70%, at least about 75%, at least about 80%, at least about 85%, or at least about 90%; or (c) A Young's Modulus of greater than about 2 Pascals (Pa), greater than about 10 Pa, greater than about 20 Pa, greater than about 30 Pa, greater than about 40 Pa, greater than about 50 Pa, greater than about 75 Pa, or greater than about 100 Pa.

As used herein "MORV" is the calculated malodor reduction value for a subject material. A material's MORV indicates such material's ability to decrease or even eliminate the perception of one or more malodors. For purposes of the present application, a material's MORV is calculated in accordance with method found in the test methods section of the present application.

As used herein, "malodor" refers to compounds generally offensive or unpleasant to most people, such as the complex odors associated with bowel movements.

As used herein, "odor blocking" refers to the ability of a compound to dull the human sense of smell.

As used herein, the term "perfume" does not include malodor reduction materials. Thus, the perfume portion of a composition does not include, when determining the perfume's composition, any malodor reduction materials found in the composition as such malodor reduction materials are described herein. In short, if a material has a malodor reduction value "MORV" that is within the range of the MORV recited in the subject claim, such material is a malodor reduction material for purposes of such claim.

As used herein, the terms "a" and "an" mean "at least one".

As used herein, the terms "include", "includes" and "including" are meant to be non-limiting.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Personal Care Compositions

Rinse-off personal care compositions can come in a variety of forms. For example, a personal care composition can be in a liquid form and can be a body wash, moisturizing body wash, shampoo, conditioning shampoo, shower gel, skin cleansers, cleansing milk, in-shower body moisturizer, pet shampoo, shaving preparation, etc. Rinse-off personal care compositions can also be in a solid form, such as a bar soap or can be in a semi-solid form, like a paste or gel. Solid forms can also be created in many shapes and forms such as a rectangle, or be created in a powder or pellet form, for example. Additionally, solid and semi-solid forms can be combined with a substrate to form an article as described in more detail in U.S. Pre-Grant Publication Nos. 2012/0246851 A1; 2013/0043145 A1; 2013/0043146 A1; and 2013/0043147 A1.

Many personal care compositions can be water-based. However, water can be lost through processes such as evaporation during the process of making a personal care composition, or can be lost to packaging materials or the like after manufacturing. A personal care composition can, therefore, also include materials that bind water inside the composition such that the desired level of water can be maintained in the personal care composition. Examples of such materials can include carbohydrate structurants and humectants such as glycerin. Personal care compositions can also be anhydrous and can be produced or used without any appreciable water content.

Personal care compositions can include perfume materials. Many consumers prefer personal care compositions that can consistently provide a desired scent, or odor, that can be perceived each time the product is used. Perfume materials can provide the desired scent or odor to these personal care compositions. These perfume (i.e., fragrance) materials can include perfumes, perfume raw materials, and perfume delivery systems.

Malodor Reduction Materials

A non-limiting set of suitable malodor reduction materials are provided in the tables below. For ease of use, each material in Tables 1-3 is assigned a numerical identifier which is found in the column for each table that is designated Number. Table 4 is a subset of Table 1, Table 5 is a subset of Table 2 and Table 6 is a subset of Table 3 and therefor Tables 4, 5 and 6 each use the same numerical identifier as found, respectively, in Tables 1-3.

| Codes |
|---|
| A = Vapor Pressure > 0.1 torr |
| B = Vapor Pressure is between 0.01 torr and 0.1 torr |
| C = LogP < 3 |
| D = LogP > 3 |
| E = Probability of Ingredient Color Instability = 0% |
| F = Probability of Ingredient Color Instability < 71% |
| G = Odor Detection Threshold less than p.ol = 8 |
| H = Odor Detection Threshold greater than p.ol = 8 |
| I = Melamine formaldehyde PMC Headspace Response Ratio greater than or equal to 10 |
| J = Melamine formaldehyde PMC leakage less than or equal to 5% |
| K = Log of liquid dish neat product liquid-air partition coefficient greater than or equal to −7 |
| L = Log of liquid dish neat product liquid-air partition coefficient greater than or equal to −5 |

TABLE 1

List of materials with at least one MORV from 1 to 5

| Number | Material Name | CAS Number | Comment Code |
|---|---|---|---|
| 1 | 2-ethylhexyl (Z)-3-(4-methoxyphenyl)acrylate | 5466-77-3 | DEFHJ |
| 2 | 2,4-dimethyl-2-(5,5,8,8-tetramethyl-5,6,7,8-tetrahydronaphthalen-2-yl)-1,3-dioxolane | 131812-67-4 | DFHJ |
| 3 | 1,1-dimethoxynon-2-yne | 13257-44-8 | ACEFHJK |
| 4 | para-Cymen-8-ol | 1197-01-9 | BCGIJK |
| 7 | 3-methoxy-7,7-dimethyl-10-methylenebicyclo[4.3.1]decane | 216970-21-7 | BDEFHJK |
| 9 | Methoxycyclododecane | 2986-54-1 | DEFHJK |
| 10 | 1,1-dimethoxycyclododecane | 950-33-4 | DEFHJK |
| 11 | (Z)-tridec-2-enenitrile | 22629-49-8 | DEFHJK |
| 13 | Oxybenzone | 131-57-7 | DEFGJ |
| 14 | Oxyoctaline formate | 65405-72-3 | DFHJK |
| 16 | 4-methyl-1-oxaspiro[5.5]undecan-4-ol | 57094-40-3 | CFGIJK |
| 17 | 7-methyl-2H-benzo[b][1,4]dioxepin-3(4H)-one | 28940-11-6 | CGIK |
| 18 | 1,8-dioxacycloheptadecan-9-one | 1725-01-5 | DGJ |
| 21 | 4-(tert-pentyl)cyclohexan-1-one | 16587-71-6 | ADFGIJKL |
| 22 | o-Phenyl anisol | 86-26-0 | DEFHJK |
| 23 | 3a,5,6,7,8,8b-hexahydro-2,2,6,6,7,8,8-heptamethyl-4H-indeno(4,5-d)-1,3-dioxole | 823178-41-2 | DEFHJK |
| 25 | 7-isopropyl-8,8-dimethyl-6,10-dioxaspiro[4.5]decane | 62406-73-9 | BDEFHIJK |
| 28 | Octyl 2-furoate | 39251-88-2 | DEFHJK |
| 29 | Octyl acetate | 112-14-1 | BDEFHJKL |
| 30 | octanal propylene glycol acetal | 74094-61-4 | BDEFHJKL |
| 31 | Octanal | 124-13-0 | ACHIKL |
| 32 | Octanal dimethyl acetal | 10022-28-3 | ACEFGJKL |
| 33 | Myrcene | 123-35-3 | ADEFGIKL |
| 34 | Myrcenol | 543-39-5 | BCEFGIJK |
| 35 | Myrcenyl acetate | 1118-39-4 | ADEFGJK |
| 36 | Myristaldehyde | 124-25-4 | DFHJK |
| 37 | Myristicine | 607-91-0 | CGJK |
| 38 | Myristyl nitrile | 629-63-0 | DEFHJK |
| 39 | 2,2,6,8-tetramethyl-1,2,3,4,4a,5,8,8a-octahydronaphthalen-1-ol | 103614-86-4 | DEFHIJK |
| 42 | Ocimenol | 5986-38-9 | BCHIJK |
| 43 | Ocimenol | 28977-58-4 | BCHIJK |
| 47 | Nopyl acetate | 128-51-8 | DEFHJK |
| 48 | Nootkatone | 4674-50-4 | DHJK |
| 49 | Nonyl alcohol | 143-08-8 | BDEFGIJKL |
| 50 | Nonaldehyde | 124-19-6 | ADHIKL |
| 52 | 12-methyl-14-tetradec-9-enolide | 223104-61-8 | DFHJK |
| 57 | N-ethyl-p-menthane-3-carboxamide | 39711-79-0 | DEFGIJK |
| 61 | 1-(3-methylbenzofuran-2-yl)ethan-1-one | 23911-56-0 | CEFHIK |
| 62 | 2-methoxynaphthalene | 93-04-9 | BDEFHK |
| 63 | Nerolidol | 7212-44-4 | DEFHJK |
| 64 | Nerol | 106-25-2 | BCHIK |

TABLE 1-continued

List of materials with at least one MORV from 1 to 5

| Number | Material Name | CAS Number | Comment Code |
|---|---|---|---|
| 65 | 1-ethyl-3-methoxytricyclo[2.2.1.02,6]heptane | 31996-78-8 | ACEFHIJKL |
| 67 | Methyl (E)-non-2-enoate | 111-79-5 | ADEFHJKL |
| 68 | 10-isopropyl-2,7-dimethyl-1-oxaspiro[4.5]deca-3,6-diene | 89079-92-5 | BDEFHIJK |
| 69 | 2-(2-(4-methylcyclohex-3-en-1-yl)propyl)cyclopentan-1-one | 95962-14-4 | DHJK |
| 70 | Myrtenal | 564-94-3 | ACFHIJKL |
| 71 | (E)-4-(2,2,3,6-tetramethylcyclohexyl)but-3-en-2-one | 54992-90-4 | BDEFHIJK |
| 74 | Myraldyl acetate | 53889-39-7 | DHJK |
| 75 | Musk tibetine | 145-39-1 | DHIJ |
| 76 | 1,7-dioxacycloheptadecan-8-one | 3391-83-1 | DGJ |
| 77 | Musk ketone | 81-14-1 | DHJ |
| 78 | Musk ambrette | 83-66-9 | DHIJ |
| 79 | 3-methylcyclopentadecan-1-one | 541-91-3 | DEFHJK |
| 80 | (E)-3-methylcyclopentadec-4-en-1-one | 82356-51-2 | DHJK |
| 82 | 3-methyl-4-phenylbutan-2-ol | 56836-93-2 | BCEFHIK |
| 83 | 1-(4-isopropylcyclohexyl)ethan-1-ol | 63767-86-2 | BDEFHIJK |
| 85 | Milk Lactone | 72881-27-7 | DEFHJK |
| 91 | Methyl octine carbonate | 111-80-8 | BDEFHKL |
| 92 | Methyl octyl acetaldehyde | 19009-56-4 | ADFHJKL |
| 93 | 6,6-dimethoxy-2,5,5-trimethylhex-2-ene | 67674-46-8 | ACHIJKL |
| 98 | Methyl phenylethyl carbinol | 2344-70-9 | BCEFHIK |
| 100 | Methyl stearate | 112-61-8 | DEFHJ |
| 101 | Methyl nonyl acetaldehyde dimethyl acetal | 68141-17-3 | BDEFHJK |
| 102 | Methyl nonyl ketone | 112-12-9 | BDFHJKL |
| 103 | Methyl nonyl acetaldehyde | 110-41-8 | BDFHJK |
| 104 | Methyl myristate | 124-10-7 | DEFHJK |
| 105 | Methyl linoleate | 112-63-0 | DEFHJ |
| 106 | Methyl lavender ketone | 67633-95-8 | CFHJK |
| 108 | Methyl isoeugenol | 93-16-3 | ACEFHK |
| 109 | Methyl hexadecanoate | 112-39-0 | DEFHJK |
| 110 | Methyl eugenol | 93-15-2 | ACEFHK |
| 112 | Methyl epijasmonate | 1211-29-6 | CHJK |
| 113 | Methyl dihydrojasmonate | 24851-98-7 | DFHJK |
| 114 | Methyl diphenyl ether | 3586-14-9 | DEFHJK |
| 117 | Methyl cinnamate | 103-26-4 | BCEFHK |
| 119 | Methyl chavicol | 140-67-0 | ADEFHK |
| 120 | Methyl beta-naphthyl ketone | 93-08-3 | CEFHK |
| 122 | Methyl 2-octynoate | 111-12-6 | ACEFHKL |
| 123 | Methyl alpha-cyclogeranate | 28043-10-9 | ACHIJKL |
| 126 | Methoxycitronellal | 3613-30-7 | ACFGIJK |
| 128 | Menthone 1,2-glycerol ketal (racemic) | 67785-70-0 | CEFHJ |
| 130 | Octahydro-1H-4,7-methanoindene-1-carbaldehyde | 30772-79-3 | BCFHIJKL |
| 134 | 3-(3-(tert-butyl)phenyl)-2-methylpropanal | 62518-65-4 | BDHJK |
| 135 | (E)-4-(4,8-dimethylnona-3,7-dien-1-yl)pyridine | 38462-23-6 | DEFHJK |
| 137 | (E)-trideca-3,12-dienenitrile | 134769-33-8 | DEFHJK |
| 140 | 2,2-dimethyl-3-(m-tolyl)propan-1-ol | 103694-68-4 | CEFHIJK |
| 141 | 2,4-dimethyl-4,4a,5,9b-tetrahydroindeno[1,2-d][1,3]dioxine | 27606-09-3 | CEFHJK |
| 142 | Maceal | 67845-30-1 | BDFHJK |
| 143 | 4-(4-hydroxy-4-methylpentyl)cyclohex-3-ene-1-carbaldehyde | 31906-04-4 | CHJ |
| 145 | l-Limonene | 5989-54-8 | ADEFGIJKL |
| 146 | (Z)-3-hexen-1-yl-2-cyclopenten-1-one | 53253-09-1 | BDHK |
| 148 | Linalyl octanoate | 10024-64-3 | DEFHJ |
| 149 | Linalyl isobutyrate | 78-35-3 | BDHJK |
| 152 | Linalyl benzoate | 126-64-7 | DFHJ |
| 153 | Linalyl anthranilate | 7149-26-0 | DFHJ |
| 155 | Linalool oxide (furanoid) | 60047-17-8 | BCHIJK |
| 156 | linalool oxide | 1365-19-1 | CGIJK |
| 158 | (2Z,6E)-3,7-dimethylnona-2,6-dienenitrile | 61792-11-8 | BDEFHJK |
| 159 | 3-(4-methylcyclohex-3-en-1-yl)butanal | 6784-13-0 | ACFHIJK |
| 161 | (2,5-dimethyl-1,3-dihydroinden-2-yl)methanol | 285977-85-7 | CEFHJK |
| 162 | 3-(4-(tert-butyl)phenyl)-2-methylpropanal | 80-54-6 | BDHJK |
| 167 | (E)-1-(1-methoxypropoxy)hex-3-ene | 97358-54-8 | ACEFGJKL |
| 168 | Leaf acetal | 88683-94-7 | ACEFGJKL |
| 170 | l-Carveol | 2102-58-1 | BCHIJK |
| 174 | Lauryl alcohol | 112-53-8 | DEFGJK |
| 175 | Lauryl acetate | 112-66-3 | DEFHJK |
| 176 | Lauric acid | 143-07-7 | DEFHJ |
| 177 | Lactojasmone | 7011-83-8 | BDEFHIJKL |
| 178 | Lauraldehyde | 112-54-9 | BDFHJK |
| 179 | 3,6-dimethylhexahydrobenzofuran-2(3H)-one | 92015-65-1 | BCEFHIJKL |
| 182 | 4-(1-ethoxyvinyl)-3,3,5,5-tetramethylcyclohexan-1-one | 36306-87-3 | BDFHIJK |
| 183 | Khusimol | 16223-63-5 | CEFHJK |
| 184 | 5-(sec-butyl)-2-(2,4-dimethylcyclohex-3-en-1-yl)-5-methyl-1,3-dioxane | 117933-89-8 | DEFHJ |
| 185 | (1-methyl-2-((1,2,2-trimethylbicyclo[3.1.0]hexan-3-yl)methyl)cyclopropyl)methanol | 198404-98-7 | DEFHJK |
| 186 | 2-propylheptanenitrile | 208041-98-9 | ADEFHIJKL |
| 187 | (E)-6-(pent-3-en-1-yl)tetrahydro-2H-pyran-2-one | 32764-98-0 | BCFHIKL |
| 189 | 2-hexylcyclopentan-1-one | 13074-65-2 | BDFHJKL |
| 190 | 2-methyl-4-phenyl-1,3-dioxolane | 33941-99-0 | BCEFGIK |
| 192 | 2,6,9,10-tetramethyl-1-oxaspiro(4.5)deca-3,6-diene | 71078-31-4 | BDEFHIJK |
| 193 | Isopulegol | 89-79-2 | BCEFHIJKL |
| 195 | Isopropyl palmitate | 142-91-6 | DEFHJ |
| 196 | Isopropyl myristate | 110-27-0 | DEFHJK |
| 197 | Isopropyl dodecanoate | 10233-13-3 | DEFHJK |
| 199 | Isopimpinellin | 482-27-9 | CFGJ |
| 206 | Iso3-methylcyclopentadecan-1-one | 3100-36-5 | DEFGJK |
| 208 | Isomenthone | 491-07-6 | ADEFGIJKL |
| 209 | Isojasmone | 95-41-0 | BDFHJKL |
| 210 | Isomenthone | 36977-92-1 | ADEFGIJKL |
| 211 | Isohexenyl cyclohexenyl carboxaldehyde | 37677-14-8 | DFHJK |
| 212 | Isoeugenyl benzyl ether | 120-11-6 | DFHJ |
| 215 | 1-((2S,3S)-2,3,8,8-tetramethyl-1,2,3,4,5,6,7,8-octahydronaphthalen-2-yl)ethan-1-one | 54464-57-2 | DHJK |
| 218 | Isocyclocitral | 1335-66-6 | ACFHIJKL |
| 221 | Isobutyl quinoline | 65442-31-1 | DEFHJK |
| 227 | Isobornylcyclohexanol | 68877-29-2 | DEFHJK |
| 228 | Isobornyl propionate | 2756-56-1 | BDEFHIJK |
| 229 | Isobornyl isobutyrate | 85586-67-0 | BDEFHIJK |
| 230 | Isobornyl cyclohexanol | 66072-32-0 | DEFHJK |
| 231 | Isobornyl acetate | 125-12-2 | ADEFHIJKL |
| 233 | Isobergamate | 68683-20-5 | DEFHJK |
| 234 | Isoamyl undecylenate | 12262-03-2 | DEFHJK |
| 238 | Isoamyl laurate | 6309-51-9 | DEFHJK |
| 242 | Isoambrettolide | 28645-51-4 | DGJ |
| 243 | Irisnitrile | 29127-83-1 | ADEFHKL |
| 244 | Indolene | 68527-79-7 | DEFHJ |
| 246 | Indol/Hydroxycitronellal Schiff base | 67801-36-9 | DEFHJ |
| 247 | 4,4a,5,9b-tetrahydroindeno[1,2-d][1,3]dioxine | 18096-62-3 | BCEFGJK |
| 249 | Hydroxy-citronellol | 107-74-4 | CEFGIJK |
| 252 | 2-cyclododecylpropan-1-ol | 118562-73-5 | DEFHJK |
| 253 | Hydrocitronitrile | 54089-83-7 | CEFHJK |
| 254 | Hydrocinnamyl alcohol | 122-97-4 | BCEFHIK |
| 256 | Hydratropaldehyde dimethyl acetal | 90-87-9 | ACEFHJK |
| 259 | 5-ethyl-4-hydroxy-2-methylfuran-3(2H)-one | 27538-09-6 | CFGIK |
| 260 | 2,3-dihydro-3,3-dimethyl-1H-indene-5-propanal | 173445-44-8 | DHJK |
| 261 | 3-(3,3-dimethyl-2,3-dihydro-1H-inden-5-yl)propanal | 173445-65-3 | DHJK |

TABLE 1-continued

List of materials with at least one MORV from 1 to 5

| Number | Material Name | CAS Number | Comment Code |
|---|---|---|---|
| 263 | Hexyl octanoate | 1117-55-1 | DEFHJK |
| 267 | Hexyl hexanoate | 6378-65-0 | DEFHJKL |
| 269 | Hexyl cinnamic aldehyde | 101-86-0 | DHJ |
| 271 | Hexyl benzoate | 6789-88-4 | DEFHJK |
| 274 | Hexenyl tiglate | 84060-80-0 | BDEFHJK |
| 276 | (E)-3,7-dimethylocta-2,6-dien-1-yl palmitate | 3681-73-0 | DEFHJ |
| 277 | Hexadecanolide | 109-29-5 | DEFGJK |
| 278 | 2-butyl-4,4,6-trimethyl-1,3-dioxane | 54546-26-8 | ADEFHIJKL |
| 280 | Ethyl (1R,2R,3R,4R)-3-isopropylbicyclo[2.2.1]hept-5-ene-2-carboxylate | 116126-82-0 | BDEFHIJK |
| 281 | 3a,4,5,6,7,7a-hexahydro-1H-4,7-methanoinden-6-yl acetate | 5413-60-5 | CEFGJK |
| 285 | 2-(1-(3,3-dimethylcyclohexyl)ethoxy)-2-methylpropyl propionate | 141773-73-1 | DEFHJ |
| 286 | Heliotropine diethyl acetal | 40527-42-2 | CEFGJ |
| 288 | Helional | 1205-17-0 | CHJK |
| 289 | (E)-oxacyclohexadec-13-en-2-one | 111879-80-2 | DGJK |
| 290 | Gyrane | 24237-00-1 | ADEFHIJKL |
| 292 | Guaiol | 489-86-1 | DEFHJK |
| 293 | 1-(2,6,6-trimethylcyclohex-2-en-1-yl)pentan-3-one | 68611-23-4 | DHJK |
| 294 | Ethyl 2-ethyl-6,6-dimethylcyclohex-2-ene-1-carboxylate | 57934-97-1 | BDEFHIJK |
| 295 | Germacrene B | 15423-57-1 | DEFHJK |
| 296 | Germacrene D | 23986-74-5 | DEFHJK |
| 300 | Geranyl phenylacetate | 102-22-7 | DFHJ |
| 301 | Geranyl phenyl acetate | 71648-43-6 | DFHJ |
| 303 | Geranyl linalool | 1113-21-9 | DFHJ |
| 307 | Geranyl cyclopentanone | 68133-79-9 | DHJK |
| 316 | gamma-Undecalactone (racemic) | 104-67-6 | DEFHJKL |
| 317 | gamma-Terpinyl acetate | 10235-63-9 | BDHJK |
| 318 | gamma-Terpineol | 586-81-2 | BCGIJK |
| 321 | gamma-Nonalactone | 104-61-0 | BCEFHIKL |
| 322 | gamma-Muurolene | 30021-74-0 | DEFHJKL |
| 323 | gamma-(E)-6-(pent-3-en-1-yl)tetrahydro-2H-pyran-2-one | 63095-33-0 | BCEFHKL |
| 324 | gamma-Ionone | 79-76-5 | BDEFHIJK |
| 325 | gamma-Himachalene | 53111-25-4 | BDEFHJKL |
| 328 | gamma-Gurjunene | 22567-17-5 | DEFHJKL |
| 329 | gamma-Eudesmol | 1209-71-8 | DFHJK |
| 330 | gamma-Dodecalactone | 2305-05-7 | DEFHJK |
| 331 | gamma-Damascone | 35087-49-1 | BDEFHJK |
| 332 | gamma-Decalactone | 706-14-9 | BDEFHIJKL |
| 333 | gamma-Cadinene | 39029-41-9 | DEFHJKL |
| 334 | 1-(3,3-dimethylcyclohexyl)pent-4-en-1-one | 56973-87-6 | BDEFHJK |
| 335 | 4,6,6,7,8,8-hexamethyl-1,3,4,6,7,8-hexahydrocyclopenta[g]isochromene | 1222-05-5 | DEFHJK |
| 336 | Furfuryl octanoate | 39252-03-4 | DEFHJK |
| 338 | Furfuryl hexanoate | 39252-02-3 | CEFHJK |
| 339 | Furfuryl heptanoate | 39481-28-2 | CEFHJK |
| 342 | 2-methyldecanenitrile | 69300-15-8 | BDEFHJKL |
| 343 | 8,8-dimethyl-3a,4,5,6,7,7a-hexahydro-1H-4,7-methanoinden-6-yl propionate | 76842-49-4 | DEFHJK |
| 344 | Ethyl (3aR,4S,7R,7aR)-octahydro-3aH-4,7-methanoindene-3a-carboxylate | 80657-64-3 | DEFHIJK |
| 347 | Diethyl cyclohexane-1,4-dicarboxylate | 72903-27-6 | CEFHJK |
| 349 | (6-isopropyl-9-methyl-1,4-dioxaspiro[4.5]decan-2-yl)methanol | 63187-91-7 | CEFHJ |
| 350 | 2-isobutyl-4-methyltetrahydro-2H-pyran-4-ol | 63500-71-0 | BCEFHIJK |
| 352 | Undec-10-enenitrile | 53179-04-7 | BDEFHJK |
| 353 | (Z)-6-ethylideneoctahydro-2H-5,8-methanochromen-2-one | 69486-14-2 | CEFGJK |
| 356 | 3-(2-ethylphenyl)-2,2-dimethylpropanal | 67634-15-5 | BDHJK |
| 358 | (E)-4,8-dimethyldeca-4,9-dienal | 71077-31-1 | BDFHJK |
| 359 | (E)-4-((3aR,4R,7R,7aR)-1,3a,4,6,7,7a-hexahydro-5H-4,7-methanoinden-5-ylidene)-3-methylbutan-2-ol | 501929-47-1 | DEFHJK |
| 360 | 8,8-dimethyl-3a,4,5,6,7,7a-hexahydro-1H-4,7-methanoinden-6-yl acetate | 171102-41-3 | DEFHJK |
| 361 | 3-(4-ethylphenyl)-2,2-dimethylpropanenitrile | 134123-93-6 | DEFHJK |
| 362 | 2-heptylcyclopentan-1-one | 137-03-1 | DFHJKL |
| 363 | 1-ethoxyethoxy Cyclododecane | 389083-83-4 | DEFHJK |
| 364 | 3-cyclohexene-1-carboxylic acid, 2,6,6-trimethyl-, methyl ester | 815580-59-7 | ACHIJKL |
| 368 | Farnesyl acetate | 29548-30-9 | DEFHJK |
| 369 | Farnesol | 4602-84-0 | DEFHJK |
| 370 | Oxacyclohexadecan-2-one | 106-02-5 | DEFGJK |
| 371 | 1-cyclopentadec-4-en-1-one | 14595-54-1 | DEFGJK |
| 372 | 1-cyclopentadec-4-en-1-one | 35720-57-1 | DEFGJK |
| 373 | 2-methoxy-4-(4-methylenetetrahydro-2H-pyran-2-yl)phenol | 128489-04-3 | CGJ |
| 374 | Eugenol acetate | 93-28-7 | CFHJK |
| 375 | Eugenol | 97-53-0 | CHIK |
| 377 | Ethylmethylphenylglycidate | 77-83-8 | CFHJK |
| 378 | Ethylene brassylate | 105-95-3 | DFGJ |
| 381 | Ethyl undecylenate | 692-86-4 | DEFHJK |
| 385 | Ethyl palmitate | 628-97-7 | DEFHJ |
| 386 | Ethyl nonanoate | 123-29-5 | BDEFHJKL |
| 388 | Ethyl myristate | 124-06-1 | DEFHJK |
| 390 | Ethyl linalool | 10339-55-6 | BCEFHJK |
| 391 | Ethyl laurate | 106-33-2 | DEFHJK |
| 394 | Ethyl hexyl ketone | 925-78-0 | ADFHIKL |
| 397 | Ethyl decanoate | 110-38-3 | BDEFHJK |
| 398 | Ethyl gamma-Safranate | 35044-57-6 | ADHIJK |
| 407 | Ethyl 3-phenylglycidate | 121-39-1 | CGJK |
| 413 | 6-ethyl-2,10,10-trimethyl-1-oxaspiro[4.5]deca-3,6-diene | 79893-63-5 | BDEFHIJK |
| 414 | Elemol | 639-99-6 | DEFHJK |
| 415 | (2-(1-ethoxyethoxy)ethyl)benzene | 2556-10-7 | BCEFHJK |
| 416 | (E)-3-methyl-5-(2,2,3-trimethylcyclopent-3-en-1-yl)pent-4-en-2-ol | 67801-20-1 | DHJK |
| 417 | d-xylose | 58-86-6 | CGIJ |
| 418 | (E)-4-((3aS,7aS)-octahydro-5H-4,7-methanoinden-5-ylidene)butanal | 30168-23-1 | DFHJK |
| 421 | Dodecanal dimethyl acetal | 14620-52-1 | DEFHJK |
| 424 | d-Limonene | 5989-27-5 | ADEFGIJKL |
| 425 | Dipropylene Glycol | 25265-71-8 | CEFGIK |
| 426 | Dispirone | 83863-64-3 | BDEFHJK |
| 428 | Diphenyloxide | 101-84-8 | BDEFHK |
| 429 | Diphenylmethane | 101-81-5 | DEFGK |
| 432 | Dimethyl benzyl carbinyl butyrate | 10094-34-5 | DEFHJK |
| 436 | 2,6-dimethyloct-7-en-4-one | 1879-00-1 | ADEFHIJKL |
| 441 | Octahydro-1H-4,7-methanoinden-5-yl acetate | 64001-15-6 | DEFHJKL |
| 444 | Dihydrocarveol acetate | 20777-49-5 | BDEFHIJK |
| 445 | Dihydrocarveol | 619-01-2 | BCEFHIJKL |
| 449 | Dihydro Linalool | 18479-51-1 | BCEFGIJKL |
| 450 | Dihydro Isojasmonate | 37172-53-5 | DHJK |
| 453 | Dibutyl sulfide | 544-40-1 | ADEFHIKL |
| 457 | Dibenzyl | 103-29-7 | DEFGJK |
| 459 | delta-Undecalactone | 710-04-3 | DEFHJKL |
| 461 | delta-Elemene | 20307-84-0 | BDEFHJK |
| 462 | delta-Guaiene | 3691-11-0 | DEFHJK |
| 463 | delta-Dodecalactone | 713-95-1 | DEFHJK |
| 464 | delta-Decalactone | 705-86-2 | BDEFHIJKL |
| 465 | delta-Cadinene | 483-76-1 | DEFHJKL |
| 466 | delta-damascone | 57378-68-4 | ADHIJK |
| 467 | delta-Amorphene | 189165-79-5 | DEFHJKL |
| 468 | delta-3-Carene | 13466-78-9 | ADEFGIJKL |
| 470 | Decylenic alcohol | 13019-22-2 | BDEFHJK |
| 471 | Decyl propionate | 5454-19-3 | DEFHJK |
| 473 | Decanal diethyl acetal | 34764-02-8 | DEFHJK |
| 474 | Decahydro-beta-naphthol | 825-51-4 | BCEFGIK |
| 475 | 1-cyclohexylethyl (E)-but-2-enoate | 68039-69-0 | BDFHJK |
| 478 | 3-(4-isopropylphenyl)-2-methylpropanal | 103-95-7 | BDFHJK |

TABLE 1-continued

List of materials with at least one MORV from 1 to 5

| Number | Material Name | CAS Number | Comment Code |
|---|---|---|---|
| 479 | Cyclotetradecane | 295-17-0 | DEFGJKL |
| 480 | Cyclopentadecanone | 502-72-7 | DEFGJK |
| 482 | Cyclohexyl salicylate | 25485-88-5 | DFGJ |
| 484 | 3a,4,5,6,7,7a-hexahydro-1H-4,7-methanoinden-6-yl butyrate | 113889-23-9 | DEFHJK |
| 485 | Cyclic ethylene dodecanedioate | 54982-83-1 | DFGJ |
| 486 | 8,8-dimethyl-1,2,3,4,5,6,7,8-octahydronaphthalene-2-carbaldehyde | 68991-97-9 | DHJK |
| 487 | 3a,4,5,6,7,7a-hexahydro-1H-4,7-methanoinden-5-yl isobutyrate | 67634-20-2 | DEFHJK |
| 488 | Curzerene | 17910-09-7 | DHJK |
| 491 | Cumic alcohol | 536-60-7 | CHIJK |
| 493 | Coumarone | 1646-26-0 | BCEFHIK |
| 497 | 2-(3-phenylpropyl)pyridine | 2110-18-1 | CEFHJK |
| 498 | Dodecanenitrile | 2437-25-4 | DEFHJK |
| 501 | (E)-cycloheptadec-9-en-1-one | 542-46-1 | DEFGJ |
| 502 | Citryl acetate | 6819-19-8 | DFHJK |
| 503 | Citrus Propanol | 15760-18-6 | CEFHIJK |
| 505 | Citronitrile | 93893-89-1 | CEFHJK |
| 519 | Citral propylene glycol acetal | 10444-50-5 | CEFHJK |
| 520 | Citral dimethyl acetal | 7549-37-3 | BCEFHJK |
| 521 | Citral diethyl acetal | 7492-66-2 | BDEFHJK |
| 524 | cis-Ocimene | 3338-55-4 | ADGIKL |
| 527 | cis-Limonene oxide | 13837-75-7 | ADEFGIJKL |
| 529 | Cis-iso-ambrettolide | 36508-31-3 | DGJ |
| 530 | cis-6-nonenol | 35854-86-5 | BCEFHIKL |
| 531 | cis-carveol | 1197-06-4 | BCHIJK |
| 532 | cis-4-Decen-1-al | 21662-09-9 | ADHKL |
| 534 | cis-3-hexenyl-cis-3-hexenoate | 61444-38-0 | BDEFHJK |
| 537 | cis-3-Hexenyl salicylate | 65405-77-8 | DEFGJ |
| 541 | Cis-3-hexenyl Benzoate | 25152-85-6 | DEFHJK |
| 544 | cis-3-Hexenyl 2-methylbutyrate | 53398-85-9 | ADEFHJKL |
| 546 | cis-3, cis-6-nonadienol | 53046-97-2 | ACEFHK |
| 548 | Cinnamyl propionate | 103-56-0 | DEFHJK |
| 550 | Cinnamyl isobutyrate | 103-59-3 | DEFHJK |
| 551 | Cinnamyl formate | 104-65-4 | BCEFHK |
| 552 | Cinnamyl cinnamate | 122-69-0 | DHJ |
| 553 | Cinnamyl acetate | 103-54-8 | BCEFHK |
| 555 | Cinnamic alcohol | 104-54-1 | BCEFHIK |
| 558 | Cetyl alcohol | 36653-82-4 | DEFHJ |
| 559 | (E)-1-(2,6,6-trimethylcyclohex-2-en-1-yl)hepta-1,6-dien-3-one | 79-78-7 | DHJK |
| 560 | 2-methyl-4-(2,6,6-trimethylcyclohex-1-en-1-yl)butanal | 65405-84-7 | DFHJK |
| 561 | (3aR,5aR,9aR,9bR)-3a,6,6,9a-tetramethyldodecahydronaphtho[2,1-b]furan | 3738-00-9 | DEFHJK |
| 562 | 1,6-dioxacycloheptadecan-7-one | 6707-60-4 | DGJ |
| 563 | 1-(6-(tert-butyl)-1,1-dimethyl-2,3-dihydro-1H-inden-4-yl)ethan-1-one | 13171-00-1 | DEFHJK |
| 565 | Cedryl methyl ether | 19870-74-7 | ADEFHJK |
| 566 | Cedryl formate | 39900-38-4 | BDEFHJK |
| 567 | Cedryl acetate | 77-54-3 | DEFHJK |
| 568 | (4Z,8Z)-1,5,9-trimethyl-13-oxabicyclo[10.1.0]trideca-4,8-diene | 71735-79-0 | DFHJK |
| 569 | Cedrol | 77-53-2 | DEFHJK |
| 570 | 5-methyl-1-(2,2,3-trimethylcyclopent-3-en-1-yl)-6-oxabicyclo[3.2.1]octane | 139539-66-5 | DEFHJK |
| 571 | 5-methyl-1-(2,2,3-trimethylcyclopent-3-en-1-yl)-6-oxabicyclo[3.2.1]octane | 426218-78-2 | DFHJ |
| 572 | 1,1,2,3,3-pentamethyl-1,2,3,5,6,7-hexahydro-4H-inden-4-one | 33704-61-9 | BDEFHIJK |
| 573 | Caryophyllene alcohol acetate | 32214-91-8 | DEFHJK |
| 574 | Caryolan-1-ol | 472-97-9 | DEFHJK |
| 577 | Carvyl acetate | 97-42-7 | BDHIJK |
| 578 | Caprylnitrile | 124-12-9 | ACEFGIKL |
| 580 | Caprylic alcohol | 111-87-5 | ACEFGIKL |
| 581 | Caprylic acid | 124-07-2 | BCEFHIK |
| 582 | Capric acid | 334-48-5 | DEFHJK |
| 584 | Capraldehyde | 112-31-2 | ADHKL |
| 586 | 3-(4-methoxyphenyl)-2-methylpropanal | 5462-06-6 | BCHJK |
| 587 | Camphorquinone | 10373-78-1 | ACEFGJK |
| 589 | Camphene | 79-92-5 | ADEFGIJKL |
| 591 | Ethyl 2-methyl-4-oxo-6-pentylcyclohex-2-ene-1-carboxylate | 59151-19-8 | DHJ |
| 592 | Butylated hydroxytoluene | 128-37-0 | DEFGIJK |
| 594 | Butyl stearate | 123-95-5 | DEFHJ |
| 595 | Butyl butyryl lactate | 7492-70-8 | CEFGJK |
| 599 | Butyl 10-undecenoate | 109-42-2 | DEFHJK |
| 600 | 2-methyl-4-(2,2,3-trimethylcyclopent-3-en-1-yl)butan-1-ol | 72089-08-8 | DEFHJK |
| 601 | 3-(4-(tert-butyl)phenyl)propanal | 18127-01-0 | BDHJK |
| 603 | Bornyl isobutyrate | 24717-86-0 | BDEFHJK |
| 604 | Bornyl acetate | 76-49-3 | ADEFHIJKL |
| 606 | 2-ethoxy-2,6,6-trimethyl-9-methylenebicyclo[3.3.1]nonane | 68845-00-1 | BDEFHJK |
| 607 | (ethoxymethoxy)cyclododecane | 58567-11-6 | DEFHJK |
| 608 | Bisabolene | 495-62-5 | DEFHJK |
| 609 | Bigarade oxide | 72429-08-4 | ADEFHJKL |
| 610 | beta-Vetivone | 18444-79-6 | DHJK |
| 611 | beta-Terpinyl acetate | 10198-23-9 | BDHJK |
| 612 | beta-Terpineol | 138-87-4 | BCGIJK |
| 613 | beta-Sinensal | 60066-88-8 | DHJK |
| 614 | beta-Sesquiphellandrene | 20307-83-9 | DEFHJK |
| 615 | beta-Selinene | 17066-67-0 | BDEFGJK |
| 616 | beta-Santalol | 77-42-9 | DEFHJK |
| 618 | beta-Pinene | 127-91-3 | ADEFGIJKL |
| 620 | beta-Naphthyl ethyl ether | 93-18-5 | DEFHJK |
| 621 | beta-Patchoulline | 514-51-2 | BDEFGJKL |
| 624 | beta-Himachalene Oxide | 57819-73-5 | BDFHJK |
| 625 | beta-Himachalene | 1461-03-6 | DEFHJKL |
| 626 | beta-Guaiene | 88-84-6 | DEFHJKL |
| 627 | (2,2-dimethoxyethyl)benzene | 101-48-4 | DHJK |
| 628 | beta-Farnesene | 18794-84-8 | DEFHJK |
| 631 | beta-Copaene | 18252-44-3 | BDEFHJKL |
| 632 | beta-Cedrene | 546-28-1 | BDEFGJKL |
| 633 | beta-Caryophyllene | 87-44-5 | DEFHJKL |
| 635 | beta-Bisabolol | 15352-77-9 | DFHJK |
| 636 | Beta ionone epoxide | 23267-57-4 | BDEFHJK |
| 638 | Bergaptene | 484-20-8 | CGJ |
| 639 | Benzyl-tert-butanol | 103-05-9 | CEFGJK |
| 644 | Benzyl laurate | 140-25-0 | DEFHJ |
| 649 | Benzyl dimethyl carbinol | 100-86-7 | BCEFGIK |
| 650 | Benzyl cinnamate | 103-41-3 | DHJ |
| 653 | Benzyl benzoate | 120-51-4 | DHJ |
| 655 | Benzophenone | 119-61-9 | DEFHK |
| 658 | 7-isopentyl-2H-benzo[b][1,4]dioxepin-3(4H)-one | 362467-67-2 | DHJ |
| 659 | 2'-isopropyl-1,7,7-trimethylspiro[bicyclo[2.2.1]heptane-2,4'-[1,3]dioxane] | 188199-50-0 | DEFHJK |
| 660 | 4-(4-methylpent-3-en-1-yl)cyclohex-3-ene-1-carbonitrile | 21690-43-7 | DEFHJK |
| 661 | Aurantiol | 89-43-0 | DEFHJ |
| 663 | Anisyl phenylacetate | 102-17-0 | DFHJ |
| 668 | Methyl (E)-octa-4,7-dienoate | 189440-77-5 | ACEFHKL |
| 671 | Amyl Cinnamate | 3487-99-8 | DEFHJK |
| 673 | (3aR,5aS,9aS,9bR)-3a,6,6,9a-tetramethyldodecahydronaphtho[2,1-b]furan | 6790-58-5 | DEFHJK |
| 674 | (4aR,5R,7aS,9R)-2,2,5,8,8,9a-hexamethyloctahydro-4H-4a,9-methanoazuleno[5,6-d][1,3]dioxole | 211299-54-6 | DEFHJK |
| 675 | 2,5,5-trimethyl-1,2,3,4,5,6,7,8-octahydronaphthalen-2-ol | 71832-76-3 | DEFHJK |
| 676 | 2,5,5-trimethyl-1,2,3,4,5,6,7,8-octahydronaphthalen-2-ol | 41199-19-3 | DEFHJK |
| 677 | 1-((2-(tert-butyl)cyclohexyl)oxy)butan-2-ol | 139504-68-0 | DEFHJK |
| 678 | (3S,5aR,7aS,11aS,11bR)-3,8,8,11a-tetramethyldodecahydro-5H-3,5a-epoxynaphtho[2,1-c]oxepine | 57345-19-4 | DEFHJ |
| 679 | 2,2,6,6,7,8,8-heptamethyldecahydro-2H-indeno[4,5-b]furan | 476332-65-7 | ADEFHJK |

TABLE 1-continued

List of materials with at least one MORV from 1 to 5

| Number | Material Name | CAS Number | Comment Code |
|---|---|---|---|
| 680 | 2,2,6,6,7,8,8-heptamethyldecahydro-2H-indeno[4,5-b]furan | 647828-16-8 | ADEFHJK |
| 681 | Amber acetate | 37172-02-4 | BDEFHJK |
| 682 | Alpinofix | 811436-82-5 | DEFHJ |
| 683 | alpha-Thujone | 546-80-5 | ADEFGIJKL |
| 684 | alpha-Vetivone | 15764-04-2 | DHJK |
| 686 | alpha-Terpinyl propionate | 80-27-3 | BDEFHJK |
| 691 | alpha-Sinensal | 17909-77-2 | DHJK |
| 692 | alpha-Selinene | 473-13-2 | BDEFHJK |
| 693 | alpha-Santalene | 512-61-8 | ADEFHJKL |
| 694 | alpha-Santalol | 115-71-9 | DEFHJK |
| 696 | alpha-Patchoulene | 560-32-7 | ADEFHJKL |
| 697 | alpha-neobutenone | 56973-85-4 | BDHJK |
| 698 | alpha-Muurolene | 10208-80-7 | DEFHJKL |
| 700 | alpha-methyl ionone | 127-42-4 | BDHJK |
| 702 | alpha-Limonene | 138-86-3 | ADEFGIJKL |
| 704 | alpha-Irone | 79-69-6 | BDHJK |
| 706 | alpha-Humulene | 6753-98-6 | DEFHJK |
| 707 | alpha-Himachalene | 186538-22-7 | BDEFHJK |
| 708 | alpha-Gurjunene | 489-40-7 | ADEFHJKL |
| 709 | alpha-Guaiene | 3691-12-1 | DEFHJKL |
| 710 | alpha-Farnesene | 502-61-4 | DEFHJK |
| 711 | alpha-Fenchene | 471-84-1 | ADEFGIJKL |
| 712 | alpha-Eudesmol | 473-16-5 | DEFHJK |
| 713 | alpha-Curcumene | 4176-17-4 | DEFHJK |
| 714 | alpha-Cubebene | 17699-14-8 | ADEFHJKL |
| 715 | alpha-Cedrene epoxide | 13567-39-0 | ADEFHJK |
| 716 | alpha-Cadinol | 481-34-5 | BCEFGIK |
| 717 | alpha-Cadinene | 24406-05-1 | DEFHJKL |
| 718 | alpha-Bisabolol | 515-69-5 | DFHJK |
| 719 | alpha-bisabolene | 17627-44-0 | DEFHJK |
| 720 | alpha-Bergamotene | 17699-05-7 | BDEFHJKL |
| 721 | alpha-Amylcinnamyl alcohol | 101-85-9 | DEFHJ |
| 722 | alpha-Amylcinnamyl acetate | 7493-78-9 | DEFHJ |
| 723 | alpha-Amylcinnamaldehyde diethyl acetal | 60763-41-9 | DEFHJ |
| 724 | alpha-Amylcinnamaldehyde | 122-40-7 | DHJK |
| 725 | alpha-Amorphene | 23515-88-0 | DEFHJKL |
| 726 | alpha-Agarofuran | 5956-12-7 | BDEFHJK |
| 727 | 1-methyl-4-(4-methyl-3-penten-1-yl)-3-Cyclohexene-1-carboxaldehyde | 52475-86-2 | DFHJK |
| 730 | 1-Phenyl-2-pentanol | 705-73-7 | CEFHK |
| 731 | 1-Phenyl-3-methyl-3-pentanol | 10415-87-9 | CEFHJK |
| 733 | 2,3,4-trimethoxy-benzaldehyde | 2103-57-3 | BCGI |
| 735 | 2,4,5-trimethoxy-benzaldehyde | 4460-86-0 | BCG |
| 736 | 2,4,6-trimethoxybenzaldehyde | 830-79-5 | BCGI |
| 738 | 2,4-Nonadienal | 6750-03-4 | ACHKL |
| 741 | 2,6,10-Trimethylundecanal | 105-88-4 | BDFGJK |
| 742 | alpha,4-Dimethyl benzenepropanal | 41496-43-9 | ACHJK |
| 746 | Allyl cyclohexyl propionate | 2705-87-5 | BDEFHJK |
| 748 | Allyl amyl glycolate | 67634-00-8 | BCEFGJK |
| 750 | Allo-aromadendrene | 25246-27-9 | BDEFHJKL |
| 752 | Aldehyde C-11 | 143-14-6 | ADHJK |
| 754 | Methyl (E)-2-(((3,5-dimethylcyclohex-3-en-1-yl)methylene)amino)benzoate | 94022-83-0 | DEFHJ |
| 757 | 2,6,10-trimethylundec-9-enal | 141-13-9 | BDFHJK |
| 758 | Acetoxymethyl-isolongifolene (isomers) | 59056-62-1 | BDEFHJK |
| 763 | Acetate C9 | 143-13-5 | BDEFHJKL |
| 764 | Acetarolle | 744266-61-3 | DFHJK |
| 766 | Acetaldehyde phenylethyl propyl acetal | 7493-57-4 | CEFHJK |
| 767 | Acetaldehyde dipropyl acetal | 105-82-8 | ACEFGIKL |
| 768 | Acetaldehyde benzyl 2-methoxyethyl acetal | 7492-39-9 | BCEFHJK |
| 769 | (Z)-2-(4-methylbenzylidene)heptanal | 84697-09-6 | DHJ |
| 770 | 9-decenal | 39770-05-3 | ADHKL |
| 771 | 8-Hexadecenolide | 123-69-3 | DGJ |
| 772 | 7-Methoxycoumarin | 531-59-9 | CHK |
| 774 | 7-epi-alpha-Selinene | 123123-37-5 | BDEFHJK |
| 775 | 7-eip-alpha-Eudesmol | 123123-38-6 | DEFHJK |
| 776 | 7-Acetyl-1,1,3,4,4,6-hexamethyltetralin | 1506-02-1 | DEFHJ |
| 778 | 6-Isopropylquinoline | 135-79-5 | CEFHJK |
| 781 | 6,6-dimethyl-2-norpinene-2-propionaldehyde | 33885-51-7 | BCFHJK |
| 782 | 6,10,14-trimethyl-2-Pentadecanone | 502-69-2 | DEFHJK |
| 786 | 5-Isopropenyl-2-methyl-2-vinyltetrahydrofuran | 13679-86-2 | ACGIJKL |
| 788 | 5-Cyclohexadecenone | 37609-25-9 | DEFGJK |
| 791 | 4-Terpinenol | 562-74-3 | BCHIJK |
| 792 | 4-Pentenophenone | 3240-29-7 | BCEFHIK |
| 800 | 4-Carvomenthenol | 28219-82-1 | BCHIJK |
| 802 | 4,5,6,7-Tetrahydro-3,6-dimethylbenzofuran | 494-90-6 | BCEFHIJKL |
| 803 | 4-(p-Methoxyphenyl)-2-butanone | 104-20-1 | BCEFHJK |
| 804 | 3-Thujopsanone | 25966-79-4 | BDEFHJK |
| 805 | 3-Propylidenephthalide | 17369-59-4 | CEFHK |
| 806 | 3-Nonylacrolein | 20407-84-5 | BDFHJK |
| 807 | 3-Methyl-5-phenyl-1-pentanal | 55066-49-4 | BDFHJK |
| 814 | 3-Hexenyl isovalerate | 10032-11-8 | ADEFHJKL |
| 821 | 3,6-Dimethyl-3-octanyl acetate | 60763-42-0 | ADEFHIJKL |
| 824 | 3,4,5-trimethoxybenzaldehyde | 86-81-7 | BCGIK |
| 826 | 3-(p-Isopropylphenyl)propionaldehyde | 7775-00-0 | BDFHJK |
| 827 | 2-Undecenenitrile | 22629-48-7 | BDEFHJK |
| 828 | 2-Undecenal | 2463-77-6 | ADHJK |
| 829 | 2-trans-6-trans-Nonadienal | 17587-33-6 | ACHKL |
| 831 | 2-Phenylethyl butyrate | 103-52-6 | DEFHJK |
| 833 | 2-Phenyl-3-(2-furyl)prop-2-enal | 57568-60-2 | CHJ |
| 834 | 2-Phenoxyethanol | 122-99-6 | BCEFGIK |
| 837 | 2-Nonen-1-al | 2463-53-8 | ADHKL |
| 839 | 2-Nonanol | 628-99-9 | BDEFGIKL |
| 840 | 2-Nonanone | 821-55-6 | ADFHIKL |
| 849 | 2-Isobutyl quinoline | 93-19-6 | CEFHJK |
| 850 | 2-Hexylidene cyclopentanone | 17373-89-6 | DFHJKL |
| 852 | 2-Heptyl tetrahydrofuran | 2435-16-7 | BDEFHJKL |
| 856 | 2-Decenal | 3913-71-1 | ADHKL |
| 864 | 2,6-Nonadienal | 26370-28-5 | ACHKL |
| 865 | 2,6-Nonadien-1-ol | 7786-44-9 | ACEFHK |
| 866 | 2,6-dimethyl-octanal | 7779-07-9 | ADFGIJKL |
| 868 | 1-Decanol | 112-30-1 | BDEFGJK |
| 869 | 1-Hepten-1-ol, 1-acetate | 35468-97-4 | ACEFHKL |
| 870 | 10-Undecen-1-ol | 112-43-6 | DEFHJK |
| 871 | 10-Undecenal | 112-45-8 | ADHJK |
| 872 | 10-epi-gamma-Eudesmol | 15051-81-7 | DFHJK |
| 873 | 1,8-Thiocineol | 68391-28-6 | ADEFHIJKL |
| 876 | 1,3,5-undecatriene | 16356-11-9 | ADEFHJKL |
| 877 | 1,2-Dihydrolinalool | 2270-57-7 | BCEFGIJKL |
| 878 | 1,3,3-trimethyl-2-norbornanyl acetate | 13851-11-1 | ADEFHIJKL |
| 879 | 1,1,2,3,3-Pentamethylindan | 1203-17-4 | ADHIJKL |
| 881 | (Z)-6,10-dimethylundeca-5,9-dien-2-yl acetate | 3239-37-0 | DEFHJK |
| 884 | (Z)-3-Dodecenal | 68141-15-1 | BCFHJK |
| 885 | (S)-gamma-Undecalactone | 74568-05-1 | DEFHJKL |
| 886 | (R)-gamma-Undecalactone | 74568-06-2 | DEFHJKL |
| 890 | (E)-6,10-dimethylundeca-5,9-dien-2-yl acetate | 3239-35-8 | DEFHJK |
| 892 | (2Z)-3-methyl-5-phenyl-2-Pentenenitrile | 53243-59-7 | DEFHJK |
| 893 | (2S,5S,6S)-2,6,10,10-tetramethyl-1-oxaspiro[4_5]decan-6-ol | 65620-50-0 | DFHIJK |
| 894 | (2E)-3-methyl-5-phenyl-2-penteneitrile | 53243-60-0 | CEFHJK |
| 897 | (+)-Dihydrocarveol | 22567-21-1 | BCEFHIJKL |
| 905 | Menthone | 89-80-5 | ADEFGIJKL |
| 908 | (R,E)-2-methyl-4-(2,2,3-trimethylcyclopent-3-en-1-yl)but-2-en-1-ol | 185068-69-3 | CHJK |
| 912 | 2-(8-isopropyl-6-methylbicyclo[2.2.2]oct-5-en-2-yl)-1,3-dioxolane | 68901-32-6 | DEFHJK |
| 913 | gamma-methyl ionone | 7388-22-9 | BDHIJK |
| 914 | 3-(3-isopropylphenyl)butanal | 125109-85-5 | BDHJK |
| 916 | 3-(1-ethoxyethoxy)-3,7-dimethylocta-1,6-diene | 40910-49-4 | BDEFHJK |

TABLE 1-continued

List of materials with at least one MORV from 1 to 5

| Number | Material Name | CAS Number | Comment Code |
|---|---|---|---|
| 919 | 3a,4,5,6,7,7a-hexahydro-1H-4,7-methanoinden-6-yl propionate | 17511-60-3 | CEFHJK |
| 920 | Bulnesol | 22451-73-6 | DEFHJK |
| 922 | Benzyl phenylacetate | 102-16-9 | DHJ |
| 923 | Benzoin | 119-53-9 | CEFHJ |
| 924 | (E)-1,2,4-trimethoxy-5-(prop-1-en-1-yl)benzene | 2883-98-9 | BCFGJK |
| 925 | alpha,alpha,6,6-tetramethyl bicyclo[3.1.1]hept-2-ene-propanal | 33885-52-8 | BDFHJK |
| 926 | 7-epi-sesquithujene | 159407-35-9 | DEFHJKL |
| 927 | 5-Acetyl-1,1,2,3,3,6-hexamethylindan | 15323-35-0 | DEFHJK |
| 928 | 3-Methylphenethyl alcohol | 1875-89-4 | BCEFHIK |
| 929 | 3,6-Nonadien-1-ol | 76649-25-7 | ACEFHK |
| 930 | 2-Tridecenal | 7774-82-5 | BDFHJK |
| 933 | Patchouli alcohol | 5986-55-0 | DEFHIJK |
| 937 | p-Cresyl isobutyrate | 103-93-5 | BDHJK |
| 939 | p-Cresyl n-hexanoate | 68141-11-7 | DEFHJK |
| 941 | 5-hexyl-4-methyldihydrofuran-2(3H)-one | 67663-01-8 | BDEFHIJKL |
| 942 | Ethyl (2Z,4E)-deca-2,4-dienoate | 3025-30-7 | BDEFHJK |
| 943 | Pelargene | 68039-40-7 | DEFHJK |
| 945 | 2-cyclohexylidene-2-phenylacetonitrile | 10461-98-0 | DFHJK |
| 946 | Perillaldehyde | 2111-75-3 | ACHIJK |
| 947 | Perillyl acetate | 15111-96-3 | DFHJK |
| 948 | Perillyl alcohol | 536-59-4 | CHIJK |
| 950 | (2-isopropoxyethyl)benzene | 68039-47-4 | ACEFHJKL |
| 951 | Ethyl (2Z,4E)-deca-2,4-dienoate | 313973-37-4 | BDEFHJK |
| 953 | (2-(cyclohexyloxy)ethyl)benzene | 80858-47-5 | DEFHJK |
| 954 | Phenethyl 2-methylbutyrate | 24817-51-4 | DEFHJK |
| 955 | Phenethyl alcohol | 60-12-8 | BCEFGIK |
| 959 | Phenethyl phenylacetate | 102-20-5 | DHJ |
| 962 | Phenoxanol | 55066-48-3 | DEFHJK |
| 965 | Phenyl benzoate | 93-99-2 | DFHJK |
| 967 | Phenyl ethyl benzoate | 94-47-3 | DHJ |
| 969 | Phenylacetaldehyde ethyleneglycol acetal | 101-49-5 | BCEFGIK |
| 973 | 2-(6,6-dimethylbicyclo[3.1.1]hept-2-en-2-yl)acetaldehyde | 30897-75-7 | ACFHIJKL |
| 974 | Pinocarveol | 5947-36-4 | BCEFGIJKL |
| 976 | Piperonyl acetone | 55418-52-5 | CEFGJ |
| 978 | 3a,4,5,6,7,7a-hexahydro-1H-4,7-methanoinden-6-yl pivalate | 68039-44-1 | DEFHJK |
| 980 | (4aR,8aS)-7-methyloctahydro-1,4-methanonaphthalen-6(2H)-one | 41724-19-0 | CEFGJKL |
| 982 | p-Menth-3-en-1-ol | 586-82-3 | BCGIJK |
| 985 | (E)-3,3-dimethyl-5-(2,2,3-trimethylcyclopent-3-en-1-yl)pent-4-en-2-ol | 107898-54-4 | DHJK |
| 988 | 1-methyl-4-(4-methylpent-3-en-1-yl)cyclohex-3-ene-1-carbaldehyde | 52474-60-9 | DFHJK |
| 993 | Propylene glycol | 57-55-6 | ACEFGIKL |
| 998 | p-Tolyl phenylacetate | 101-94-0 | DFHJ |
| 1000 | Ethyl 2,4,7-decatrienoate | 78417-28-4 | BDEFHJK |
| 1003 | 2-benzyl-4,4,6-trimethyl-1,3-dioxane | 67633-94-7 | DEFHJK |
| 1006 | 2,4-dimethyl-4-phenyltetrahydrofuran | 82461-14-1 | BDEFHJK |
| 1007 | (2R,4a'R,8a'R)-3',7'-dimethyl-3',4',4a',5',8',8a'-hexahydro-1'H-spiro[oxirane-2,2'-[1,4]methanonaphthalene] | 41816-03-9 | DEFHJK |
| 1008 | (Z)-6-ethylideneoctahydro-2H-5,8-methanochromene | 93939-86-7 | BCEFHJKL |
| 1009 | 2-((S)-1-((S)-3,3-dimethylcyclohexyl)ethoxy)-2-oxoethyl propionate | 236391-76-7 | DFHJ |
| 1010 | Methyl 2,2-dimethyl-6-methylenecyclohexane-1-carboxylate | 81752-87-6 | ADHIJKL |
| 1012 | 2-methyl-5-phenylpentan-1-ol | 25634-93-9 | DEFHJK |
| 1016 | 4-methyl-2-phenyl-3,6-dihydro-2H-pyran | 60335-71-9 | BCEFGJK |
| 1020 | Sabinol | 471-16-9 | BCEFHIJKL |
| 1021 | Safrole | 94-59-7 | BCEFHK |
| 1022 | 2,2,7,9-tetramethylspiro(5.5)undec-8-en-1-one | 502847-01-0 | DHIJK |
| 1023 | 3-methyl-5-(2,2,3-trimethylcyclopent-3-en-1-yl)pentan-2-ol | 65113-99-7 | DEFHJK |
| 1024 | (Z)-2-ethyl-4-(2,2,3-trimethylcyclopent-3-en-1-yl)but-2-en-1-ol | 28219-61-6 | DEFHJK |
| 1025 | (E)-2-methyl-4-(2,2,3-trimethylcyclopent-3-en-1-yl)but-2-en-1-ol | 28219-60-5 | CHJK |
| 1026 | 5-methoxyoctahydro-1H-4,7-methanoindene-2-carbaldehyde | 86803-90-9 | CHJK |
| 1027 | 5-methoxyoctahydro-1H-4,7-methanoindene-2-carbaldehyde | 193425-86-4 | CHJK |
| 1028 | Sclareol | 515-03-7 | DEFHJ |
| 1029 | Sclareol oxide | 5153-92-4 | DEFHJK |
| 1031 | Selina-3,7(11)-diene | 6813-21-4 | DEFHJKL |
| 1032 | 2-(1-(3,3-dimethylcyclohexyl)ethoxy)-2-methylpropyl cyclopropanecarboxylate | 477218-42-1 | DEFHJ |
| 1033 | 3-(4-isobutylphenyl)-2-methylpropanal | 6658-48-6 | DHJK |
| 1035 | Spathulenol | 6750-60-3 | DEFHJK |
| 1036 | Spirambrene | 533925-08-5 | BCEFHJK |
| 1037 | Spirodecane | 6413-26-9 | BCEFGIJKL |
| 1038 | 1-(spiro[4.5]dec-7-en-7-yl)pent-4-en-1-one | 224031-70-3 | DGJK |
| 1042 | 2-(4-methylthiazol-5-yl)ethan-1-ol | 137-00-8 | CGIKL |
| 1043 | 2-(heptan-3-yl)-1,3-dioxolane | 4359-47-1 | ACEFHIJKL |
| 1045 | (Z)-dodec-4-enal | 21944-98-9 | BDFHJK |
| 1046 | tau-Cadinol | 5937-11-1 | DEFHJK |
| 1047 | tau-Muurolol | 19912-62-0 | DEFHJK |
| 1053 | Tetrahydrojasmone | 13074-63-0 | BDFHIJKL |
| 1057 | 2,6,10,10-tetramethyl-1-oxaspiro[4.5]dec-6-ene | 36431-72-8 | BDFHIJKL |
| 1059 | Thiomenthone | 38462-22-5 | BDEFHIJKL |
| 1060 | Thujopsene | 470-40-6 | BDEFGJKL |
| 1062 | Thymol methyl ether | 1076-56-8 | ADHIJKL |
| 1063 | 1-(2,2,6-trimethylcyclohexyl)hexan-3-ol | 70788-30-6 | DEFHJK |
| 1064 | trans, trans-2,4-Nonadienal | 5910-87-2 | ACHKL |
| 1065 | trans, trans-Farnesol | 106-28-5 | DEFHJK |
| 1066 | trans-2, cis-6-Nonadienal | 557-48-2 | ACHKL |
| 1067 | trans-2-Decenal | 3913-81-3 | ADHKL |
| 1070 | trans-2-Nonen-1-al | 18829-56-6 | ADHKL |
| 1072 | trans-3, cis-6-nonadienol | 56805-23-3 | ACEFHK |
| 1073 | trans-4-Decen-1-al | 65405-70-1 | ADHKL |
| 1075 | trans-ambrettolide | 51155-12-5 | DGJ |
| 1077 | trans-beta-ocimene | 13877-91-3 | ADGIKL |
| 1078 | trans-beta-Ocimene | 3779-61-1 | ADGIKL |
| 1082 | trans-Geraniol | 106-24-1 | BCHIK |
| 1083 | trans-Hedione | 2570-03-8 | DFHJK |
| 1085 | 7-(1,1-Dimethylethyl)-2H-1,5-benzodioxepin-3(4H)-one | 195251-91-3 | CEFHJ |
| 1089 | Tricyclone | 68433-81-8 | DEFHJK |
| 1090 | Tridecyl alcohol | 112-70-9 | DEFGJK |
| 1091 | Triethyl citrate | 77-93-0 | CEFGJ |
| 1093 | Methyl 2-((1-hydroxy-3-phenylbutyl)amino)benzoate | 144761-91-1 | DFHJ |
| 1095 | 1-((2E,5Z,9Z)-2,6,10-trimethylcyclododeca-2,5,9-trien-1-yl)ethan-1-one | 28371-99-5 | DHJK |
| 1097 | Decahydro-2,6,6,7,8,8-hexamethyl-2h-indeno(4,5-b)furan | 338735-71-0 | BDEFHJK |
| 1099 | 13-methyl oxacyclopentadec-10-en-2-one | 365411-50-3 | DEFHJK |
| 1102 | Undecanal | 112-44-7 | BDHJK |
| 1104 | (E)-4-methyldec-3-en-5-ol | 81782-77-6 | BDEFHIJK |
| 1105 | Valencene | 4630-07-3 | BDEFHJK |
| 1107 | Valerianol | 20489-45-6 | DEFHJK |
| 1111 | Vanillin isobutyrate | 20665-85-4 | CHJ |
| 1113 | Vaniwhite | 5533-03-9 | CGIK |

TABLE 1-continued

List of materials with at least one MORV from 1 to 5

| Number | Material Name | CAS Number | Comment Code |
|---|---|---|---|
| 1116 | (Z)-2-methyl-4-(2,6,6-trimethylcyclohex-2-en-1-yl)but-2-enal | 68555-62-4 | BDFHJK |
| 1117 | Methyl 2,4-dihydroxy-3,6-dimethylbenzoate | 4707-47-5 | CGIJ |
| 1120 | 1-methoxy-3a,4,5,6,7,7a-hexahydro-1H-4,7-methanoindene | 27135-90-6 | ACEFHJKL |
| 1121 | Methyl (Z)-2-((3-(4-(tert-butyl)phenyl)-2-methylpropylidene)amino)benzoate | 91-51-0 | DFHJ |
| 1125 | (Z)-hex-3-en-1-yl isobutyrate | 41519-23-7 | ADEFHJKL |
| 1126 | Vertacetal | 5182-36-5 | BCFHJK |
| 1129 | 1-((3R,3aR,7R,8aS)-3,6,8,8-tetramethyl-2,3,4,7,8,8a-hexahydro-1H-3a,7-methanoazulen-5-yl)ethan-1-one | 32388-55-9 | DHJK |
| 1131 | Methyl (Z)-2-(((2,4-dimethylcyclohex-3-en-1-yl)methylene)amino)benzoate | 68738-99-8 | DEFHJ |
| 1135 | Vetiverol | 89-88-3 | CEFHIJK |
| 1136 | Vetivert Acetate | 117-98-6 | DEFHJK |
| 1137 | Decahydro-3H-spiro[furan-2,5'-[4,7]methanoindene] | 68480-11-5 | DEFGJKL |
| 1138 | (2Z,6E)-nona-2,6-dienenitrile | 67019-89-0 | ACEFHKL |
| 1139 | (Z)-cycloocct-4-en-1-yl methyl carbonate | 87731-18-8 | BCHJKL |
| 1140 | (1aR,4S,4aS,7R,7aS,7bS)-1,1,4,7-tetramethyldecahydro-1H-cyclopropa[e]azulen-4-ol | 552-02-3 | DEFHJK |
| 1142 | 3,5,5,6,7,8,8-heptamethyl-5,6,7,8-tetrahydronaphthalene-2-carbonitrile | 127459-79-4 | DHJ |
| 1143 | (1S,2S,3S,5R)-2,6,6-trimethylspiro[bicyclo[3.1.1]heptane-3,1'-cyclohexan]-2'-en-4'-one | 133636-82-5 | DEFHJK |
| 1144 | 1',1',5',5'-tetramethylhexahydro-2'H,5'H-spiro[[1,3]dioxolane-2,8'-[2,4a]methanonaphthalene] | 154171-76-3 | DEFHJK |
| 1145 | 1',1',5',5'-tetramethylhexahydro-2'H,5'H-spiro[[1,3]dioxolane-2,8'-[2,4a]methanonaphthalene] K | 154171-77-4 | DEFHJK |
| 1146 | 4-(4-hydroxy-3-methoxyphenyl)butan-2-one | 122-48-5 | CEFGJ |
| 1147 | (1R,8aR)-4-isopropyl-1,6-dimethyl-1,2,3,7,8,8a-hexahydronaphthalene | 41929-05-9 | DEFHJKL |
| 1148 | 4,5-epoxy-4,11,11-trimethyl-8-methylenebicyclo[7.2.0]undecane | 1139-30-6 | DEFHJK |
| 1149 | 1,3,4,6,7,8alpha-hexahydro-1,1,5,5-tetramethyl-2H-2,4alpha-methanophtalen-8(5H)-one | 23787-90-8 | DEFHIJK |

TABLE 2

List of materials with at least one MORV greater than 5 to 10

| Number | Material Name | CAS Number | Comment Code |
|---|---|---|---|
| 2 | 2,4-dimethyl-2-(5,5,8,8-tetramethyl-5,6,7,8-tetrahydronaphthalen-2-yl)-1,3-dioxolane | 131812-67-4 | DFHJ |
| 23 | 3a,5,6,7,8,8b-hexahydro-2,2,6,6,7,8,8-heptamethyl-4H-indeno(4,5-d)-1,3-dioxole | 823178-41-2 | DEFHJK |
| 141 | 2,4-dimethyl-4,4a,5,9b-tetrahydroindeno[1,2-d][1,3]dioxine | 27606-09-3 | CEFHJK |
| 185 | (1-methyl-2-((1,2,2-trimethylbicyclo[3.1.0]hexan-3-yl)methyl)cyclopropyl)methanol | 198404-98-7 | DEFHJK |
| 227 | Isobornylcyclohexanol | 68877-29-2 | DEFHJK |
| 230 | Isobornyl cyclohexanol | 66072-32-0 | DEFHJK |
| 246 | Indol/Hydroxycitronellal Schiff base | 67801-36-9 | DEFHJ |
| 248 | Hydroxymethyl isolongifolene | 59056-64-3 | DEFHJK |

TABLE 2-continued

List of materials with at least one MORV greater than 5 to 10

| Number | Material Name | CAS Number | Comment Code |
|---|---|---|---|
| 343 | 8,8-dimethyl-3a,4,5,6,7,7a-hexahydro-1H-4,7-methanoinden-6-yl propionate | 76842-49-4 | DEFHJK |
| 359 | (E)-4-((3aR,4R,7R,7aR)-1,3a,4,6,7,7a-hexahydro-5H-4,7-methanoinden-5-ylidene)-3-methylbutan-2-ol | 501929-47-1 | DEFHJK |
| 565 | Cedryl methyl ether | 19870-74-7 | BDEFHJK |
| 631 | beta-Copaene | 18252-44-3 | BDEFHJKL |
| 659 | 2'-isopropyl-1,7,7-trimethylspiro[bicyclo[2.2.1]heptane-2,4'-[1,3]dioxane | 869292-93-3 | BDEFHJK |
| 674 | (4aR,5R,7aS,9R)-2,2,5,8,8,9a-hexamethyloctahydro-4H-4a,9-methanoazuleno[5,6-d][1,3]dioxole | 211299-54-6 | DEFHJK |
| 678 | (3S,5aR,7aS,11aS,11bR)-3,8,8,11a-tetramethyldodecahydro-5H-3,5a-epoxynaphtho[2,1-c]oxepine | 57345-19-4 | DEFHJ |
| 679 | 2,2,6,6,7,8,8-heptamethyldecahydro-2H-indeno[4,5-b]furan | 476332-65-7 | DEFHJK |
| 715 | alpha-Cedrene epoxide | 13567-39-0 | BDEFHJK |
| 758 | Acetoxymethyl-isolongifolene (isomers) | 59056-62-1 | DEFHJK |
| 1028 | Sclareol | 515-03-7 | DEFHJ |
| 1097 | Decahydro-2,6,6,7,8,8-hexamethyl-2h-indeno(4,5-b)furan | 338735-71-0 | DEFHJK |

TABLE 3

List of materials with at least one MORV from 0.5 to less than 1

| Number | Material Name | CAS Number | Comment Code |
|---|---|---|---|
| 12 | 1-ethoxy-4-(tert-pentyl)cyclohexane | 181258-89-9 | ADEFHJK |
| 19 | (3Z)-1-(2-buten-1-yloxy)-3-hexene | 888744-18-1 | ADEFHJKL |
| 20 | 4-(2-methoxypropan-2-yl)-1-methylcyclohex-1-ene | 14576-08-0 | ADHIJKL |
| 24 | O-Methyl linalool | 60763-44-2 | ADHIJKL |
| 26 | o-Methoxycinnamaldehyde | 1504-74-1 | ACHK |
| 27 | Octanal, 3,7-dimethyl- | 25795-46-4 | ADGIJKL |
| 53 | 3,3-Dimethyl-5(2,2,3-Trimethyl-3-Cyclopenten-1yl)-4-Penten-2-ol | 329925-33-9 | CEFHJ |
| 54 | n-Hexyl salicylate | 6259-76-3 | DEFHJ |
| 55 | n-Hexyl 2-butenoate | 19089-92-0 | ADEFHJKL |
| 59 | Neryl Formate | 2142-94-1 | BCEFHJK |
| 72 | Methyl-beta-ionone | 127-43-5 | DHJK |
| 73 | Myroxide | 28977-57-3 | ADGIJKL |
| 81 | (E)-3,7-dimethylocta-4,6-dien-3-ol | 18479-54-4 | BCEFGIJK |
| 84 | (Z)-hex-3-en-1-yl cyclopropanecarboxylate | 188570-78-7 | BCEFHIKL |
| 96 | Methyl phenyl carbinyl propionate | 120-45-6 | BCHJK |
| 97 | Methyl phenylacetate | 101-41-7 | ACEFHIKL |
| 107 | 2-methyl-6-oxaspiro[4.5]decan-7-one | 91069-37-3 | BCEFGIKL |
| 111 | Methyl geraniate | 2349-14-6 | BCHJKL |
| 115 | 2-ethoxy-4-(methoxymethyl)phenol | 5595-79-9 | CFGK |
| 116 | Methyl cyclopentylideneacetate | 40203-73-4 | ACEFHIKL |
| 125 | Methoxymelonal | 62439-41-2 | ACGIJK |
| 133 | ((1s,4s)-4-isopropylcyclohexyl)methanol | 13828-37-0 | BDEFHIJK |
| 147 | Linalyl propionate | 144-39-8 | BDFHJK |
| 150 | Linalyl formate | 115-99-1 | ACFHJK |
| 151 | Linalyl butyrate | 78-36-4 | BDEFHJK |
| 154 | Linalyl acetate | 115-95-7 | BDHJK |

TABLE 3-continued

List of materials with at least one MORV from 0.5 to less than 1

| Number | Material Name | CAS Number | Comment Code |
|---|---|---|---|
| 157 | Linalool | 78-70-6 | BCEFGIJK |
| 163 | (Z)-hex-3-en-1-yl methyl carbonate | 67633-96-9 | ACEFGKL |
| 166 | Lepidine | 491-35-0 | BCEFHIKL |
| 169 | L-Carvone | 6485-40-1 | ACGIJKL |
| 181 | Khusinil | 75490-39-0 | DHJK |
| 191 | Isoraldeine | 1335-46-2 | BDHIJK |
| 194 | Isopropylvinylcarbinol | 4798-45-2 | ACGIKL |
| 198 | Isopropyl 2-methylbutyrate | 66576-71-4 | ACEFGIJKL |
| 201 | Isopentyrate | 80118-06-5 | ADEFGIJKL |
| 204 | Isononyl acetate | 40379-24-6 | BDEFHJKL |
| 205 | Isononanol | 27458-94-2 | BDEFGIKL |
| 213 | Isoeugenyl acetate | 93-29-8 | CFHJK |
| 214 | Isoeugenol | 97-54-1 | CEFHIK |
| 232 | Isoborneol | 124-76-5 | ACEFHIJKL |
| 237 | Isoamyl octanoate | 2035-99-6 | DEFHJK |
| 239 | Isoamyl isobutyrate | 2050-01-3 | ACEFGIJKL |
| 255 | Hydrocinnamic acid | 501-52-0 | CEFHIK |
| 258 | Hydratopic alcohol | 1123-85-9 | BCEFHIK |
| 264 | Hexyl propanoate | 2445-76-3 | ADEFHIKL |
| 270 | Hexyl butyrate | 2639-63-6 | BDEFHJKL |
| 273 | Hexyl 2-methylbutanoate | 10032-15-2 | BDEFHJKL |
| 275 | Hexyl 2-furoate | 39251-86-0 | DEFHJK |
| 282 | Heptyl alcohol | 111-70-6 | ACEFGIKL |
| 283 | Heptyl acetate | 112-06-1 | ADEFHKL |
| 284 | Heptaldehyde | 111-71-7 | ACHIKL |
| 287 | Heliotropin | 120-57-0 | BCGIK |
| 302 | Geranyl nitrile | 5146-66-7 | BCEFHKL |
| 306 | Geranyl formate | 105-86-2 | BCEFHJK |
| 308 | Geranyl caprylate | 51532-26-4 | DEFHJ |
| 310 | Geranyl benzoate | 94-48-4 | DFHJ |
| 312 | Geranial | 141-27-5 | ACHIKL |
| 314 | N,2-dimethyl-N-phenylbutanamide | 84434-18-4 | BCEFHJK |
| 319 | gamma-Terpinene | 99-85-4 | ADEFGIJKL |
| 346 | 2-(sec-butyl)cyclohexan-1-one | 14765-30-1 | ADFHIKL |
| 354 | 3-(2-ethylphenyl)-2,2-dimethylpropanal | 67634-14-4 | BDHJK |
| 355 | 2-(tert-butyl)cyclohexyl ethyl carbonate | 67801-64-3 | BDFHJK |
| 365 | 2-(tert-butyl)cyclohexyl ethyl carbonate | 81925-81-7 | ACFHIKL |
| 366 | Fenchyl alcohol | 1632-73-1 | ACGIJKL |
| 376 | Eucalyptol | 470-82-6 | ADEFGIJKL |
| 379 | Ethyl vanillin acetate | 72207-94-4 | CHJ |
| 387 | Ethyl octanoate | 106-32-1 | BDEFHJKL |
| 400 | Ethyl cinnamate | 103-36-6 | BCEFHK |
| 412 | Ethyl 2-(cyclohexyl)propionate | 2511-00-4 | BDFHIJKL |
| 419 | d-p-8(9)-Menthen-2-one | 5524-05-0 | ACGIJKL |
| 420 | 4-methyl-2-phenyltetrahydro-2H-pyran | 94201-73-7 | BDEFHJK |
| 437 | Dihydromyrcenol | 18479-58-8 | ADEFGIJK |
| 438 | Dihydrojasmone | 1128-08-1 | BCFHIJKL |
| 439 | Dihydroisophorone | 873-94-9 | ACEFGIJKL |
| 440 | Dihydroeugenol | 2785-87-7 | CEFHIJK |
| 442 | Dihydrocoumarin | 119-84-6 | BCGIKL |
| 443 | Dihydrocarvone | 7764-50-3 | ACGIJKL |
| 447 | Dihydro-alpha-terpinyl acetate | 80-25-1 | BDEFHIJKL |
| 448 | Dihydro-alpha-ionone | 31499-72-6 | BDHIJK |
| 454 | Dibenzyl ether | 103-50-4 | DEFHJK |
| 455 | Dibutyl o-phthalate | 84-74-2 | DEFHJ |
| 469 | 2-pentylcyclopentan-1-one | 4819-67-4 | BDFHIKL |
| 472 | Decyl anthranilate | 18189-07-6 | DEFHJ |
| 477 | Methyl (1s,4s)-1,4-dimethylcyclohexane-1-carboxylate | 23059-38-3 | ADEFHIJKL |
| 481 | Cyclohexylethyl acetate | 21722-83-8 | BDEFHJKL |
| 492 | Creosol | 93-51-6 | BCHIK |
| 495 | Cosmene | 460-01-5 | ADEFGIKL |
| 496 | 4-cyclohexyl-2-methylbutan-2-ol | 83926-73-2 | BDEFGIJK |
| 504 | 2-benzyl-2-methylbut-3-enenitrile | 97384-48-0 | BDHJK |
| 509 | Citronellyl nitrile | 51566-62-2 | BCEFGIKL |
| 510 | Citronellyl phenylacetate | 139-70-8 | DFHJ |
| 512 | Citronellyl formate | 105-85-1 | BCEFGJKL |
| 515 | Citronellyl benzoate | 10482-77-6 | DFHJ |
| 517 | Citronellol | 106-22-9 | BCHIJKL |
| 518 | Citronellal | 106-23-0 | ACHIJKL |
| 522 | Citral | 5392-40-5 | ACHIKL |
| 525 | cis-Pinane | 6876-13-7 | ADEFGIJKL |
| 526 | (Z)-3-methyl-2-(pent-2-en-1-yl)cyclopent-2-en-1-one | 488-10-8 | BCHIJKL |
| 528 | cis-iso-Eugenol | 5912-86-7 | CEFHIK |
| 535 | cis-3-Hexenyl valerate | 35852-46-1 | BDEFHJKL |
| 536 | cis-3-Hexenyl tiglate | 67883-79-8 | BDEFHJK |
| 538 | cis-3-Hexenyl propionate | 33467-74-2 | BDEFHJ |
| 540 | cis-3-Hexenyl butyrate | 16491-36-4 | ADEFHJKL |
| 542 | cis-3-Hexen-1-ol | 928-96-1 | ACEFHIKL |
| 547 | cis-2-Hexenol | 928-94-9 | ACEFHIKL |
| 549 | Cinnamyl nitrile | 4360-47-8 | ACEFGIK |
| 554 | Cinnamic aldehyde | 104-55-2 | ACHIK |
| 556 | Cinnamyl nitrile | 1885-38-7 | ACEFGIK |
| 557 | Chloroxylenol | 88-04-0 | BCHIJK |
| 575 | Carvacrol | 499-75-2 | DHIJK |
| 576 | Carvone | 99-49-0 | ACGIJKL |
| 579 | Carbitol | 111-90-0 | BCEFGIK |
| 583 | Caproyl alcohol | 111-27-3 | ACEFGIKL |
| 585 | 2-(2,2,3-trimethylcyclopent-3-en-1-yl)acetonitrile | 15373-31-6 | ACGIJKL |
| 588 | Camphor | 76-22-2 | ACEFGIJKL |
| 602 | (E)-2-methyl-4-(2,6,6-trimethylcyclohex-1-en-1-yl)but-2-enal | 3155-71-3 | DHJK |
| 605 | Borneol | 507-70-0 | ACEFHIJKL |
| 617 | beta-Pinene epoxide | 6931-54-0 | ACEFGIJKL |
| 619 | beta-Phellandrene | 555-10-2 | ADEFGIJKL |
| 640 | Benzylacetone | 2550-26-7 | ACEFGIK |
| 641 | Benzyl salicylate | 118-58-1 | DFGJ |
| 645 | Benzyl isovalerate | 103-38-8 | BDEFHJK |
| 647 | Benzyl isobutyrate | 103-28-6 | BCHJK |
| 651 | Benzyl butyrate | 103-37-7 | BCEFHJK |
| 652 | Benzyl alcohol | 100-51-6 | ACEFGIKL |
| 662 | 1-(3,3-dimethylcyclohexyl)ethyl formate | 25225-08-5 | ADEFHIJKL |
| 664 | Anisyl acetate | 104-21-2 | BCEFGK |
| 665 | Anisyl formate | 122-91-8 | BCEFGK |
| 667 | Anethole | 104-46-1 | ACEFHK |
| 672 | Amyl benzoate | 2049-96-9 | DEFHJK |
| 687 | alpha-Terpinyl acetate | 80-26-2 | BDHJK |
| 699 | alpha-methyl-cyclohexanepropanol | 10528-67-3 | BDEFHIK |
| 701 | alpha-methyl cinnamaldehyde | 101-39-3 | ACHIK |
| 703 | alpha-Isomethylionone | 127-51-5 | BDHIJK |
| 740 | 2,5-Dimethyl-4-methoxy-3(2H)-furanone | 4077-47-8 | ACEFGIJKL |
| 743 | Allyl phenoxyacetate | 7493-74-5 | BCGK |
| 744 | Allyl Phenethyl ether | 14289-65-7 | ACEFHK |
| 745 | Allyl heptanoate | 142-19-8 | ADEFHJKL |
| 755 | N-ethyl-N-(m-tolyl)propionamide | 179911-08-1 | CEFHJK |
| 760 | 3-hydroxybutan-2-one | 513-86-0 | ACEFGIKL |
| 761 | Acetoanisole | 100-06-1 | BCEFHIK |
| 777 | 6-Methylquinoline | 91-62-3 | BCEFHIKL |
| 779 | 6,8-Diethyl-2-nonanol | 70214-77-6 | BDEFGIJKL |
| 784 | 5-Methyl-3-heptanone | 541-85-5 | ACFGIKL |
| 789 | 4-Vinylphenol | 2628-17-3 | BCHIK |
| 796 | 4-hydroxy-3-methoxy-cinnamaldehyde | 458-36-6 | CH |
| 797 | 4-Ethylguaiacol | 2785-89-9 | CEFHIK |
| 799 | 4-Damascol | 4927-36-0 | BDFHJK |
| 808 | 3-methyl-4-phenylpyrazole | 13788-84-6 | CEFHK |
| 810 | 3-Methyl-1,2-cyclopentanedione | 765-70-8 | ACEFGIKL |
| 811 | 3-Methoxy-5-methylphenol | 3209-13-0 | BCHIK |

TABLE 3-continued

List of materials with at least one MORV from 0.5 to less than 1

| Number | Material Name | CAS Number | Comment Code |
|---|---|---|---|
| 812 | 3-Methoxy-3-Methyl Butanol | 56539-66-3 | ACGIKL |
| 817 | 3-Hexenol | 544-12-7 | ACEFHIKL |
| 819 | 3,7-dimethyl-2-methylene-6-octenal | 22418-66-2 | ADFHIJK |
| 820 | 3,7-dimethyl-1-octanol | 106-21-8 | BDEFGIJKL |
| 832 | 2-Phenylethyl acetate | 103-45-7 | BCEFHK |
| 835 | 2-Phenethyl propionate | 122-70-3 | BCEFHJK |
| 836 | 2-Pentylcyclopentan-1-ol | 84560-00-9 | DEFHIKL |
| 838 | 2-nonanone propylene glycol acetal | 165191-91-3 | BDEFHJK |
| 845 | 2-Methoxy-3-(1-methylpropyl)pyrazine | 24168-70-5 | BCEFGIK |
| 846 | 2-isopropyl-N,2,3-trimethylbutyramide | 51115-67-4 | ACEFGIJK |
| 847 | 2-Isopropyl-5-methyl-2-hexenal | 35158-25-9 | ADFGIJKL |
| 848 | 2-Isopropyl-4-methylthiazole | 15679-13-7 | ACHIJKL |
| 851 | 2-Hexen-1-ol | 2305-21-7 | ACEFHIKL |
| 858 | 2-Butoxyethanol | 111-76-2 | ACEFGIKL |
| 875 | 1,4-Cineole | 470-67-7 | ADGIJKL |
| 880 | 1-(2,6,6-Trimethyl-2-cyclohexen-1-yl)-2-buten-1-one | 43052-87-5 | BDHIJK |
| 882 | (Z)-3-hepten-1-yl acetate | 1576-78-9 | ACEFHKL |
| 883 | (S)-(1R,5R)-4,6,6-trimethylbicyclo[3.1.1]hept-3-en-2-one | 1196-01-6 | ACEFGIJKL |
| 888 | (R)-(−)-Linalool | 126-91-0 | BCEFGIJK |
| 889 | (l)-Citronellal | 5949-05-3 | ACHIJKL |
| 891 | (d)-Citronellal | 2385-77-5 | ACHIJKL |
| 899 | (+)-Citronellol | 1117-61-9 | BCHIJKL |
| 900 | (−)-Citronellol | 7540-51-4 | BCHIJKL |
| 901 | (+)-alpha-Pinene | 7785-70-8 | ADEFGIJKL |
| 902 | (+)-Carvone | 2244-16-8 | ACGIJKL |
| 903 | (−)-alpha-Pinene | 7785-26-4 | ADEFGIJKL |
| 904 | Methyl 2-methylbutyrate | 868-57-5 | ACEFGIKL |
| 909 | Hexyl tiglate | 16930-96-4 | BDEFHJKL |
| 918 | Allyl 2-(cyclohexyloxy)acetate | 68901-15-5 | CHJK |
| 921 | 1,5-dimethylbicyclo[3.2.1]octan-8-one oxime | 75147-23-8 | CFHIJK |
| 931 | alpha-acetoxystyrene | 2206-94-2 | ACEFHIK |
| 940 | p-Cymene | 99-87-6 | ADGIJKL |
| 956 | Phenethyl formate | 104-62-1 | ACEFHK |
| 958 | Phenethyl isobutyrate | 103-48-0 | DHJK |
| 960 | Phenethyl tiglate | 55719-85-2 | DHJK |
| 971 | Phenylethyl methacrylate | 3683-12-3 | DHJK |
| 977 | p-Isopropylphenylacetaldehyde | 4395-92-0 | BDFHK |
| 981 | 1,2-dimethyl-3-(prop-1-en-2-yl)cyclopentan-1-ol | 72402-00-7 | BCEFGIJKL |
| 983 | p-Methoxyphenylacetone | 122-84-9 | BCEFHK |
| 986 | (2Z,5Z)-5,6,7-trimethylocta-2,5-dien-4-one | 358331-95-0 | ADHIJKL |
| 987 | p-Propyl anisole | 104-45-0 | ADEFHKL |
| 994 | p-t-butyl phenyl acetaldehyde | 109347-45-7 | BDHJK |
| 995 | p-tert-Amyl cyclohexanol | 5349-51-9 | BDEFGIJKL |
| 1001 | Racemic alpha-Pinene | 80-56-8 | ADEFGIJKL |
| 1002 | 4-(4-hydroxyphenyl)butan-2-one | 5471-51-2 | CEFGIK |
| 1004 | Rhodinol | 141-25-3 | BCHIJKL |
| 1005 | Ethyl (2,3,6-trimethylcyclohexyl) carbonate | 93981-50-1 | BDEFHJKL |
| 1011 | 1-(3,3-dimethylcyclohexyl)ethyl acetate | 25225-10-9 | ADHIJKL |
| 1017 | S)-(+)-Linalool | 126-90-9 | BCEFGIJK |
| 1018 | Sabinene | 3387-41-5 | ADEFGIJKL |
| 1019 | Sabinene hydrate | 546-79-2 | ADEFGIJKL |
| 1030 | Propyl (S)-2-(tert-pentyloxy)propanoate | 319002-92-1 | BDEFHJK |
| 1039 | Spirolide | 699-61-6 | BCGIKL |
| 1040 | (Z)-5-methylheptan-3-one oxime | 22457-23-4 | BCEFGIJKL |
| 1041 | 1-phenylethyl acetate | 93-92-5 | ACEFHIK |
| 1051 | Tetrahydrogeranial | 5988-91-0 | ADGIJKL |
| 1052 | Tetrahydroionol | 4361-23-3 | BDEFHIJK |
| 1054 | Tetrahydrolinalool | 78-69-3 | BDEFGIJKL |
| 1055 | Tetrahydrolinalyl acetate | 20780-48-7 | ADEFHJKL |
| 1058 | Ethyl (1R,6S)-2,2,6-trimethylcyclohexane-1-carboxylate | 22471-55-2 | ADEFHIJKL |
| 1061 | Thymol | 89-83-8 | BDHIJK |
| 1069 | trans-2-Hexenol | 928-95-0 | ACEFHIKL |
| 1071 | trans-2-tert-Butylcyclohexanol | 5448-22-6 | ACGIJKL |
| 1074 | trans-alpha-Damascone | 24720-09-0 | BDHIJK |
| 1076 | trans-Anethole | 4180-23-8 | ACEFHK |
| 1079 | trans-Cinnamic acid | 140-10-3 | CEFHK |
| 1081 | trans-Dihydrocarvone | 5948-04-9 | ACGIJKL |
| 1084 | trans-Isoeugenol | 5932-68-3 | CEFHIK |
| 1088 | Trichloromethyl phenyl carbinyl acetate | 90-17-5 | BDEFGJ |
| 1098 | 2-mercapto-2-methylpentan-1-ol | 258823-39-1 | ACEFHIJKL |
| 1110 | Vanillin acetate | 881-68-5 | CH |
| 1112 | Vanitrope | 94-86-0 | CEFHK |
| 1115 | 2,2,5-trimethyl-5-pentylcyclopentan-1-one | 65443-14-3 | BDFGIJKL |
| 1118 | Veratraldehyde | 120-14-9 | BCGIK |
| 1119 | (1R,5R)-4,6,6-trimethylbicyclo[3.1.1]hept-3-en-2-one | 18309-32-5 | ACEFGIJKL |
| 1122 | Verdol | 13491-79-7 | ACGIJKL |
| 1127 | 4-(tert-butyl)cyclohexyl acetate | 10411-92-4 | BDEFHJK |
| 1128 | 4-(tert-butyl)cyclohexyl acetate | 32210-23-4 | BDEFHJK |
| 1133 | Vethymine | 7193-87-5 | CEFGK |
| 1134 | 4-methyl-4-phenylpentan-2-yl acetate | 68083-58-9 | BDFHJK |
| 1141 | (Z)-1-((2-methylallyl)oxy)hex-3-ene | 292605-05-1 | ADEFHKL |

TABLE 4

List of materials with ALL MORVs from 1 to 5

| Number | Material Name | CAS Number | Comment Code |
|---|---|---|---|
| 7 | 3-methoxy-7,7-dimethyl-10-methylenebicyclo[4.3.1]decane | 216970-21-7 | BDEFHJK |
| 14 | Oxyoctaline formate | 65405-72-3 | DFHJK |
| 39 | 2,2,6,8-tetramethyl-1,2,3,4,4a,5,8,8a-octahydronaphthalen-1-ol | 103614-86-4 | DEFHJK |
| 48 | Nootkatone | 4674-50-4 | DHJK |
| 183 | Khusimol | 16223-63-5 | CEFHJK |
| 199 | Isopimpinellin | 482-27-9 | CFGJ |
| 206 | Iso3-methylcyclopentadecan-1-one | 3100-36-5 | DEFGJK |
| 212 | Isoeugenyl benzyl ether | 120-11-6 | DFHJ |
| 215 | 1-((2S,3S)-2,3,8,8-tetramethyl-1,2,3,4,5,6,7,8-octahydronaphthalen-2-yl)ethan-1-one | 54464-57-2 | DHJK |
| 229 | Isobornyl isobutyrate | 85586-67-0 | BDEFHJK |
| 260 | 2,3-dihydro-3,3-dimethyl-1H-indene-5-propanal | 173445-44-8 | DHJK |
| 261 | 3-(3,3-dimethyl-2,3-dihydro-1H-inden-5-yl)propanal | 173445-65-3 | DHJK |
| 281 | 3a,4,5,6,7,7a-hexahydro-1H-4,7-methanoinden-6-yl acetate | 5413-60-5 | CEFGJK |
| 329 | gamma-Eudesmol | 1209-71-8 | DFHJK |
| 335 | 4,6,6,7,8,8-hexamethyl-1,3,4,6,7,8-hexahydrocyclopenta[g]isochromene | 1222-05-5 | DEFHJK |
| 353 | (Z)-6-ethylideneoctahydro-2H-5,8-methanochromen-2-one | 69486-14-2 | CEFGJK |

TABLE 4-continued

List of materials with ALL MORVs from 1 to 5

| Number | Material Name | CAS Number | Comment Code |
|---|---|---|---|
| 360 | 8,8-dimethyl-3a,4,5,6,7,7a-hexahydro-1H-4,7-methanoinden-6-yl acetate | 171102-41-3 | DEFHJK |
| 441 | Octahydro-1H-4,7-methanoinden-5-yl acetate | 64001-15-6 | DEFHJKL |
| 484 | 3a,4,5,6,7,7a-hexahydro-1H-4,7-methanoinden-6-yl butyrate | 113889-23-9 | DEFHJK |
| 487 | 3a,4,5,6,7,7a-hexahydro-1H-4,7-methanoinden-5-yl isobutyrate | 67634-20-2 | DEFHJK |
| 488 | Curzerene | 17910-09-7 | DHJK |
| 501 | (E)-cycloheptadec-9-en-1-one | 542-46-1 | DEFGJ |
| 566 | Cedryl formate | 39900-38-4 | BDEFHJK |
| 567 | Cedryl acetate | 77-54-3 | DEFHJK |
| 569 | Cedrol | 77-53-2 | DEFHJK |
| 570 | 5-methyl-1-(2,2,3-trimethylcyclopent-3-en-1-yl)-6-oxabicyclo[3.2.1]octane | 139539-66-5 | DEFHJK |
| 573 | Caryophyllene alcohol acetate | 32214-91-8 | DEFHJK |
| 574 | Caryolan-1-ol | 472-97-9 | DEFHJK |
| 603 | Bornyl isobutyrate | 24717-86-0 | BDEFHIJK |
| 616 | beta-Santalol | 77-42-9 | DEFHJK |
| 621 | beta-Patchoulline | 514-51-2 | BDEFGJKL |
| 624 | beta-Himachalene Oxide | 57819-73-5 | BDFHJK |
| 627 | (2,2-dimethoxyethyl)benzene | 101-48-4 | DHJK |
| 632 | beta-Cedrene | 546-28-1 | BDEFGJKL |
| 663 | Anisyl phenylacetate | 102-17-0 | DFHJ |
| 680 | 2,2,6,6,7,8,8-heptamethyldecahydro-2H-indeno[4,5-b]furan | 647828-16-8 | ADEFHJK |
| 684 | alpha-Vetivone | 15764-04-2 | DHJK |
| 694 | alpha-Santalol | 115-71-9 | DEFHJK |
| 696 | alpha-Patchoulene | 560-32-7 | ADEFHJKL |
| 708 | alpha-Gurjunene | 489-40-7 | BDEFHJKL |
| 712 | alpha-Eudesmol | 473-16-5 | DEFHJK |
| 714 | alpha-Cubebene | 17699-14-8 | ADEFHJKL |
| 726 | alpha-Agarofuran | 5956-12-7 | BDEFHJK |
| 750 | Allo-aromadendrene | 25246-27-9 | BDEFHJKL |
| 764 | Acetarolle | 744266-61-3 | DFHJK |
| 775 | 7-eip-alpha-Eudesmol | 123123-38-6 | DEFHJK |
| 776 | 7-Acetyl-1,1,3,4,4,6-hexamethyltetralin | 1506-02-1 | DEFHJ |
| 788 | 5-Cyclohexadecenone | 37609-25-9 | DEFGJK |
| 804 | 3-Thujopsanone | 25966-79-4 | BDEFHJK |
| 872 | 10-epi-gamma-Eudesmol | 15051-81-7 | DFHJK |
| 919 | 3a,4,5,6,7,7a-hexahydro-1H-4,7-methanoinden-6-yl propionate | 17511-60-3 | CEFHJK |
| 927 | 5-Acetyl-1,1,2,3,3,6-hexamethylindan | 15323-35-0 | DEFHJK |
| 933 | Patchouli alcohol | 5986-55-0 | DEFHIJK |
| 978 | 3a,4,5,6,7,7a-hexahydro-1H-4,7-methanoinden-6-yl pivalate | 68039-44-1 | DEFHJK |
| 1007 | (2R,4a'R,8a'R)-3,7'-dimethyl-3',4',4a',5',8',8a-hexahydro-1'H-spiro[oxirane-2,2'-[1,4]methanonaphthalene] | 41816-03-9 | DEFHJK |
| 1022 | 2,2,7,9-tetramethylspiro(5.5)undec-8-en-1-one | 502847-01-0 | DHIJK |
| 1024 | (Z)-2-ethyl-4-(2,2,3-trimethylcyclopent-3-en-1-yl)but-2-en-1-ol | 28219-61-6 | DEFHJK |
| 1027 | 5-methoxyoctahydro-1H-4,7-methanoindene-2-carbaldehyde | 193425-86-4 | CHJK |
| 1029 | Sclareol oxide | 5153-92-4 | DEFHJK |
| 1035 | Spathulenol | 6750-60-3 | DEFHJK |
| 1038 | 1-(spiro[4.5]dec-7-en-7-yl)pent-4-en-1-one | 224031-70-3 | DGJK |
| 1060 | Thujopsene | 470-40-6 | BDEFGJKL |
| 1089 | Tricyclone | 68433-81-8 | DEFHJK |
| 1107 | Valerianol | 20489-45-6 | DEFHJK |
| 1129 | 1-((3R,3aR,7R,8aS)-3,6,8,8-tetramethyl-2,3,4,7,8,8a-hexahydro-1H-3a,7-methanoazulen-5-yl)ethan-1-one | 32388-55-9 | DHJK |
| 1131 | Methyl (Z)-2-(((2,4-dimethylcyclohex-3-en-1-yl)methylene)amino)benzoate | 68738-99-8 | DEFHJ |
| 1136 | Vetivert Acetate | 117-98-6 | DEFHJK |
| 1137 | Decahydro-3H-spiro[furan-2,5'-[4,7]methanoindene] | 68480-11-5 | DEFGJKL |
| 1140 | (1aR,4S,4aS,7R,7aS,7bS)-1,1,4,7-tetramethyldecahydro-1H-cyclopropa[e]azulen-4-ol | 552-02-3 | DEFHJK |
| 1142 | 3,5,5,6,7,8,8-heptamethyl-5,6,7,8-tetrahydronaphthalene-2-carbonitrile | 127459-79-4 | DHJ |
| 1143 | (1S,2S,3S,5R)-2,6,6-trimethylspiro[bicyclo[3.1.1]heptane-3,1'-cyclohexan]-2'-en-4'-one | 133636-82-5 | DEFHJK |
| 1144 | 1',1',5',5'-tetramethylhexahydro-2'H,5'H-spiro[[1,3]dioxolane-2,8'-[2,4a]methanonaphthalene] | 154171-76-3 | DEFHJK |
| 1145 | 1',1',5',5'-tetramethylhexahydro-2'H,5'H-spiro[[1,3]dioxolane-2,8'-[2,4a]methanonaphthalene] K | 154171-77-4 | DEFHJK |
| 1148 | 4,5-epoxy-4,11,11-trimethyl-8-methylenebicyclo(7.2.0)undecane | 1139-30-6 | DEFHJK |
| 1149 | 1,3,4,6,7,8alpha-hexahydro-1,1,5,5-tetramethyl-2H-2,4alpha-methanophtalen-8(5H)-one | 23787-90-8 | DEFHIJK |

TABLE 5

List of materials with ALL MORVs greater than 5 to 10

| Number | Material Name | CAS Number | Comment Code |
|---|---|---|---|
| 248 | Hydroxymethyl isolongifolene | 59056-64-3 | BDEFHJK |

TABLE 6

List of materials with ALL MORVs from 0.5 to less than 1

| Number | Material Name | CAS Number | Comment Code |
|---|---|---|---|
| 472 | Decyl anthranilate | 18189-07-6 | DEFHJ |
| 526 | (Z)-3-methyl-2-(pent-2-en-1-yl)cyclopent-2-en-1-one | 488-10-8 | BCHIJKL |

The materials in Tables 1-6 can be supplied by one or more of the following:
Firmenich Inc. of Plainsboro N.J. USA; International Flavor and Fragrance Inc. New York, N.Y. USA; Takasago Corp. Teterboro, N.J. USA; Symrise Inc. Teterboro, N.J. USA; Sigma-Aldrich/SAFC Inc. Carlsbad, Calif. USA; and Bedoukian Research Inc. Danbury, Conn. USA.
Actual MORV values for each material listed in Tables 1-6 above are as follows:

| Material No. | MORV value for Equation a.) | MORV Value for Equation b.) | MORV Value for Equation c.) | MORV value for Equation d.) |
|---|---|---|---|---|
| 1 | 0.548223914 | 0.876283261 | 1.22018588 | −0.41901144 |
| 2 | 1.520311929 | 3.493450446 | 2.70657265 | 5.11342862 |
| 3 | 2.267801995 | −0.81712657 | 0.43218875 | 1.595983683 |
| 4 | −0.591063369 | −0.48283571 | 0.16199804 | 1.210497701 |
| 7 | 1.437444636 | 2.131822996 | 3.81633465 | 1.318339345 |
| 9 | 2.151445882 | −0.46189495 | 0.56090469 | 1.206360803 |
| 10 | 2.5733592 | −0.58780849 | 1.39751471 | 1.258361951 |
| 11 | 3.052627325 | 1.008519135 | −0.30475953 | 0.076323462 |
| 12 | 0.683776599 | −0.01157903 | 0.82853231 | 0.326169402 |

-continued

| Material No. | MORV value for Equation a.) | MORV Value for Equation b.) | MORV Value for Equation c.) | MORV value for Equation d.) |
|---|---|---|---|---|
| 13 | 1.549643217 | 1.809183231 | 0.70864531 | 2.22799611 |
| 14 | 2.82111224 | 2.339505033 | 1.240818 | 2.502429355 |
| 16 | -0.31551128 | -0.06816599 | -0.04371934 | 2.76742389 |
| 17 | -1.334904153 | -0.5773313 | 1.75644798 | 1.898455724 |
| 18 | -1.34154226 | -2.63596666 | 0.06885109 | 1.001431671 |
| 19 | 0.15532384 | 0.09866097 | 0.64214585 | -0.33330779 |
| 20 | 0.640261783 | 0.693213268 | 0.54637273 | -0.97556029 |
| 21 | 0.936895364 | -0.01521118 | 1.1697513 | -0.63510809 |
| 22 | 1.158981042 | 1.115900089 | -0.25859776 | 1.318200884 |
| 23 | 3.702361074 | 1.399942641 | 5.23954766 | 7.089933671 |
| 24 | 0.773874141 | 0.146848137 | -1.05705847 | -0.36193173 |
| 25 | -1.016103969 | -1.18967936 | 0.78064625 | 2.944710012 |
| 25 | -1.016103969 | -1.18967936 | 0.78064625 | 2.944710012 |
| 26 | 0.615085491 | -0.00096877 | -0.35697252 | -0.18121401 |
| 27 | 0.70261974 | -0.22197386 | 0.19710806 | -2.37196477 |
| 28 | 1.366472597 | -0.42546942 | -0.59394241 | -0.01417395 |
| 29 | 1.096043453 | -1.02972898 | -1.42167356 | -0.63817943 |
| 30 | 1.143415203 | -0.85945441 | -0.41416913 | 2.499807942 |
| 31 | 1.138642907 | -0.19595476 | -0.54547769 | -0.98828898 |
| 32 | 1.914414495 | -0.64487788 | 0.63212987 | 1.166699371 |
| 33 | 0.314847366 | 1.848003955 | -1.3905032 | -0.62848261 |
| 34 | -0.113542761 | 0.981530917 | 0.32824239 | 1.126524277 |
| 35 | 0.472382903 | 1.494882467 | -0.07201236 | -0.64589543 |
| 36 | 3.158513795 | 1.084094934 | -0.00328981 | -0.17786385 |
| 37 | -1.055631982 | 2.240172964 | 0.92596118 | 2.105391988 |
| 38 | 3.158513795 | 0.592820874 | -0.49326241 | 0.212867212 |
| 39 | 1.083800659 | 2.069727985 | 2.48170879 | 3.205630609 |
| 42 | -0.103134861 | 0.267726008 | -0.65350189 | 1.125952363 |
| 43 | 0.323961628 | 1.469295081 | -0.52991193 | 0.797908251 |
| 47 | 1.703678841 | 1.348737095 | 2.00634162 | -0.16505407 |
| 48 | 2.370955056 | 2.783472865 | 2.68240273 | 1.221864405 |
| 49 | 1.670680003 | -0.41866107 | -0.9173849 | 1.181929544 |
| 50 | 1.670680003 | 0.076369374 | -0.49915943 | -0.85392575 |
| 52 | 0.464485039 | 0.057512685 | 1.31230219 | -0.11170276 |
| 53 | 0.626671823 | -0.46954947 | -0.33383736 | 0.277079201 |
| 54 | 0.666149043 | 0.009549925 | -0.36226343 | 0.197224432 |
| 55 | 0.723473579 | -1.50916383 | -0.3848989 | -0.71458778 |
| 57 | 0.381273227 | 1.192994109 | 1.65593321 | -1.65739236 |
| 59 | 0.561360663 | -0.17793966 | -1.63250554 | -0.7564969 |
| 61 | 0.146473611 | -0.01535544 | -0.16339658 | 1.738656146 |
| 62 | 1.20162032 | -0.3576095 | -0.10695443 | 1.322155191 |
| 63 | 1.084291915 | 2.258720158 | -1.01245416 | 1.688283974 |
| 64 | 0.744770665 | 0.155243763 | -1.8029919 | 1.023503542 |
| 65 | 0.972835178 | 2.797151284 | 1.53453579 | 0.857051645 |
| 67 | 2.069410561 | 0.021831924 | 0.37855159 | -0.67235457 |
| 68 | 0.527636614 | 0.590831983 | 1.02843762 | 2.208655795 |
| 69 | 2.133965691 | 2.088998449 | 2.05751412 | -0.9433713 |
| 70 | 0.327378959 | 0.996844599 | 1.23648533 | -1.25138371 |
| 71 | 1.40093669 | 0.778222691 | 0.70401172 | -0.24075444 |
| 72 | 0.617697349 | -0.29503359 | 0.52404847 | 0.816184656 |
| 73 | 0.617792473 | 0.888976061 | -0.45289639 | 0.615659244 |
| 74 | 1.437359024 | 1.548292147 | 0.10314807 | -0.48982286 |
| 75 | -1.970885622 | 3.398008325 | 4.08025266 | -0.89948156 |
| 76 | -1.32746934 | -2.65365233 | 0.10272816 | 1.001614125 |
| 77 | -2.541686116 | 3.295534192 | 3.75284227 | 0.404837808 |
| 78 | -2.110794 | 2.109874746 | 3.13350902 | -0.3880285 |
| 79 | 1.641162056 | -0.28533994 | 1.53676145 | 0.652696023 |
| 80 | 1.594400214 | 0.283682865 | 2.23140233 | 1.111682021 |
| 81 | 0.176566806 | -2.0786516 | -2.13986952 | 0.981126964 |
| 82 | 0.980373758 | -0.28813159 | 0.19404501 | 1.252564677 |
| 83 | 0.941833098 | 0.317310013 | 1.17606727 | 0.72992237 |
| 84 | 0.774237336 | -0.27140727 | 0.72461427 | -1.56415746 |
| 85 | 2.092976965 | 0.810644229 | 0.82999192 | -0.62861806 |
| 91 | 2.061595915 | -0.79930338 | -0.18285395 | -0.66898499 |
| 92 | 2.068748434 | -0.24299896 | 0.07214682 | -1.11758276 |
| 93 | -0.08984279 | -1.06025959 | -0.05068694 | 1.560050105 |
| 96 | 0.927758203 | -0.44129515 | 0.89190422 | 0.744284978 |
| 97 | 0.658667572 | -0.68771072 | 0.46051026 | -0.53120883 |
| 98 | 0.853222693 | -0.2037738 | -0.21414441 | 1.119784962 |
| 100 | 1.654535066 | 0.995056228 | 2.35139085 | 0.543654824 |
| 101 | 2.173663649 | -0.11491477 | 1.48285148 | 1.698527571 |
| 102 | 2.066679492 | -0.16785146 | -0.84780149 | 0.12159477 |
| 103 | 2.335152618 | -0.02866585 | 0.16993375 | -0.98254522 |
| 104 | 2.760588276 | 0.459513599 | 1.35310241 | 0.000336976 |
| 105 | 1.654535066 | 3.654489674 | 3.13033965 | 0.544225478 |
| 106 | 1.750588169 | -0.55853348 | 0.50257773 | 1.630011313 |
| 107 | 0.896789863 | 0.73615897 | 0.53011623 | -0.54697747 |
| 108 | 0.532375207 | 0.826537134 | 1.21040312 | 0.690230716 |
| 109 | 2.407655187 | 0.742651426 | 1.80322099 | 0.271832856 |
| 110 | 0.54830833 | 2.916795026 | 1.40126098 | 0.690230716 |
| 111 | 0.939597126 | -0.3750368 | -1.23479972 | -0.89366351 |
| 112 | 1.398518854 | 1.265740274 | 4.19618377 | -0.12762692 |
| 113 | 1.415726941 | 0.086297006 | 3.43559555 | -0.12964168 |
| 115 | -1.557729423 | -0.44113526 | 0.86330536 | 0.590708892 |
| 116 | 0.193562268 | -1.58091165 | 0.83247813 | -0.70978039 |
| 117 | 1.353510875 | -0.59062398 | -0.31776345 | -0.3050158 |
| 119 | 0.830052725 | 2.28725579 | 0.38409695 | 0.219336109 |
| 120 | 1.261997955 | -0.22622961 | -1.04772194 | 2.028504137 |
| 122 | 1.505653628 | -1.14748206 | -0.19760084 | -0.81373045 |
| 123 | -0.658721962 | -0.21299878 | 1.01439841 | -0.76731016 |
| 125 | 0.749676998 | -1.0761601 | 0.99563924 | -1.15409002 |
| 126 | 0.931054384 | -0.35067079 | 1.06050832 | -1.62171794 |
| 128 | -1.344832644 | -0.09451199 | 1.19145467 | 1.621274257 |
| 130 | 1.153249538 | 1.605070708 | 2.38047907 | -0.93842293 |
| 133 | 0.840066046 | 0.2323025 | 0.19054023 | -0.26588341 |
| 134 | 0.522267541 | 0.824106618 | 1.83479545 | 0.364403434 |
| 135 | 2.142817887 | 2.142411243 | -0.93830995 | 0.696522652 |
| 137 | 3.052627325 | 3.606270166 | 0.50445208 | 0.076323462 |
| 140 | -0.153437637 | 0.246303216 | 0.76565758 | 1.800968868 |
| 141 | 2.067620311 | 1.424830396 | 2.33536931 | 7.644025075 |
| 142 | 0.98353103 | 1.950251373 | 2.50851828 | -0.24499521 |
| 143 | 1.736969725 | 0.991537809 | 2.5691601 | 1.227191656 |
| 145 | -0.211768579 | 1.46336231 | -0.93580247 | -1.48749449 |
| 146 | 1.912710035 | 0.926306508 | 1.81253333 | 0.494121361 |
| 147 | 0.675736303 | 0.99202385 | -0.66034472 | -0.66302659 |
| 148 | 0.757176542 | 1.83006252 | 0.16210659 | 0.243674851 |
| 149 | 0.438772371 | 1.091438092 | -0.1560319 | -0.61711642 |
| 150 | 0.84399938 | 0.675302022 | -1.69771411 | -0.73841711 |
| 151 | 0.633570539 | 0.988413715 | -0.54991825 | -0.43550324 |
| 152 | 0.911582356 | 1.974700218 | -0.92267786 | 0.628660087 |
| 153 | 0.319053885 | 2.531735341 | -0.39139184 | 0.734629224 |
| 154 | 0.714814512 | 0.690769753 | -2.06588692 | -0.73356628 |
| 155 | -0.161798388 | 0.032135767 | -0.13802086 | 1.734928461 |
| 156 | -0.571799976 | -1.32834264 | -1.65346017 | 1.856689553 |
| 157 | 0.131224024 | 0.21510779 | -1.70996346 | 0.964902175 |
| 158 | 1.201616145 | -0.21158932 | -0.8501176 | -0.33330779 |
| 159 | 0.811289908 | 1.606645397 | 0.25352447 | -1.83775117 |
| 159 | 0.811289908 | 1.606645397 | 0.25352447 | -1.83775117 |
| 161 | 0.475184006 | 1.99305646 | 1.90910177 | 3.288337059 |
| 162 | 0.833030517 | 0.487189028 | 1.76798642 | 0.104378164 |
| 163 | 0.58993703 | -0.46431772 | 0.74883588 | -0.81090824 |
| 166 | -0.121286831 | -0.84664528 | -0.32625341 | 0.778055656 |
| 167 | 0.846400186 | -0.25922232 | 0.69248774 | 1.183696217 |
| 168 | -0.310930833 | -0.81048493 | 0.08527131 | 1.61831109 |
| 169 | -0.2346025 | 0.890438419 | -0.13206526 | -0.83961838 |
| 170 | -0.169223695 | 1.172917966 | -0.11306441 | 0.099121666 |
| 174 | 2.863652137 | 0.236674094 | -0.69038707 | 1.610215283 |
| 175 | 1.789769228 | -0.31740428 | -0.89529921 | -0.09686469 |
| 176 | 2.625947334 | 0.083548191 | 0.30634559 | -0.35925728 |
| 177 | 1.674319352 | -0.22179044 | 0.42093738 | -0.23683577 |
| 178 | 2.863652137 | 0.727069168 | -0.26724686 | -0.44888613 |
| 179 | 0.070511885 | 0.365852864 | 1.35327505 | -0.03748038 |
| 181 | 0.976254543 | 0.691638796 | 0.51371978 | -0.02503945 |
| 182 | -1.842503751 | -0.12688474 | 2.56277877 | 0.111744488 |
| 183 | 3.195758563 | 3.886545621 | 4.29482769 | 3.829845293 |
| 184 | 0.333889534 | -0.67236766 | 2.21605977 | 4.254612125 |
| 185 | 5.61162203 | 1.40458529 | 2.86231343 | 1.035135749 |
| 186 | 1.068190511 | -0.65969343 | -0.63104765 | -1.36962992 |
| 187 | 1.396358739 | 0.249705611 | 0.81449499 | -0.15353102 |
| 189 | 1.544466636 | -0.33742685 | 0.8096674 | -0.44483677 |
| 190 | -0.210918777 | -1.04086063 | 0.02614862 | 3.362615492 |
| 191 | 0.715897301 | 0.666316436 | -0.41719538 | 0.400723176 |
| 192 | 0.65612864 | 1.231196814 | 0.75462061 | 1.514581532 |
| 193 | -0.394884432 | 1.129269425 | -0.3157071 | -0.61478944 |
| 194 | -2.111794245 | -0.71010521 | 0.53077207 | 0.59302222 |
| 195 | 1.18880856 | 0.704463775 | 1.99312777 | 1.419709023 |
| 196 | 1.885714606 | 0.436434665 | 1.44657532 | 1.145809063 |
| 197 | 2.174580668 | 0.133070149 | 0.99814905 | 0.871658496 |
| 198 | -0.533922573 | -2.16213117 | 0.5812107 | -0.92280453 |
| 199 | 1.493919434 | 1.45125612 | 1.95141371 | 4.403441058 |

| Material No. | MORV value for Equation a.) | MORV Value for Equation b.) | MORV Value for Equation c.) | MORV value for Equation d.) | Material No. | MORV value for Equation a.) | MORV Value for Equation b.) | MORV Value for Equation c.) | MORV value for Equation d.) |
|---|---|---|---|---|---|---|---|---|---|
| 201 | −0.005520296 | −0.83362523 | 0.65480762 | −0.38894276 | 306 | 0.561360663 | −0.17793966 | −1.63250554 | −0.7564969 |
| 204 | 0.732981164 | −0.97494758 | −0.91192246 | −1.00034323 | 307 | 1.583243229 | 1.398558046 | 0.152423 | −0.13988304 |
| 205 | 0.991838899 | −0.60053505 | −0.49983634 | 0.674468753 | 308 | −0.067380931 | 0.74278658 | 0.29217479 | 0.180866298 |
| 206 | 2.147983695 | 1.291351958 | 1.64553247 | 1.626455601 | 310 | 0.238202662 | 0.926241567 | −0.66649303 | 0.508184193 |
| 208 | −0.386224123 | −0.24799559 | 1.19406353 | −1.61243489 | 312 | 0.714965519 | −0.45511207 | −2.34849436 | −0.9953911 |
| 209 | 1.447075297 | 0.122626462 | 1.08021156 | 0.473154634 | 314 | 0.736369931 | −0.52068396 | 0.53882253 | −0.7059813 |
| 210 | −0.386224123 | −0.24799559 | 1.19406353 | −1.61243489 | 316 | 2.314558863 | −0.25458611 | 0.22080129 | −0.04142716 |
| 211 | 2.186118467 | 1.873949371 | 0.64852028 | −0.59205851 | 317 | 1.095005005 | 0.057439852 | −1.20728654 | 0.035895107 |
| 212 | 1.367811201 | 1.689658923 | 1.8017376 | 2.525531645 | 318 | −0.111714595 | −0.61079351 | −1.16010053 | 1.102488007 |
| 213 | 0.925016223 | 0.875610609 | 0.31462609 | 0.847028648 | 319 | −0.264829849 | 0.540388888 | 0.10729709 | −0.57215449 |
| 214 | −0.239873321 | 1.808823425 | −0.36105512 | −0.07650286 | 321 | 1.243861203 | −0.75229123 | 0.05515858 | −0.34659253 |
| 215 | 2.264275088 | 1.360001278 | 3.25759951 | 2.147928282 | 322 | 0.956379568 | 2.838565742 | 2.7997689 | 0.805938034 |
| 218 | −0.509585598 | −0.93428643 | 1.63030386 | −0.79436377 | 323 | 1.884902746 | 0.813499245 | 0.86344403 | −0.1241887 |
| 221 | 1.876297063 | 0.026873469 | 0.45442758 | 1.538486988 | 324 | 0.189037208 | 1.105600415 | 0.48460989 | 0.285938173 |
| 227 | 5.317676982 | 2.824566654 | 1.73360625 | 3.103310061 | 325 | 0.791400443 | 2.454239197 | 1.54315324 | 1.416449646 |
| 228 | 3.323728685 | 1.554268023 | 1.8883835 | 0.957527434 | 328 | 1.22836182 | 2.190068443 | 2.48751772 | 0.126982574 |
| 229 | 3.218950175 | 1.464118271 | 2.47512497 | 1.214429025 | 329 | 1.800767509 | 1.372656013 | 2.09551175 | 2.849728342 |
| 230 | 5.242356467 | 3.482206715 | 3.50441556 | 1.614847073 | 330 | 2.688999059 | 0.017422444 | 0.34929031 | 0.108155361 |
| 230 | 5.242356467 | 3.482206715 | 3.50441556 | 1.614847073 | 331 | −0.223648429 | 0.873635097 | 1.78683863 | 0.126324441 |
| 231 | 2.710087358 | 1.517756148 | 0.35088855 | 0.603171932 | 332 | 1.884902746 | −0.46695445 | 0.1761545 | −0.11026722 |
| 231 | 2.710087358 | 1.517756148 | 0.35088855 | 0.603171932 | 333 | 0.956379568 | 2.838565742 | 2.7997689 | 0.805938034 |
| 232 | 0.703604481 | 0.42129186 | 0.39567696 | 0.41729786 | 334 | 0.569368001 | 2.811464091 | 1.88866785 | −0.16122533 |
| 233 | 1.312921486 | 0.816597603 | 2.17066283 | 0.472801294 | 335 | 1.931053264 | 2.306571877 | 4.45651797 | 4.474221307 |
| 234 | 0.874145958 | 0.741410502 | 1.71105733 | −0.47289415 | 336 | 1.355107839 | −0.49142588 | 0.83879083 | 0.18350392 |
| 237 | 0.778921491 | −1.02119303 | 0.4612164 | −0.8881184 | 338 | 1.025467157 | −0.99345477 | 0.57780149 | −0.19101275 |
| 238 | 0.681403734 | −0.342052 | 1.27750286 | −0.3383341 | 339 | 1.216559787 | −0.68632827 | 0.71921804 | 0.140021721 |
| 239 | −0.870637933 | −2.58292907 | 0.79173772 | −1.27888846 | 342 | 2.073599715 | −0.19777074 | −0.44964804 | −0.71885866 |
| 242 | 0.910211214 | 0.374558101 | 1.01712685 | 1.001043471 | 343 | 3.375840967 | 3.294907583 | 5.0378352 | 4.14804591 |
| 243 | 1.670680003 | 0.104780951 | −0.6545574 | −0.46985154 | 344 | 0.926453735 | 1.336260845 | 2.20088072 | 0.226359561 |
| 244 | 1.140332181 | 0.116513028 | 1.61110902 | 3.713305291 | 346 | −0.133453542 | −0.27276578 | 0.95852923 | −0.88404805 |
| 246 | −0.634992987 | 0.548746912 | 4.62542427 | 7.660969857 | 347 | −0.414858428 | −0.94736055 | 1.9452074 | −1.32753709 |
| 247 | −1.739729444 | −0.91508372 | 1.18693162 | 3.108631198 | 349 | 0.011110326 | 0.415952358 | 1.08076289 | 2.638925816 |
| 248 | 5.81821686 | 6.320330665 | 6.14379552 | 5.214046447 | 350 | −1.366284701 | −1.3912958 | −0.0683659 | 1.205395618 |
| 249 | 0.348188924 | −0.95333461 | −0.08432225 | 1.866717393 | 352 | 2.592229701 | 2.014162407 | −0.56599991 | −0.19676404 |
| 252 | 2.456287983 | −0.02516176 | 0.76814124 | 1.756087132 | 353 | 2.347680291 | 1.432589328 | 3.81650185 | 2.28664738 |
| 253 | 1.76915226 | 0.226389981 | −0.18115009 | −0.62385199 | 354 | −0.094599823 | 0.704257624 | 0.8494127 | −0.05632553 |
| 254 | 0.658956861 | −0.39322197 | −0.67153044 | 1.416053304 | 355 | −0.534528735 | −0.26820008 | 0.69328667 | 0.63557685 |
| 255 | 0.892122738 | −0.46985097 | 0.42813903 | −0.46752753 | 356 | 0.71431796 | 0.568464069 | 1.14931631 | 0.32594963 |
| 256 | 0.625043963 | −0.65111806 | 1.4319541 | 2.110656697 | 358 | 1.637857828 | 1.932629993 | 0.68535871 | −1.06298692 |
| 258 | −0.187789327 | −0.85870492 | −0.21766971 | 0.931521178 | 359 | 3.169264285 | 2.326146291 | 5.44251947 | 3.621423972 |
| 259 | −1.261365139 | −2.33099427 | 1.33595129 | 0.43644676 | 360 | 2.824830639 | 3.29829616 | 3.43870859 | 3.771256974 |
| 260 | 2.4020693 | 2.669351733 | 2.36395771 | 1.910609499 | 361 | 0.772183137 | 0.62924397 | 1.14549597 | 0.743423792 |
| 261 | 1.978618006 | 2.732613301 | 2.19594212 | 1.683156407 | 362 | 2.158106604 | −0.08901432 | 0.85035629 | −0.37323677 |
| 263 | 1.350274014 | −0.59210334 | 0.14780643 | −0.13113746 | 363 | 1.485114303 | −0.85819594 | 0.70929196 | 4.132013298 |
| 264 | 0.526085484 | −1.54983116 | −0.17497208 | −0.8204696 | 364 | −0.661168364 | −0.30270875 | 2.49237859 | −0.7675819 |
| 267 | 1.175997006 | −1.03507906 | −0.11004734 | −0.50564806 | 365 | −0.518303431 | −2.08665423 | 0.5658944 | −1.10451499 |
| 269 | 2.367197222 | 0.457286256 | 0.02211231 | 0.497925297 | 366 | −0.501301831 | 0.561788544 | 0.14113617 | 0.610082057 |
| 270 | 0.711734628 | −1.45058685 | −0.17018094 | −0.71795736 | 368 | −0.106125097 | 1.092782715 | −0.89571841 | −0.08594454 |
| 271 | 1.073564668 | −0.47951936 | −0.80269361 | 0.136837431 | 369 | 1.43532227 | 1.656262941 | −1.09448841 | 1.674272267 |
| 273 | 0.663835001 | −1.5674675 | 0.28509522 | −1.12959038 | 370 | 1.064083705 | −1.08482967 | 0.35640283 | 0.866246621 |
| 274 | 1.628173498 | −0.58892922 | −0.3892777 | −0.66728139 | 371 | 1.933819902 | 0.975863726 | 1.62799441 | 1.492919426 |
| 275 | 0.935336765 | −0.9522644 | −0.87000279 | −0.29365972 | 372 | 1.933819902 | 0.975863726 | 1.62799441 | 1.492919426 |
| 276 | −5.989155804 | 1.722071272 | 3.31094703 | 1.273171428 | 373 | 0.274120553 | 2.246646022 | 2.93946992 | 2.617412085 |
| 277 | 0.904631703 | −1.02628534 | 0.49274649 | 1.000655271 | 374 | 0.940949346 | 2.935858163 | 0.52084392 | 0.847114052 |
| 278 | 0.293923493 | −0.82335619 | 0.13147975 | 2.730914048 | 375 | 0.177236108 | 2.745061961 | 0.76268843 | 0.373809692 |
| 280 | −0.284822555 | 0.322094188 | 3.2184015 | 0.383213731 | 376 | −0.999571921 | 0.579320229 | −0.06019938 | −0.94280945 |
| 281 | 2.201373139 | 2.228820089 | 2.03455575 | 1.720697243 | 377 | 0.521811983 | −0.8476641 | 0.7732327 | 1.729406547 |
| 282 | 0.505189899 | −1.01844885 | −0.98499144 | 0.912195522 | 378 | −0.532701772 | −2.17823188 | 1.26760147 | 0.815211357 |
| 283 | 0.775002479 | −1.29876341 | −1.52162214 | −0.77292581 | 379 | −0.684994963 | 0.018353057 | −0.8170018 | 0.582030709 |
| 284 | 0.505189899 | −0.57830662 | −0.55673047 | −1.09870665 | 381 | 1.592237677 | 1.373054134 | 0.60184939 | −0.30300485 |
| 285 | −0.987611415 | 0.908212704 | 2.59089199 | 1.311154128 | 385 | 0.967501839 | 0.136172137 | 1.3645564 | 0.374341215 |
| 286 | −2.635687733 | −1.53554173 | 0.68132558 | 4.350511118 | 385 | 0.967501839 | 0.136172137 | 1.3645564 | 0.374341215 |
| 287 | −1.890800496 | −0.9175912 | −0.84177071 | 0.615422874 | 386 | 1.247138794 | −0.97883463 | 0.03688288 | −0.57321578 |
| 288 | −0.417807714 | −0.27643667 | 1.06515025 | 0.958812195 | 387 | 0.785485559 | −1.23629818 | −0.07759084 | −0.71795736 |
| 289 | 1.078763544 | 0.263281029 | 1.00763749 | 0.866949263 | 388 | 1.503632155 | −0.13455265 | 0.86630165 | 0.102845335 |
| 290 | 0.733561298 | −0.47493387 | 0.17088582 | 1.536463653 | 388 | 1.503632155 | −0.13455265 | 0.86630165 | 0.102845335 |
| 292 | 1.2252731 | 0.720498276 | 4.33362953 | 2.202084022 | 390 | 0.811363694 | 0.872605919 | −0.17445198 | 1.358866557 |
| 293 | 0.947860369 | 0.93449449 | 1.85056304 | 0.355024738 | 391 | 1.653006495 | −0.44095837 | 0.46475017 | −0.16817306 |
| 294 | −1.051634009 | 0.136579632 | 2.17918871 | −0.01949057 | 394 | 1.043989895 | −0.82625074 | 0.40893134 | −0.10417542 |
| 295 | 1.039790111 | 0.81471915 | −0.94326824 | 0.887662055 | 397 | 1.430046723 | −0.79407262 | 0.15684862 | −0.4384699 |
| 296 | 1.009509413 | 1.364418947 | 1.42805339 | 0.429992055 | 398 | −1.401723491 | 0.271079592 | 1.35530191 | −0.63550333 |
| 300 | 0.246930208 | 1.113809101 | 0.25540773 | 0.528760053 | 400 | 0.762211626 | −1.06778628 | −0.93642574 | −0.13193338 |
| 301 | 0.246930208 | 1.113809101 | 0.25540773 | 0.528760053 | 407 | 0.591198428 | −0.8943503 | 1.41392426 | 2.694863328 |
| 302 | 0.697198045 | −0.41500676 | −2.35076003 | −0.60639529 | 412 | −0.067309295 | −0.21963004 | 0.57788677 | −1.22740398 |
| 303 | 0.10667178 | 3.580489288 | 0.25893587 | 2.329367856 | 413 | 0.630456164 | 1.538096427 | 2.10994563 | 2.45668637 |

-continued

| Material No. | MORV value for Equation a.) | MORV Value for Equation b.) | MORV Value for Equation c.) | MORV value for Equation d.) |
|---|---|---|---|---|
| 414 | 0.460631327 | 3.678501689 | 1.18326431 | 1.28320952 |
| 415 | 0.060485009 | −1.37776759 | −0.22689728 | 2.328813337 |
| 416 | 1.864088631 | 0.2451067 | 1.63260125 | 1.855346924 |
| 417 | −0.747017264 | −2.60335412 | 0.85092701 | 3.525229717 |
| 418 | 3.678359573 | 3.437930194 | 4.42449746 | 0.716864637 |
| 419 | −0.131519393 | 0.731836014 | 0.81604919 | −1.29993979 |
| 420 | 0.11276779 | −0.13029453 | 0.19422843 | 0.853490939 |
| 421 | 2.819997124 | 0.193567405 | 1.15903162 | 1.748390255 |
| 424 | −0.211768579 | 1.46336231 | −0.93580247 | −1.48749449 |
| 425 | −1.467980751 | −2.41196874 | −0.34454968 | 2.161517022 |
| 426 | 2.176374648 | 2.131594325 | 1.99252316 | 0.002774099 |
| 428 | 2.10568799 | 0.336366154 | −1.41176883 | 0.827982605 |
| 429 | 2.179080731 | 0.811454228 | −0.58304782 | 0.827982605 |
| 432 | 0.814675557 | −0.13076033 | 1.07380397 | −0.01560954 |
| 436 | 0.003614069 | −0.4704298 | 1.6004974 | −1.27605297 |
| 437 | −0.070955783 | −0.17246926 | 0.32599434 | 0.682083059 |
| 438 | 0.71141055 | −0.62729405 | 0.6220964 | 0.498836975 |
| 439 | −2.152188932 | −1.81662702 | 0.66042162 | −1.57001886 |
| 440 | 0.194444196 | 0.880854446 | 0.80016905 | 0.373809692 |
| 441 | 2.349282571 | 1.734747324 | 1.71148239 | 1.274963632 |
| 442 | 0.243841724 | 0.036287037 | 0.51243015 | 0.361825534 |
| 443 | −0.131519393 | 0.731836014 | 0.81604919 | −1.29993979 |
| 444 | 0.607958335 | 1.910541857 | −0.42710132 | −0.46909656 |
| 445 | −0.047486491 | 1.045012945 | −0.25220201 | −0.31982826 |
| 447 | 0.611981677 | 0.559261438 | −0.31210071 | −2.20421695 |
| 448 | 0.45491409 | 0.804084437 | 0.03088748 | −0.17549737 |
| 449 | 0.323968221 | −1.00428076 | −1.65151616 | 1.031096548 |
| 450 | 1.433196296 | −0.12277841 | 3.46809784 | −0.14760118 |
| 453 | 1.138642907 | 0.238344138 | −0.56453732 | −0.60639529 |
| 454 | 0.689556954 | −0.32116049 | 0.17614165 | 0.99165159 |
| 455 | −0.978653338 | −0.96381951 | 0.37950282 | 0.793341469 |
| 457 | 2.740852074 | 1.146976436 | 0.01429902 | 0.909817098 |
| 459 | 2.034203389 | −0.06483391 | 0.25864307 | 0.096715771 |
| 461 | 0.405441454 | 3.029508918 | 1.66201629 | 0.621375526 |
| 462 | 1.348588872 | 2.252065606 | 1.98535615 | 0.126982574 |
| 463 | 2.402548765 | 0.141297665 | 0.32401564 | 0.165555831 |
| 464 | 1.396358739 | −0.35292634 | 0.11760582 | −0.13960954 |
| 465 | 0.940569103 | 1.267891616 | 1.68420132 | 1.263608034 |
| 466 | −0.191220659 | 0.067062979 | 2.24237992 | 0.125280183 |
| 467 | 0.940569103 | 1.267891616 | 1.68420132 | 1.263608034 |
| 468 | 0.123370943 | 1.164309475 | 0.17099727 | −0.95446701 |
| 469 | 0.925252053 | −0.57178441 | 0.69807561 | −0.59133195 |
| 470 | 2.237616041 | 1.810156128 | −0.58140154 | 1.320304914 |
| 471 | 1.714516544 | −0.62135116 | 0.23636624 | −0.2706853 |
| 472 | 0.605628283 | 0.938001104 | 0.50028363 | 0.743911872 |
| 473 | 0.093847515 | −1.1973016 | −0.26960381 | 1.829684619 |
| 474 | 0.696773849 | 1.065592689 | 0.37607733 | −0.19241493 |
| 475 | 1.405352842 | 0.379589036 | 0.27781476 | 0.041425889 |
| 477 | 0.237582954 | 0.629327199 | 0.45159895 | −1.59912382 |
| 478 | 1.360648836 | 0.598053217 | 2.00883441 | −0.0827715 |
| 479 | 2.214928637 | −0.24358938 | −0.3486103 | 0.9190125 |
| 480 | 1.933819902 | −0.3826187 | 0.97439148 | 1.491603428 |
| 480 | 1.933819902 | −0.3826187 | 0.97439148 | 1.491603428 |
| 481 | 0.612364301 | −0.26364231 | −1.3201026 | −1.62884377 |
| 482 | 1.604448424 | 1.286308964 | −0.34289284 | 0.887781648 |
| 482 | 1.604448424 | 1.286308964 | −0.34289284 | 0.887781648 |
| 484 | 3.269313083 | 2.336715633 | 3.65534824 | 2.158890088 |
| 486 | 1.530484593 | 1.052491466 | 3.11297562 | 0.430146348 |
| 487 | 2.889323404 | 2.226094104 | 4.12877699 | 2.184426542 |
| 488 | 1.062548487 | 4.75312035 | 2.78435853 | 2.01925207 |
| 491 | 0.397432667 | −0.20071274 | 0.842202 | 1.944142408 |
| 493 | 0.270731661 | −0.7406408 | −1.17192239 | 1.401933582 |
| 495 | 0.298981649 | 0.854414067 | −2.2714622 | −0.62848261 |
| 496 | 0.565278409 | 0.659352661 | −0.00159534 | 0.384991859 |
| 497 | 2.972647554 | 1.210988046 | 0.08629653 | 0.991649406 |
| 498 | 2.863652137 | 0.229707592 | −0.75515466 | −0.06022029 |
| 502 | 0.478208715 | 1.827989577 | 0.67676345 | −0.88328385 |
| 503 | 0.845706083 | 1.117392544 | −0.21773539 | 0.272770415 |
| 504 | 0.837488879 | 0.874463134 | −0.08311625 | 0.149327397 |
| 505 | 1.749446006 | 0.076054765 | −0.59137073 | 0.291488011 |
| 509 | 0.716903285 | −0.22917288 | −1.93027881 | −1.52173529 |
| 510 | 0.241638743 | 0.769444787 | −0.07283731 | −0.38771737 |
| 512 | 0.556069536 | −0.47514685 | −1.88388474 | −1.67297277 |
| 515 | 0.23291131 | 0.598998195 | −0.99553291 | −0.40829542 |
| 517 | 0.784181146 | −0.20530019 | −1.89414748 | 0.152726109 |
| 518 | 0.742030255 | 0.281479436 | −1.4156326 | −1.91369695 |
| 519 | 0.367442761 | −0.50911405 | −0.77651804 | 3.081125259 |
| 520 | 1.28335174 | −0.16976166 | 0.19676128 | 1.493753388 |
| 521 | −1.105672292 | −1.29204085 | −0.95149628 | 1.817322011 |
| 522 | 0.714965519 | −0.45511207 | −2.34849436 | −0.9953911 |
| 524 | 0.325255266 | 1.131242708 | −2.79377204 | −0.62848261 |
| 525 | −0.210625832 | 0.979060885 | 0.37926876 | −2.08002977 |
| 526 | 0.698504484 | 0.548193178 | 0.92265651 | 0.500152973 |
| 527 | 0.420012766 | 1.731459464 | −0.23341719 | 0.139565409 |
| 528 | 0.161304111 | 0.66712144 | 0.58401752 | 0.373809692 |
| 529 | 0.911890585 | 0.353572744 | 1.04706167 | 1.001090055 |
| 530 | 1.670680003 | 0.86138741 | −0.27652639 | 1.174059185 |
| 531 | −0.169223695 | 1.172917966 | −0.11306441 | 0.099121666 |
| 532 | 2.237616041 | 1.438074134 | 0.31117554 | −0.71786492 |
| 534 | 1.205873658 | 1.32208026 | 1.21816392 | −0.5027271 |
| 535 | 0.999469738 | 0.056406435 | 0.72382479 | −0.61170287 |
| 536 | 0.63876931 | −0.39111525 | 0.08747854 | −0.66833729 |
| 537 | 0.689953348 | 1.206425159 | 0.58870271 | 0.198159994 |
| 538 | 0.54988634 | −0.32842011 | 0.69258273 | −0.81953404 |
| 540 | 0.735538933 | −0.20826876 | 0.6955468 | −0.7170218 |
| 541 | 1.097368973 | 0.740159871 | 0.12012053 | 0.137772993 |
| 542 | −0.24632881 | −0.09354384 | −0.13580399 | 0.599029186 |
| 544 | 0.687639306 | −0.30861817 | 1.14537443 | −1.12865481 |
| 546 | 1.670680003 | 1.94609957 | 0.19633838 | 1.14825764 |
| 547 | −0.24632881 | −0.23975349 | −0.01449288 | 0.574861147 |
| 548 | 1.349418105 | −0.29885837 | 0.42849141 | 0.008671721 |
| 549 | 0.623933699 | −0.62776258 | −1.2835205 | −0.23131507 |
| 550 | 1.091300413 | −0.33969057 | 0.91994098 | 0.043900994 |
| 550 | 1.091300413 | −0.33969057 | 0.91994098 | 0.043900994 |
| 551 | 1.172668936 | −0.39476924 | −0.61394794 | −0.16425167 |
| 552 | 1.434150355 | 1.041294025 | 0.32000606 | 1.24279868 |
| 553 | 1.040907688 | −0.38050079 | −0.95306497 | −0.03036668 |
| 554 | 0.623933699 | −0.65991007 | −1.27562979 | −0.61529805 |
| 555 | 0.623933699 | −0.09654208 | −0.6432411 | 1.36608372 |
| 556 | 0.623933699 | −0.62776258 | −1.2835205 | −0.23131507 |
| 557 | −1.043779684 | 0.358151507 | 0.96578333 | −0.7498558 |
| 558 | 3.113548387 | 0.901949497 | −0.07402944 | 2.171129217 |
| 559 | 1.433732287 | 2.854621121 | 1.81079379 | 0.893806123 |
| 560 | 0.793851811 | 0.195900744 | 1.13222828 | −0.38432626 |
| 561 | 1.874725149 | 0.921395625 | 3.05642524 | 2.616508159 |
| 562 | −1.30410643 | −2.63450231 | 0.12574616 | 1.001870337 |
| 563 | −0.153585698 | 2.733591064 | 2.12854196 | 3.424603045 |
| 565 | 3.655479783 | 3.751479035 | 5.51820797 | 3.282822615 |
| 566 | 4.034374094 | 3.755759834 | 4.82506006 | 3.190861648 |
| 567 | 4.203811008 | 3.627632534 | 4.68751919 | 3.372829008 |
| 568 | 1.643514525 | 0.827299302 | 0.70706274 | 2.545428997 |
| 569 | 2.692371513 | 3.589810155 | 4.40390088 | 4.506937878 |
| 570 | 1.707556133 | 2.400065573 | 1.78745169 | 2.655458557 |
| 571 | 1.862893827 | 2.803280605 | 0.98209954 | 3.188564781 |
| 572 | 1.203581368 | 0.798608763 | 2.67898788 | 1.659633314 |
| 573 | 2.459623568 | 2.656773866 | 3.54771795 | 2.085649266 |
| 574 | 2.878405284 | 1.770500246 | 4.00464111 | 4.859737959 |
| 575 | −0.395731956 | 0.325594009 | 0.98982713 | −0.25791379 |
| 576 | −0.2346025 | 0.890438549 | −0.13206526 | −0.83961838 |
| 577 | 0.484934913 | 2.001798597 | −0.11430063 | −0.05230593 |
| 578 | 1.138642907 | −0.72228381 | −1.0321 | −0.60639529 |
| 579 | −2.722013313 | −3.79238321 | −1.13572295 | 0.953543134 |
| 580 | 1.138642907 | −0.66601616 | −0.95089973 | 1.036450105 |
| 581 | 1.105119249 | −0.82090309 | −0.06184517 | −0.90904158 |
| 582 | 2.092976965 | −0.31228784 | 0.08755137 | −0.62955362 |
| 583 | −0.24632881 | −1.33540368 | −0.96483147 | 0.624830731 |
| 584 | 2.237616041 | 0.30800753 | −0.44296441 | −0.71918014 |
| 585 | 0.634021669 | −0.28724544 | −0.74527157 | −1.361765 |
| 586 | 1.313957377 | 0.449601 | 1.50810166 | −0.30998322 |
| 587 | 0.304876136 | −0.43283205 | 1.23096012 | 0.398961811 |
| 588 | 0.449793066 | 0.007950225 | 0.8004147 | −0.63434071 |
| 589 | −0.681766404 | 1.08547116 | 0.54331319 | −2.16710754 |
| 591 | −0.34676031 | −0.77573166 | 1.85884084 | 0.312272735 |
| 592 | −1.573190219 | 2.29028194 | 1.86285367 | 0.687279186 |
| 594 | −1.45374647 | 0.452156392 | 2.48970747 | 0.858468114 |
| 595 | 0.058003677 | −1.91126878 | 1.52586392 | −0.07528071 |
| 599 | 1.485777974 | 1.54384772 | 0.79002365 | −0.09069773 |
| 600 | 1.914093549 | 0.841364523 | 0.15173954 | 0.255445859 |
| 601 | 1.203870517 | 1.18864533 | 1.22686262 | 0.453935114 |
| 602 | 0.771984982 | 0.66859171 | −0.37427136 | 0.07599515 |

| Material No. | MORV value for Equation a.) | MORV Value for Equation b.) | MORV Value for Equation c.) | MORV value for Equation d.) | Material No. | MORV value for Equation a.) | MORV Value for Equation b.) | MORV Value for Equation c.) | MORV value for Equation d.) |
|---|---|---|---|---|---|---|---|---|---|
| 603 | 3.218950175 | 1.464118271 | 2.47512497 | 1.214429025 | 699 | 0.996500165 | 0.60129571 | −0.27496491 | −0.22179967 |
| 604 | 2.710087358 | 1.517756148 | 0.35088855 | 0.603171932 | 700 | 0.698400489 | 0.514637899 | 1.14265307 | 0.816064314 |
| 605 | 0.703615734 | 0.42129186 | 0.39567696 | 0.41729786 | 701 | 0.592372435 | −0.67812322 | −1.75051912 | −0.51109618 |
| 606 | 0.055463315 | 1.972687323 | 3.42898264 | 1.395457482 | 702 | −0.211768579 | 1.46336231 | −0.93580247 | −1.48749449 |
| 607 | −0.146397553 | −2.05649732 | 0.17598641 | 1.900931587 | 703 | 0.372029303 | 0.866016277 | −0.91679974 | 0.347054507 |
| 608 | 1.473771668 | 2.08260463 | −1.09319437 | 0.44289209 | 704 | 1.187861135 | 0.858978871 | 0.1265005 | 0.217668671 |
| 609 | −0.466215117 | 0.845009196 | 1.89800228 | 0.840292062 | 706 | 0.193569186 | 1.623921627 | 0.08867618 | 0.808617424 |
| 610 | 2.14236439 | 1.079695535 | 0.29060257 | 1.329215628 | 707 | 0.819562098 | 3.57840156 | 3.38080377 | 1.26599216 |
| 611 | 1.078583502 | 1.707732184 | −0.73721672 | −0.87923138 | 708 | 2.391828225 | 1.877690145 | 3.85935427 | 1.647356195 |
| 612 | −0.128136098 | 1.038320983 | −0.63703066 | 0.184527669 | 709 | 1.280902077 | 2.17019575 | 3.40315777 | 0.126982574 |
| 613 | 1.599427115 | 3.615521066 | 0.43343413 | −0.1515479 | 710 | 1.454593977 | 3.128186882 | −2.26368122 | −0.02251455 |
| 614 | 1.489603514 | 2.706865637 | −0.06242639 | −0.47244791 | 711 | −0.783387499 | 1.465620573 | 1.22912535 | −1.41213701 |
| 615 | 1.960664614 | 4.490550162 | 2.26962278 | 0.346542121 | 712 | 1.936489942 | 2.528373237 | 2.13424487 | 2.393940425 |
| 616 | 2.689328335 | 3.692579375 | 2.01499213 | 1.348800283 | 713 | 1.303999908 | 2.146563611 | −0.26420591 | −0.01477791 |
| 617 | −0.845027889 | 0.504788036 | 0.4957383 | −0.65628324 | 714 | 2.3584433 | 3.778880151 | 3.4396901 | 1.593719007 |
| 618 | −0.461016335 | 1.612995126 | 1.09551709 | −1.62235977 | 715 | 4.023918591 | 3.403899942 | 5.07447567 | 4.880181625 |
| 619 | −0.222804396 | 0.361727974 | 0.62743416 | −1.02982449 | 716 | 0.981194248 | 1.73892162 | 2.21166953 | 2.738129365 |
| 620 | 0.745610019 | −0.76737462 | −0.67364137 | 1.696394301 | 717 | 0.983060431 | 2.328872529 | 1.67788951 | 0.805938034 |
| 621 | 3.671429366 | 1.708460032 | 4.57083156 | 1.955988764 | 718 | 1.241840746 | 3.430871861 | 0.55000978 | 1.073616332 |
| 624 | 2.139270802 | 2.093130621 | 2.5533383 | 3.30383102 | 719 | 1.483275952 | 3.037398628 | −1.55547275 | −0.47244791 |
| 625 | 0.665423108 | 1.356936283 | 1.5515704 | 1.874119646 | 720 | 2.372311412 | 3.403234423 | −0.21191089 | −0.08519829 |
| 626 | 1.292942787 | 0.621140137 | 2.28513785 | 1.042322574 | 721 | 2.128185431 | 0.274654772 | 0.47626043 | 2.465333527 |
| 627 | 1.14724223 | −0.51104438 | 1.01088446 | 1.51232276 | 722 | 0.616377169 | −0.58753328 | 0.48821573 | 1.063402884 |
| 628 | 1.44418619 | 3.825155203 | −0.84341678 | −0.02251455 | 723 | −1.273274319 | −1.12897478 | 1.71118519 | 4.067480158 |
| 631 | 2.622138509 | 5.106659136 | 4.48303003 | 2.115425367 | 724 | 2.103515193 | 0.165377929 | −0.18223896 | 0.288303217 |
| 632 | 2.450328692 | 4.670297017 | 4.54579766 | 2.15781135 | 725 | 0.983060431 | 2.328872529 | 1.67788951 | 0.805938034 |
| 633 | 1.560465308 | 2.636096631 | 2.45546606 | 0.920962489 | 726 | 2.887615733 | 3.282342953 | 1.95034945 | 2.462290186 |
| 635 | 1.510161132 | 2.388971583 | −0.63579931 | 1.939575919 | 727 | 2.241052707 | 2.13951389 | 0.36814978 | 0.371689426 |
| 636 | 1.433842763 | 0.529693203 | −0.23195491 | 1.22356734 | 730 | 1.121105724 | −0.20397307 | −0.15741334 | 0.897609916 |
| 638 | 1.921725015 | 0.758255259 | 0.81570009 | 3.615611357 | 731 | 1.437838545 | −0.09620743 | 0.02756967 | 1.949139525 |
| 639 | 0.422001837 | −0.14885323 | −0.00660617 | 1.726576493 | 733 | −0.46922259 | 1.067777032 | 1.61226345 | 0.185415155 |
| 640 | 0.865825265 | −0.28827025 | −0.54129473 | 0.283616979 | 735 | −0.081273581 | 1.192925027 | 1.67970188 | 0.33874614 |
| 641 | 0.813978315 | 0.509726232 | 0.37457254 | 0.842075065 | 736 | −0.13000788 | 1.099012031 | 1.64139691 | 0.248287146 |
| 644 | 0.85173251 | 0.664325682 | 1.88299246 | 0.951603698 | 738 | 1.670680003 | −0.20756775 | −0.73755051 | −0.84924056 |
| 645 | 0.417907652 | −1.00347186 | 0.9667556 | −0.47157656 | 740 | −1.532691904 | −2.55214711 | 0.57438104 | 0.555698696 |
| 647 | 0.221569324 | −1.2239438 | 0.91464498 | −0.19166679 | 741 | 1.407504561 | 0.048284736 | 1.01405149 | −2.2579901 |
| 649 | −0.560315649 | −0.67419393 | −0.02482011 | 1.492767049 | 742 | 0.644803847 | 0.644647752 | 1.35192052 | −0.62780087 |
| 650 | 1.640396187 | 0.328871961 | 0.04729888 | 0.912259803 | 743 | 0.174679072 | 0.169515693 | 0.62350977 | −0.08144308 |
| 651 | 0.672555558 | −0.9987845 | 0.48545476 | −0.13530683 | 744 | 0.02068385 | 0.648730454 | −0.04946215 | 0.214634634 |
| 652 | −0.995969271 | −1.38653208 | −0.49268035 | 0.944524468 | 745 | 0.741424752 | 0.523647641 | 0.52863925 | −0.65426285 |
| 653 | 1.203949791 | 0.0153333 | −0.10401424 | 0.73323846 | 746 | 1.285306965 | 1.929408375 | 0.85560877 | −1.4619958 |
| 655 | 1.334772083 | 0.418728831 | −0.92221842 | 1.317365259 | 748 | −1.513804897 | −1.10823383 | 1.09397284 | −0.88975989 |
| 658 | 0.414934548 | 0.314990682 | 2.78051829 | 2.656854539 | 750 | 2.554017714 | 3.544542579 | 4.42317523 | 1.647356195 |
| 659 | 3.996948911 | 1.915319951 | 3.03990612 | 5.764113617 | 752 | 2.592229701 | 1.158945916 | 0.24149847 | −0.58379051 |
| 660 | 2.175041013 | 1.882945358 | 0.07779745 | −0.18323732 | 754 | 1.649506181 | 1.31981993 | 2.36997533 | 0.406081966 |
| 661 | −0.316755016 | 1.64607349 | 2.76327471 | 2.024910676 | 755 | −0.028552173 | 0.253838465 | 0.95694896 | −0.16565786 |
| 662 | 0.258228842 | 0.844792644 | 0.1924797 | 0.098776211 | 757 | 1.446915042 | 0.673406021 | −0.6641103 | −1.80002119 |
| 663 | 1.521826905 | 1.097809988 | 2.13583044 | 1.30609234 | 758 | 5.933043009 | 5.716461604 | 6.67410554 | 4.433272782 |
| 664 | 0.708920214 | −0.27795513 | 0.15395433 | 0.014791904 | 760 | −3.195604514 | −2.60998376 | −0.11222221 | 0.792186468 |
| 665 | 0.630772742 | −0.34278374 | 0.49097281 | −0.0565644 | 761 | 0.286783044 | −0.52414055 | −0.57593161 | 0.628896611 |
| 667 | 0.812238101 | 0.195908668 | 0.21564664 | 0.219336109 | 763 | 1.405567948 | −0.84372738 | −1.32379279 | −0.50314577 |
| 668 | 1.529097453 | 2.246515706 | 1.4678099 | −0.81836944 | 766 | 0.279442569 | −1.00722191 | −0.18524031 | 2.487147765 |
| 671 | 1.453855457 | −0.51177209 | −0.78608937 | 0.361715513 | 767 | −1.32777782 | −2.36136561 | −0.79602501 | 1.247063893 |
| 672 | 0.771613806 | −0.81209599 | −0.85297613 | 0.084880782 | 768 | −0.692560954 | −1.92177717 | 0.46687554 | 2.400762497 |
| 673 | 1.874725149 | 0.921395625 | 3.05642524 | 2.616608159 | 769 | 1.889999468 | 1.112266205 | 0.82815523 | 0.525271623 |
| 674 | 5.912391366 | 3.468705262 | 6.81994671 | 7.217631788 | 770 | 2.237616041 | 2.282141767 | −0.149966 | −0.71866539 |
| 675 | 0.525794155 | 0.473286101 | 2.51749677 | 2.935001452 | 771 | 0.909356011 | 0.368597887 | 1.03689838 | 1.001198751 |
| 676 | 0.623704257 | 1.523736626 | 2.50208859 | 2.474137331 | 772 | 1.328601831 | 0.715296776 | 0.20358825 | 1.147403521 |
| 677 | −0.548848405 | 0.058004962 | 1.07849806 | 2.361730638 | 774 | 2.002379485 | 3.95875961 | 1.1705779 | 0.346542121 |
| 678 | 4.818555677 | 1.506257638 | 4.96635528 | 5.508133385 | 775 | 1.936489942 | 2.528373237 | 2.13424487 | 2.393940425 |
| 679 | 4.332202737 | 2.699343437 | 5.65576391 | 5.021298111 | 776 | 1.495019673 | 4.35984375 | 2.59969954 | 2.95313487 |
| 680 | 4.042984412 | 4.75506829 | 4.65903898 | 4.913020939 | 777 | 0.206892499 | −0.57813502 | −0.32983 | 0.781221286 |
| 681 | 0.5959536 | 2.091803965 | −0.14697928 | −0.71889234 | 778 | 1.340232187 | −0.11034804 | 0.35759778 | 1.690582999 |
| 683 | 0.87899671 | 0.043210589 | 1.37554648 | −0.601998897 | 779 | 0.595257521 | −0.85639987 | 0.19436224 | −0.73333902 |
| 684 | 2.349844428 | 1.181400632 | 2.15359469 | 2.136987013 | 781 | 2.187955186 | 2.571774369 | 2.74817529 | −0.52827851 |
| 686 | 1.024635336 | 1.040500794 | 0.9820242 | −1.16405004 | 782 | 0.893855657 | 0.63313304 | 1.19104388 | −1.61620514 |
| 687 | 0.551495677 | 0.66297128 | −0.45433071 | −1.28827912 | 784 | −0.275919571 | −1.64491584 | 0.60429762 | −1.5580623 |
| 691 | 1.609835015 | 2.898881191 | −0.99203246 | −0.15162554 | 786 | −0.043537347 | 1.337721065 | −0.56551398 | −0.02167052 |
| 692 | 2.002379485 | 3.95875961 | 1.1705779 | 0.346542121 | 788 | 2.147983695 | 1.250042565 | 1.72576392 | 1.626956379 |
| 693 | 4.264631423 | 4.375626605 | 0.93418004 | 0.114988571 | 789 | −0.624451013 | 0.76248127 | −0.79219481 | −0.73513092 |
| 693 | 4.264631423 | 4.375626605 | 0.93418004 | 0.114988571 | 791 | 0.227060873 | −0.04783658 | −0.16862915 | 1.166609659 |
| 694 | 4.858313721 | 4.772826468 | 3.58732214 | 2.558402204 | 792 | 0.90746622 | 1.643598677 | 0.26467094 | 0.396081003 |
| 696 | 2.99409154 | 3.843066736 | 2.50597637 | 1.205022789 | 796 | 0.811374104 | 0.766579899 | 0.10161642 | 0.135186519 |
| 697 | 0.407534444 | 2.829113684 | 2.16548165 | 0.756766079 | 797 | −0.185638022 | 0.53853264 | 0.65441562 | −0.25681926 |
| 698 | 0.983060431 | 2.328872529 | 1.67788951 | 0.805938034 | 799 | 0.657769581 | 0.095543194 | 0.89522656 | 0.558428618 |

| Material No. | MORV value for Equation a.) | MORV Value for Equation b.) | MORV Value for Equation c.) | MORV value for Equation d.) |
| --- | --- | --- | --- | --- |
| 800 | 0.227060873 | −0.04783658 | −0.16862915 | 1.166609659 |
| 802 | −0.660595577 | 1.597474466 | 1.49106895 | −0.20429128 |
| 803 | 1.706162052 | 0.623892414 | 0.59662073 | 0.7745661 |
| 804 | 3.478490379 | 2.348697011 | 3.96279011 | 2.456963386 |
| 805 | 0.377241729 | 0.83329773 | 0.1712741 | 1.057125999 |
| 806 | 2.863652137 | 0.771287371 | −0.4183972 | −0.44551461 |
| 807 | 1.794279084 | 0.711717977 | 0.35187068 | −1.0208486 |
| 808 | 0.408210632 | 0.633556897 | −0.37022584 | 0.717270748 |
| 810 | −2.506277966 | −2.61703099 | 0.87880054 | −0.72832121 |
| 811 | −0.789075789 | −0.15346024 | 0.64720487 | −0.48507671 |
| 812 | −1.395132583 | −2.59063834 | 0.14973761 | 0.623759794 |
| 814 | 0.414608216 | −0.23108581 | 1.15081653 | −1.10351559 |
| 817 | −0.24632881 | −0.09354384 | −0.13580399 | 0.599029186 |
| 819 | 0.805916178 | 0.96701754 | −0.8811308 | −1.23858491 |
| 820 | 0.744770665 | −0.73855596 | −0.2249849 | −0.2981968 |
| 821 | 1.099377934 | −0.55297074 | −0.58846144 | −1.64325365 |
| 824 | −0.183625049 | 1.183962609 | 1.63494269 | 0.25504959 |
| 826 | 1.678825829 | 1.234136613 | 1.45948258 | 0.224375571 |
| 827 | 2.592229701 | 0.621958527 | −0.52522117 | −0.19676404 |
| 828 | 2.592229701 | 0.57915141 | −0.51767373 | −0.58077497 |
| 829 | 1.670680003 | 1.284791367 | 0.14864516 | −0.84985664 |
| 831 | 1.116827432 | −0.75462162 | 0.39137278 | −0.04171761 |
| 832 | 0.516805788 | −0.98195801 | −1.03806082 | −0.25383454 |
| 833 | 1.490368312 | 0.080687244 | −0.97130296 | 0.833722265 |
| 834 | −0.369014518 | −1.35841128 | −1.27372214 | 1.351157886 |
| 835 | 0.914072736 | −0.8695664 | 0.36889212 | −0.08606658 |
| 836 | 0.998848923 | −0.42464651 | −0.23731009 | 0.395895785 |
| 837 | 1.670680003 | 0.070165381 | −0.64700996 | −0.85055617 |
| 838 | 0.810918992 | −0.75696962 | −0.21854084 | 0.836677293 |
| 839 | 1.066219316 | −0.66764691 | −0.49983634 | 0.669914 |
| 840 | 1.078821776 | −0.72511699 | −1.00012288 | −0.15789319 |
| 845 | −0.163950017 | −0.21616766 | 0.65276069 | −0.52575739 |
| 846 | 0.665621985 | −3.16625248 | 0.34329102 | −1.44312939 |
| 847 | −0.233400992 | −1.15488444 | 0.83051343 | −1.85751897 |
| 848 | −0.631135606 | 0.037691556 | 0.57903451 | −0.9926 |
| 849 | 1.707541313 | 0.010345383 | 0.48581606 | 1.513341091 |
| 850 | 1.447075297 | 0.022864201 | 0.99130501 | 0.473154634 |
| 851 | −0.24632881 | −0.23975349 | −0.01449288 | 0.574861147 |
| 852 | 1.176028423 | −0.85747031 | −0.72464089 | 0.30542841 |
| 856 | 2.237616041 | 0.345329597 | −0.60597063 | −0.71581056 |
| 858 | −1.47960224 | −2.5770536 | −1.03619781 | 0.847300104 |
| 864 | 1.670680003 | 1.284791101 | 0.14864516 | −0.84985664 |
| 865 | 1.670680003 | 1.916382859 | 0.6998144 | 1.124089601 |
| 866 | 1.024819853 | −0.7521596 | 0.35073152 | −2.14193241 |
| 868 | 2.237616041 | −0.17986241 | −0.86317199 | 1.325805381 |
| 869 | 1.747776963 | −0.25802105 | −1.11614995 | −0.77093434 |
| 870 | 2.592229701 | 2.030913569 | −0.50618719 | 1.463926567 |
| 871 | 2.592229701 | 2.510587108 | −0.07540594 | −0.58371481 |
| 872 | 1.800767509 | 1.372656013 | 2.09551175 | 2.849728342 |
| 873 | 1.849432484 | 4.556065495 | −0.39732139 | −0.67726477 |
| 875 | 0.201768224 | 0.618509503 | −0.39732139 | −0.67726477 |
| 876 | 2.237616041 | 1.553468488 | −0.72864242 | −0.33330779 |
| 877 | 0.323968221 | −1.00428076 | −1.65151616 | 1.031096548 |
| 878 | 0.783570663 | 2.023288951 | −0.03975252 | 0.474038265 |
| 879 | 1.187592149 | 1.464239711 | 0.67009263 | 1.103774764 |
| 880 | −0.192632911 | 0.142411101 | 0.79310676 | 0.125548041 |
| 881 | 1.071875228 | 0.911734331 | −1.50008456 | 0.185176261 |
| 882 | 0.798806784 | −0.1516478 | −0.64900063 | −0.77199025 |
| 883 | −0.671908804 | −0.65984824 | 0.5238174 | −0.85314111 |
| 884 | 2.863652137 | 1.896850773 | 0.06443558 | −0.44689505 |
| 885 | 2.314558863 | −0.25458637 | 0.22080129 | −0.04142716 |
| 886 | 2.314558863 | −0.25458637 | 0.22080129 | −0.04142716 |
| 888 | 0.131224024 | 0.21510779 | −1.70996346 | 0.964902175 |
| 889 | 0.742030255 | 0.281479436 | −1.4156326 | −1.91369695 |
| 890 | 1.071875228 | 0.911734331 | −1.50008456 | 0.185176261 |
| 891 | 0.742030255 | 0.281479436 | −1.4156326 | −1.91369695 |
| 892 | 1.749446006 | 0.076054765 | −0.59137073 | 0.291488011 |
| 893 | 0.869958847 | 0.843158237 | 0.61532515 | 3.158279932 |
| 894 | 1.749446006 | 0.076054765 | −0.59137073 | 0.291488011 |
| 897 | −0.047486491 | 1.045012945 | −0.25220201 | −0.31982826 |
| 899 | 0.784181146 | −0.20530019 | −1.89414748 | 0.152726109 |
| 900 | 0.784181146 | −0.20530019 | −1.89414748 | 0.152726109 |
| 901 | −0.440378333 | 0.918089245 | 0.03050609 | −1.62235977 |
| 902 | −0.2346025 | 0.890438419 | −0.13206526 | −0.83961838 |
| 903 | −0.440378333 | 0.918089245 | 0.03050609 | −1.62235977 |
| 904 | −1.320466583 | −2.49763118 | 0.9787365 | −1.85867969 |
| 905 | −0.386224123 | −0.24799559 | 1.19406353 | −1.61243489 |
| 908 | 1.878331515 | 1.287303121 | 0.11530502 | 1.132065786 |
| 909 | 0.614968453 | −1.61827184 | −0.80789799 | −0.66927285 |
| 912 | 0.530707518 | 0.774109528 | 3.0396125 | 4.394775258 |
| 913 | 0.337020095 | 1.531840025 | 0.10544973 | 0.347450471 |
| 914 | 0.774589061 | 1.224705331 | 1.87994281 | −0.11684579 |
| 916 | −0.363201351 | 0.35600238 | −1.20673542 | 2.056973054 |
| 918 | 0.153047955 | 0.702054562 | 0.76757802 | 0.096096862 |
| 919 | 2.891894151 | 2.295157633 | 3.54101626 | 1.984030826 |
| 920 | 1.292959895 | 0.808281618 | 2.92956952 | 2.204248324 |
| 921 | −0.465333775 | 0.862817284 | 0.1439546 | 0.64701735 |
| 922 | 1.54265003 | 0.291977233 | 0.79089158 | 0.801314068 |
| 923 | 1.340862559 | 0.503169303 | 0.53213093 | 3.164832031 |
| 924 | 0.158497146 | 1.507280765 | 2.25315926 | 1.173977914 |
| 925 | 1.23162703 | 1.671882685 | 3.1838372 | −0.22917041 |
| 926 | 2.608734063 | 3.080604939 | −0.69726361 | −0.36219702 |
| 927 | 1.879182741 | 3.409153142 | 2.48473663 | 3.409954437 |
| 928 | −0.093106169 | 0.019939108 | 0.15932154 | 1.229749745 |
| 929 | 1.670680003 | 1.94609957 | 0.19633838 | 1.14825764 |
| 930 | 3.052627325 | 0.956834107 | −0.29721209 | −0.31007607 |
| 931 | 0.367631287 | 0.501274945 | −1.31074554 | −0.39331005 |
| 933 | 3.702965303 | 3.03402795 | 4.33630831 | 4.238503729 |
| 937 | 0.570011387 | 0.097928934 | 1.03350455 | −0.13392581 |
| 939 | 1.801474588 | 0.770314085 | 0.70188154 | 0.22333959 |
| 940 | −0.412950838 | −0.1781887 | 0.50649275 | −0.57215449 |
| 941 | 1.691004766 | −0.42331992 | 0.66279648 | 0.0318465 |
| 942 | 1.451782586 | −0.565439 | −0.32447381 | −0.43378383 |
| 943 | 1.188491672 | 0.120632811 | 0.20106994 | 3.078484746 |
| 945 | 1.214814941 | 0.806987609 | 0.47605587 | 1.372949466 |
| 946 | 0.561732094 | 1.21448402 | 0.35542793 | −1.03704442 |
| 947 | 0.956565856 | 1.505997176 | 0.88115653 | −0.60583691 |
| 948 | 0.592575441 | 1.383482681 | 0.93567635 | 1.058669028 |
| 950 | 0.343657562 | −0.85471906 | −0.21125904 | 1.184648122 |
| 951 | 1.236659334 | 3.828926809 | 1.57729777 | −0.31942874 |
| 953 | 1.836389049 | 0.755753735 | −0.36014522 | 1.262853393 |
| 953 | 1.836389049 | 0.755753735 | −0.36014522 | 1.262853393 |
| 954 | 1.001653875 | −0.85635082 | 0.89224781 | −0.39245818 |
| 955 | −0.122918652 | −0.846489 | −0.63367729 | 1.182912962 |
| 956 | 0.589766639 | −0.9783487 | −0.67638264 | −0.38772225 |
| 958 | 0.715082397 | −0.90020686 | 0.86817768 | 0.030652004 |
| 959 | 1.609198886 | 0.500797943 | 0.795571 | 0.908389449 |
| 960 | 0.952787327 | −0.90555475 | −0.17381408 | 0.06786323 |
| 962 | 1.836429446 | 0.208275147 | −0.14300625 | 1.067462181 |
| 965 | 1.9158432 | 0.35211823 | −1.02174589 | 0.625657932 |
| 967 | 1.383869627 | 0.274520494 | −0.11659267 | 0.840327437 |
| 969 | −0.445579934 | −1.68867059 | −0.5241276 | 2.233793943 |
| 971 | 0.736419048 | 0.409875189 | −0.63140848 | 0.034514594 |
| 973 | 1.073465817 | 2.18418874 | 2.01361447 | −0.93754437 |
| 974 | 0.130904221 | 1.882440008 | 1.85101055 | 0.112524893 |
| 976 | −0.236681385 | −0.09745533 | 0.1779313 | 2.08923364 |
| 977 | 0.904402612 | 0.936956925 | 0.87731788 | 0.102346515 |
| 978 | 2.201759817 | 2.123549573 | 3.7881607 | 2.358768953 |
| 980 | 1.784266982 | 1.845281076 | 3.42873622 | −0.31098233 |
| 981 | −0.225023329 | 0.087962898 | −0.29053012 | 0.514272787 |
| 982 | −0.231175318 | −0.0159671 | 1.27391892 | 1.090487158 |
| 983 | 0.889215441 | 0.24321159 | 0.06877629 | 0.816247177 |
| 985 | 1.864634345 | 0.133647536 | 1.29803755 | 1.951226654 |
| 986 | 0.511450274 | −2.33512445 | −0.56246315 | −0.42184152 |
| 987 | 0.847260813 | 0.368628185 | 0.4114346 | 0.219336109 |
| 988 | 1.596170102 | 1.592158381 | 0.30052357 | 0.283467897 |
| 993 | −3.549941097 | −2.6847861 | −0.17502622 | 1.41034664 |
| 994 | 0.445802042 | 0.899738574 | 0.61059602 | 0.323194673 |
| 995 | 0.949498724 | 0.357111159 | 0.28371155 | −0.14156488 |
| 998 | 2.197271885 | 1.578871826 | 0.90563334 | 1.056619658 |
| 998 | 2.197271885 | 1.578871826 | 0.90563334 | 1.056619658 |
| 1000 | 1.456120673 | 0.626173572 | 0.07683183 | −0.43324035 |
| 1001 | −0.440378333 | 0.918089245 | 0.03050609 | −1.62235977 |
| 1002 | 0.819929066 | 0.459101825 | −0.09227583 | 0.324342063 |
| 1003 | 1.64412453 | −0.09343399 | 0.70197344 | 3.710273595 |
| 1004 | 0.796928207 | 0.459954079 | −0.88538616 | 0.152000937 |
| 1005 | 0.044923203 | −0.19994963 | 0.60082875 | 0.258347835 |
| 1006 | −0.320452673 | −0.33232662 | −0.52315783 | 1.406273663 |
| 1007 | 4.040291133 | 3.474551355 | 3.57146797 | 3.565985043 |
| 1008 | 0.764519082 | 0.917635102 | 2.88258762 | 2.319622474 |

| Material No. | MORV value for Equation a.) | MORV Value for Equation b.) | MORV Value for Equation c.) | MORV value for Equation d.) |
| --- | --- | --- | --- | --- |
| 1009 | −0.071112206 | 0.539362906 | 2.98048732 | 0.580423329 |
| 1010 | −0.689737481 | 0.547928768 | 1.98805626 | −0.76653376 |
| 1011 | 0.343668917 | 0.931501008 | −0.05483722 | 0.395369857 |
| 1012 | 1.926713131 | 0.124849138 | −0.09654906 | 1.126499382 |
| 1016 | 0.124247716 | 0.193102712 | 0.39003599 | 1.737670628 |
| 1017 | 0.131224136 | 0.21510779 | −1.70996346 | 0.964902175 |
| 1018 | 0.499624069 | 0.962843507 | 0.77617619 | −1.15296947 |
| 1019 | 0.813491983 | 0.322635656 | 0.02800396 | 0.599500927 |
| 1020 | 0.715468114 | 1.015469049 | 1.45994989 | 0.352548581 |
| 1021 | −1.176339404 | 1.539767848 | −0.14427147 | 1.389902738 |
| 1022 | 1.364966718 | 1.690570939 | 2.05914194 | 2.364375484 |
| 1023 | 2.154641091 | 0.800066339 | 0.85365652 | 0.965810338 |
| 1024 | 2.302280068 | 1.252164308 | 1.73414439 | 1.549538352 |
| 1025 | 1.878331515 | 1.287303121 | 0.11530502 | 1.132065786 |
| 1026 | 2.97722987 | 2.096441965 | 3.87172868 | 0.550274831 |
| 1027 | 2.474381478 | 1.950326182 | 3.81861867 | 1.366897355 |
| 1028 | 1.778414353 | 3.114931059 | 4.47690731 | 6.054314034 |
| 1029 | 3.672910795 | 2.760483725 | 3.26915034 | 3.042677588 |
| 1030 | −0.604959715 | −2.13584086 | 0.8687855 | 0.024144016 |
| 1031 | 2.012732245 | 2.293857161 | 0.54405555 | 1.261882121 |
| 1032 | −1.086688867 | 0.953083194 | 2.92177054 | 0.876865185 |
| 1033 | 1.617520676 | 1.008017006 | 2.21183536 | −0.1288484 |
| 1035 | 2.506372295 | 3.419954592 | 4.58206882 | 4.134341651 |
| 1036 | −0.675805062 | −0.15357004 | 0.94597719 | 3.966016669 |
| 1037 | −0.275092569 | −0.67687665 | −0.52763797 | 1.489972106 |
| 1038 | 2.753559643 | 3.81185814 | 2.71344734 | 2.243351472 |
| 1039 | 0.65087433 | 0.026885305 | −0.0153558 | 0.011870127 |
| 1040 | 0.141526548 | −1.65455278 | 0.50170705 | −1.90794 |
| 1041 | 0.458680435 | −0.69730218 | −0.48806249 | 0.586073092 |
| 1042 | −0.513264812 | −0.22001961 | 0.36339519 | 1.03208599 |
| 1043 | −1.497887014 | −1.76116109 | −0.76634926 | 1.137002742 |
| 1045 | 2.863652137 | 1.96790869 | 0.43661485 | −0.44756897 |
| 1046 | 0.981194248 | 1.73892162 | 2.21166953 | 2.738129365 |
| 1047 | 0.981194248 | 1.73892162 | 2.21166953 | 2.738129365 |
| 1051 | 0.70261974 | −0.22197386 | 0.19710806 | −2.37196477 |
| 1052 | 0.662126832 | 0.741436531 | 0.61672724 | 0.289359903 |
| 1053 | 0.87463644 | −0.19717783 | 1.2664131 | −0.4187507 |
| 1054 | 0.284558077 | −1.46754925 | −0.03124571 | 0.587227244 |
| 1055 | 0.885837831 | −0.91907796 | −0.45817355 | −1.1936897 |
| 1057 | 0.790964847 | 1.387925398 | −0.18370692 | 1.302393792 |
| 1058 | −1.052897931 | −0.85226912 | 0.90324527 | −1.09684959 |
| 1059 | −0.871565421 | −0.17856476 | 1.51267137 | −1.52734367 |
| 1060 | 3.311161199 | 3.074783921 | 2.10199297 | 1.822541682 |
| 1061 | −0.655128061 | 0.497032417 | 0.92381279 | −0.56348341 |
| 1062 | −0.443129049 | 0.96200606 | 1.51641349 | −0.22974864 |
| 1063 | 1.385675542 | 0.738759296 | 1.1677069 | 0.501211562 |
| 1064 | 1.670680003 | −0.20756775 | −0.73755051 | −0.84924056 |
| 1065 | 1.43532227 | 1.656262941 | −1.09448841 | 1.674272267 |
| 1066 | 1.670680003 | 1.284791101 | 0.14864516 | −0.84985664 |
| 1067 | 2.237616041 | 0.345329863 | −0.60597063 | −0.71581056 |
| 1069 | −0.24632881 | −0.23975349 | −0.01449288 | 0.574861147 |
| 1070 | 1.670680003 | 0.070165381 | −0.64700996 | −0.85055617 |
| 1071 | −1.02687397 | −0.36244273 | 0.13010074 | 0.535909448 |
| 1072 | 1.670680003 | 1.94609957 | 0.19633838 | 1.14825764 |
| 1073 | 2.237616041 | 1.438074134 | 0.31117554 | −0.71786492 |
| 1074 | −0.192632911 | 0.142411101 | 0.79310676 | 0.125548041 |
| 1075 | 0.909356011 | 0.368597887 | 1.03689838 | 1.001198751 |
| 1076 | 0.812238101 | 0.195908668 | 0.21564664 | 0.219336109 |
| 1077 | 0.325255266 | 1.131242708 | −2.79377204 | −0.62848261 |
| 1078 | 0.325255266 | 1.131242708 | −2.79377204 | −0.62848261 |
| 1079 | 0.85330799 | −0.6855194 | −0.90046979 | −0.46415796 |
| 1081 | −0.131519393 | 0.731836014 | 0.81604919 | −1.29993979 |
| 1082 | 0.744770665 | 0.155243763 | −1.8029919 | 1.023503542 |
| 1083 | 1.415726941 | 0.086297223 | 3.43559555 | −0.12964168 |
| 1084 | 0.161304111 | 0.66712144 | 0.58401752 | 0.373809692 |
| 1085 | −0.72863532 | −0.2873027 | 2.21251376 | 3.003873022 |
| 1088 | −1.1773616 | −0.23258175 | 0.40529195 | 0.994988969 |
| 1089 | 2.769817302 | 1.661618789 | 3.97585272 | 1.059236597 |
| 1090 | 3.052627325 | 0.420821685 | −0.57080756 | 1.751222205 |
| 1091 | −3.379896722 | −3.71174986 | 2.53586709 | 0.644702886 |
| 1093 | 0.72304265 | 1.667011476 | 2.53982093 | 2.7903213 |
| 1095 | 0.744219765 | 1.372184572 | 0.15852396 | 1.126053442 |
| 1097 | 4.407270402 | 2.670641491 | 5.02636153 | 5.361271976 |
| 1098 | −1.85804837 | −2.59071226 | −0.46522239 | 0.655734646 |
| 1099 | 0.745797788 | −0.20547378 | 4.27836342 | 4.646390386 |
| 1102 | 2.068748434 | −0.24299896 | 0.07214682 | −1.11758276 |
| 1104 | 1.018876287 | 0.025163067 | −0.1106021 | 0.838914654 |
| 1105 | 2.387326861 | 3.865456674 | 2.2251199 | 0.728667998 |
| 1107 | 2.352582059 | 2.595496601 | 3.20492728 | 2.844590737 |
| 1110 | 0.302703712 | 0.599942142 | −0.25637571 | −0.03195517 |
| 1111 | 0.750930333 | 0.656784751 | 1.68326413 | 0.329846578 |
| 1112 | −0.205527848 | 0.287622624 | −0.00340777 | 0.59203719 |
| 1115 | 0.999825037 | 0.662221152 | 0.43571192 | 0.342558518 |
| 1116 | 0.873381263 | 1.544324176 | 0.13703728 | −0.38172701 |
| 1117 | −0.682983903 | 1.798204302 | 2.42110319 | −0.39173951 |
| 1118 | 0.069769623 | 0.496895599 | 0.67857133 | −0.14954441 |
| 1119 | −0.671908804 | −0.65984824 | 0.5238174 | −0.85314111 |
| 1120 | 0.953790113 | 1.106552668 | 3.00006904 | 1.585038764 |
| 1121 | −1.184630973 | 2.476138312 | 4.80971952 | 2.450646806 |
| 1122 | −1.02687397 | −0.36244273 | 0.13010074 | 0.535909448 |
| 1125 | 0.387315524 | −0.36101406 | 1.14153708 | −0.75303953 |
| 1126 | 1.021783831 | −0.0070257 | −0.14327539 | 3.954381426 |
| 1127 | 0.990592079 | 0.305612583 | 0.14155512 | −0.29526854 |
| 1128 | 0.990592079 | 0.305612583 | 0.14155512 | −0.29526854 |
| 1129 | 3.18966648 | 3.284362987 | 4.49398568 | 3.950809104 |
| 1131 | 1.650621055 | 1.545704806 | 2.37535081 | 1.259373143 |
| 1133 | −1.519747805 | −0.60804324 | 0.02746106 | 0.590708892 |
| 1134 | 0.815942067 | −0.16126019 | −0.54117238 | 0.613093526 |
| 1135 | 0.626973385 | 1.998305877 | 2.61706075 | 1.570404253 |
| 1136 | 2.812199484 | 1.353198146 | 2.05618426 | 1.869204406 |
| 1137 | 2.208307057 | 1.387136198 | 3.21521374 | 2.069795393 |
| 1138 | 1.670680003 | 1.316442078 | 0.14822999 | −0.46985154 |
| 1139 | 1.408517438 | 0.890457374 | 1.24524408 | 0.685687797 |
| 1140 | 2.765860952 | 2.525539595 | 4.12464228 | 3.833744077 |
| 1141 | −0.484394663 | 0.677713073 | −0.22783646 | −0.37267608 |
| 1142 | 2.54335679 | 4.298105601 | 3.36234238 | 2.684404542 |
| 1143 | 4.204367611 | 3.062126931 | 3.4234313 | 2.072899554 |
| 1144 | 2.479165229 | 3.226545885 | 4.65897152 | 4.952127235 |
| 1145 | 2.479158921 | 3.226545885 | 4.65897152 | 4.952127235 |
| 1146 | 0.774334025 | 1.075800774 | 1.06893156 | 1.011113116 |
| 1147 | 0.844648531 | 1.21935371 | 2.59138595 | 0.805938034 |
| 1148 | 2.906236436 | 1.550674121 | 3.56959167 | 2.832126896 |
| 1149 | 2.837627443 | 3.707154326 | 4.53384262 | 2.625871865 |

Compositions and Methods

A personal care composition comprising, based on total composition weight,
- a) a sum total of from about 0.0001% to about 2%, preferably from about 0.0001% to about 0.75%, more preferably from about 0.001% to about 0.5%, most preferably from about 0.007% to about 0.25% of 1 or more malodor reduction materials, preferably 1 to about 75 malodor reduction materials, more preferably 1 to about 50 malodor reduction materials, more preferably 1 to about 35 malodor reduction materials, most preferably 1 to about 20 malodor reduction materials, each of said malodor reduction materials having a MORV of at least 0.5, preferably from 0.5 to 10, more preferably from 1 to 10, most preferably from 1 to 5, and preferably each of said malodor reduction materials having a Universal MORV, or said sum total of malodor reduction materials having a Blocker Index of less than 3, more preferable less than about 2.5 even more preferably less than about 2 and still more preferably less than about 1 and most preferably 0 and/or a Blocker Index average of 3 to about 0.001; and
- b) from about 0% to about 12%, preferably from about 0% to about 8%, more preferably from about 0.1% to about 4%, of one or more perfume raw materials having a MORV of less than 0.5, preferably less than 0, more preferably less than −2, most preferably less than −5;
- c) from about 0.1% to about 99%, preferably from about 1% to about 80%, more preferably from about 5% to about 70%, most preferably from about 10% to about 50% of a solvent, preferably said solvent is selected from, water, glycerin, and mixtures thereof;

d) from about 0% to about 50%, preferably from about 0% to about 40%, more preferably from about 0.1% to about 30%, most preferably from about 0.1% to about 15% of a material selected from the group consisting of a structurant, a humectant, a surfactant, an antimicrobial, and mixtures thereof is disclosed.

In one aspect of said personal care composition according to claim 1, wherein said sum total of malodor reduction materials has a Blocker Index of less than 3, more preferable less than about 2.5 even more preferably less than about 2 and still more preferably less than about 1 and most preferably 0 and/or a Blocker Index average of 3 to about 0.001.

In one aspect of said personal care composition, each of said malodor reduction materials has a MORV of at least 0.5, preferably from 0.5 to 10, more preferably from 1 to 10, most preferably from 1 to 5, and preferably each of said malodor reduction materials having a Universal MORV.

In one aspect of said personal care composition, said sum total of malodor reduction materials has a Fragrance Fidelity Index average of 3 to about 0.001 Fragrance Fidelity Index, preferably each malodor reduction material in said sum total of malodor reduction materials has a Fragrance Fidelity Index of less than 3, preferably less than 2, more preferably less than 1 and most preferably each malodor reduction material in said sum total of malodor reduction materials has a Fragrance Fidelity Index of 0.

In one aspect of said personal care composition, said composition comprises a malodor reduction material selected from the group consisting of Table 1, 3 and 3 materials and mixtures thereof; preferably said material is selected from the group consisting of Table 1 materials: 1, 2, 3, 4, 7, 9, 10, 11, 13, 14, 16, 17, 18, 21, 22, 23, 25, 28, 29, 30, 31, 32, 33, 34, 35, 36, 37, 38, 39, 42, 43, 47, 48, 49, 50, 52, 57, 61, 62, 63, 64, 65, 67, 68, 69, 70, 71, 74, 75, 76, 77, 78, 79, 80, 82, 83, 85, 91, 92, 93, 98, 100, 101, 102, 103, 104, 105, 106, 108, 109, 110, 112, 113, 114, 117, 119, 120, 122, 123, 126, 128, 130, 134, 135, 137, 140, 141, 142, 143, 145, 146, 148, 149, 152, 153, 155, 156, 158, 159, 161, 162, 167, 168, 170, 174, 175, 176, 177, 178, 179, 182, 183, 184, 185, 186, 187, 189, 190, 192, 193, 195, 196, 197, 199, 206, 208, 209, 210, 211, 212, 215, 218, 221, 227, 228, 229, 230, 231, 233, 234, 238, 242, 243, 244, 246, 247, 249, 252, 253, 254, 256, 259, 260, 261, 263, 267, 269, 271, 274, 276, 277, 278, 280, 281, 285, 286, 288, 289, 290, 292, 293, 294, 295, 296, 300, 301, 303, 307, 316, 317, 318, 321, 322, 323, 324, 325, 328, 329, 330, 331, 332, 333, 334, 335, 336, 338, 339, 342, 343, 344, 347, 349, 350, 352, 353, 356, 358, 359, 360, 361, 362, 363, 364, 368, 369, 370, 371, 372, 373, 374, 375, 377, 378, 381, 385, 386, 388, 390, 391, 394, 397, 398, 407, 413, 414, 415, 416, 417, 418, 421, 424, 425, 426, 428, 429, 432, 436, 441, 444, 445, 449, 450, 453, 457, 459, 461, 462, 463, 464, 465, 466, 467, 468, 470, 471, 473, 474, 475, 478, 479, 480, 482, 484, 485, 486, 487, 488, 491, 493, 497, 498, 501, 502, 503, 505, 519, 520, 521, 524, 527, 529, 530, 531, 532, 534, 537, 541, 544, 546, 548, 550, 551, 552, 553, 555, 558, 559, 560, 561, 562, 563, 565, 566, 567, 568, 569, 570, 571, 572, 573, 574, 577, 578, 580, 581, 582, 584, 586, 587, 589, 591, 592, 594, 595, 599, 600, 601, 603, 604, 606, 607, 608, 609, 610, 611, 612, 613, 614, 615, 616, 618, 620, 621, 624, 625, 626, 627, 628, 631, 632, 633, 635, 636, 638, 639, 644, 649, 650, 653, 655, 658, 659, 660, 661, 663, 668, 671, 673, 674, 675, 676, 677, 678, 679, 680, 681, 682, 683, 684, 686, 691, 692, 693, 694, 696, 697, 698, 700, 702, 704, 706, 707, 708, 709, 710, 711, 712, 713, 714, 715, 716, 717, 718, 719, 720, 721, 722, 723, 724, 725, 726, 727, 730, 731, 733, 735, 736, 738, 741, 742, 746, 748, 750, 752, 754, 757, 758, 763, 764, 766, 767, 768, 769, 770, 771, 772, 774, 775, 776, 778, 781, 782, 786, 788, 791, 792, 800, 802, 803, 804, 805, 806, 807, 814, 821, 824, 826, 827, 828, 829, 831, 833, 834, 837, 839, 840, 849, 850, 852, 856, 864, 865, 866, 868, 869, 870, 871, 872, 873, 876, 877, 878, 879, 881, 884, 885, 886, 890, 892, 893, 894, 897, 905, 908, 912, 913, 914, 916, 919, 920, 922, 923, 924, 925, 926, 927, 928, 929, 930, 933, 937, 939, 941, 942, 943, 945, 946, 947, 948, 950, 951, 953, 954, 955, 959, 962, 965, 967, 969, 973, 974, 976, 978, 980, 982, 985, 988, 993, 998, 1000, 1003, 1006, 1007, 1008, 1009, 1010, 1012, 1016, 1020, 1021, 1022, 1023, 1024, 1025, 1026, 1027, 1028, 1029, 1031, 1032, 1033, 1035, 1036, 1037, 1038, 1042, 1043, 1045, 1046, 1047, 1053, 1057, 1059, 1060, 1062, 1063, 1064, 1065, 1066, 1067, 1070, 1072, 1073, 1075, 1077, 1078, 1082, 1083, 1085, 1089, 1090, 1091, 1093, 1095, 1097, 1099, 1102, 1104, 1105, 1107, 1111, 1113, 1116, 1117, 1120, 1121, 1125, 1126, 1129, 1131, 1135, 1136, 1137, 1138, 1139, 1140, 1142, 1143, 1144, 1145, 1146, 1147, 1148, 1149, Table 2 materials: 2, 23, 141, 185, 227, 230, 246, 248, 343, 359, 565, 631, 659, 674, 678, 679, 715, 758, 1028, 1097, Table 3 materials: 12, 19, 20, 24, 26, 27, 53, 54, 55, 59, 72, 73, 81, 84, 96, 97, 107, 111, 115, 116, 125, 133, 147, 150, 151, 154, 157, 163, 166, 169, 181, 191, 194, 198, 201, 204, 205, 213, 214, 232, 237, 239, 255, 258, 264, 270, 273, 275, 282, 283, 284, 287, 302, 306, 308, 310, 312, 314, 319, 346, 354, 355, 365, 366, 376, 379, 387, 400, 412, 419, 420, 437, 438, 439, 440, 442, 443, 447, 448, 454, 455, 469, 472, 477, 481, 492, 495, 496, 504, 509, 510, 512, 515, 517, 518, 522, 525, 526, 528, 535, 536, 538, 540, 542, 547, 549, 554, 556, 557, 575, 576, 579, 583, 585, 588, 602, 605, 617, 619, 640, 641, 645, 647, 651, 652, 662, 664, 665, 667, 672, 687, 699, 701, 703, 740, 743, 744, 745, 755, 760, 761, 777, 779, 784, 789, 796, 797, 799, 808, 810, 811, 812, 817, 819, 820, 832, 835, 836, 838, 845, 846, 847, 848, 851, 858, 875, 880, 882, 883, 888, 889, 891, 899, 900, 901, 902, 903, 904, 909, 918, 921, 931, 940, 956, 958, 960, 971, 977, 981, 983, 986, 987, 994, 995, 1001, 1002, 1004, 1005, 1011, 1017, 1018, 1019, 1030, 1039, 1040, 1041, 1051, 1052, 1054, 1055, 1058, 1061, 1069, 1071, 1074, 1076, 1079, 1081, 1084, 1088, 1098, 1110, 1112, 1115, 1118, 1119, 1122, 1127, 1128, 1133, 1134, 1141 and mixtures thereof; more preferably said malodor reduction materials are selected from the group consisting of Table 1 materials: 1, 2, 3, 4, 7, 9, 10, 11, 13, 14, 16, 17, 18, 21, 22, 23, 25, 28, 29, 30, 31, 32, 33, 34, 35, 36, 37, 38, 39, 42, 43, 47, 48, 49, 50, 52, 57, 61, 62, 63, 64, 65, 67, 68, 69, 70, 71, 74, 75, 76, 77, 78, 79, 80, 82, 83, 85, 91, 92, 93, 98, 100, 101, 102, 103, 104, 105, 106, 108, 109, 110, 112, 113, 114, 117, 119, 120, 122, 123, 126, 128, 130, 134, 135, 137, 140, 141, 142, 143, 145, 146, 148, 149, 152, 153, 155, 156, 158, 159, 161, 162, 167, 168, 170, 174, 175, 176, 177, 178, 179, 182, 183, 184, 185, 186, 187, 189, 190, 192, 193, 195, 196, 197, 199, 206, 208, 209, 210, 211, 212, 215, 218, 221, 227, 228, 229, 230, 231, 233, 234, 238, 242, 243, 244, 246, 247, 249, 252, 253, 254, 256, 259, 260, 261, 263, 267, 269, 271, 274, 276, 277, 278, 280, 281, 285, 286, 288, 289, 290, 292, 293, 294, 295, 296, 300, 301, 303, 307, 316, 317, 318, 321, 322, 323, 324, 325, 328, 329, 330, 331, 332, 333, 334, 335, 336, 338, 339, 342, 343, 344, 347, 349, 350, 352, 353, 356, 358, 359, 360, 361, 362, 363, 364, 368, 369, 370, 371, 372, 373, 374, 375, 377, 378, 381, 385, 386, 388, 390, 391, 394, 397, 398, 407, 413, 414, 415, 416, 417, 418, 421, 424, 425, 426, 428, 429, 432, 436, 441, 444, 445, 449, 450, 453, 457, 459, 461, 462, 463, 464, 465, 466, 467, 468, 470, 471, 473, 474, 475, 478, 479, 480, 482, 484, 485, 486, 487, 488, 491, 493, 497, 498, 501, 502, 503, 505, 519, 520, 521, 524, 527, 529, 530, 531, 532, 534, 537, 541, 544, 546, 548, 550, 551, 552, 553, 555, 558, 559, 560, 561, 562, 563, 565, 566, 567, 568, 569, 570, 571, 572, 573, 574, 577, 578, 580, 581, 582, 584, 586, 587, 589, 591, 592, 594, 595, 599, 600, 601, 603, 604, 606, 607, 608, 609, 610, 611, 612, 613, 614, 615, 616, 618, 620, 621, 624, 625, 626, 627, 628, 631, 632, 633, 635, 636, 638, 639, 644, 649, 650, 653, 655, 658, 659, 660, 661, 663, 668, 671, 673, 674, 675, 676, 677, 678, 679, 680, 681, 682, 683, 684, 686, 691, 692, 693, 694, 696, 697, 698, 700, 702, 704, 706, 707, 708, 709, 710, 711, 712, 713, 714, 715, 716, 717, 718, 719, 720, 721, 722, 723, 724, 725, 726, 727, 730, 731, 733, 735, 736, 738, 741, 742, 746, 748, 750, 752, 754, 757, 758, 763, 764, 766, 767, 768, 769, 770, 771, 772, 774, 775, 776, 778, 781, 782, 786, 788, 791, 792, 800, 802, 803, 804, 805, 806, 807, 814, 821, 824, 826, 827, 828, 829, 831, 833, 834, 837, 839, 840, 849, 850, 852, 856, 864, 865, 866, 868, 869, 870, 871, 872, 873, 876, 877, 878, 879, 881, 884, 885, 886, 890, 892, 893, 894, 897, 905, 908, 912, 913, 914, 916, 919, 920, 922, 923, 924, 925, 926, 927, 928, 929, 930, 933, 937, 939, 941, 942, 943, 945, 946, 947, 948, 950, 951, 953, 954, 955, 959, 962, 965, 967, 969, 973, 974, 976, 978, 980, 982, 985, 988, 993, 998, 1000, 1003, 1006, 1007, 1008, 1009, 1010, 1012, 1016, 1020, 1021, 1022, 1023, 1024, 1025, 1026, 1027, 1028, 1029, 1031, 1032, 1033, 1035, 1036, 1037, 1038, 1042, 1043, 1045, 1046, 1047, 1053, 1057, 1059, 1060, 1062, 1063, 1064, 1065, 1066, 1067, 1070, 1072, 1073, 1075, 1077, 1078, 1082, 1083, 1085, 1089, 1090, 1091, 1093, 1095, 1097, 1099, 1102, 1104, 1105, 1107, 1111, 1113, 1116, 1117, 1120, 1121, 1125, 1126, 1129, 1131, 1135, 1136, 1137, 1138, 1139, 1140, 1142, 1143, 1144, 1145, 1146, 1147, 1148, 1149, Table 2 materials: 2, 23, 141, 185, 227, 230, 246, 248, 343, 359, 565, 631, 659, 674, 678, 679, 715, 758, 1028, 1097 and mixtures thereof; more preferably said malodor reduction materials are selected from the group consisting of Table 4 materials 7, 14, 39, 48, 183, 199, 206, 212, 215, 229, 260, 261, 281, 329, 335, 353, 360, 441, 484, 487, 488, 501, 566, 567, 569, 570, 573, 574, 603, 616, 621, 624, 627, 632, 663, 680, 684, 694, 696, 708, 712, 714, 726, 750, 764, 775, 776, 788, 804, 872, 919, 927, 933, 978, 1007, 1022, 1024, 1027, 1029, 1035, 1038, 1060, 1089, 1107, 1129, 1131, 1136, 1137, 1140, 1142, 1143, 1144, 1145, 1148, 1149, Table 5 material 248 and mixtures thereof, most preferably said malodor reduction materials are selected from the group consisting of Table 4 materials 261, 680, 788, 1129, 1148, 1149 and mixtures thereof.

In one aspect of said personal care composition, said composition comprises one or more perfume raw materials.

In one aspect of said personal care composition, said sum total of malodor reduction materials has an average Log P, based on weight percent of each malodor reduction material in said sum total of malodor reduction materials, of from about 2.5 to about 8, preferably from about 3 to about 8, more preferably from about 3.5 to about 7, most preferably, each of said malodor reduction materials in said sum total of malodor reduction materials and each of said one or more perfume raw materials has a Log P from about 3.5 to about 7. This range of Log P will allow the malodor reduction material's to deposit on the skin and not wash away in the water phase during use In one aspect of said personal care composition, the ratio of said one or more perfume raw materials to said sum total of malodor reduction material being from about 1000:1 to about 1:1, preferably from about 100:1 to about 1:1, more preferably from about 10:1 to about 1:1, most preferably from about 2:1 to about 1:1.

In one aspect of said personal care composition, less than 10%, preferably less than 5%, more preferably less than 1% of said malodor reduction materials and said one or more perfume raw materials, based on total combined weight of malodor reduction materials and said one or more perfume raw materials comprise an ionone moiety.

In one aspect of said cleaning and/or treatment product, said malodor reduction materials are not selected from the group consisting of Tables 1-3 materials 302; 288; 50; 157; 1017; 888; 64; 1054; 832; 375; 390; 745; 504; 505; 140; 1012; 498; 362; 103; 356; 1074; 908; 1127; 475; 918; 687; 611; 317; 9; 141; 550; 602; 913; 1005; 521; 10; 215; 370; 335; 378; 1121; 360; 565; 1136; 1129; 655; 369; 1065; 914; 757; 601; 478; 889; 891; 358; 973; 162; 554; 522; 312; 125; 26; 418; 92; 586; 1026; 218; 31; 828; 871; 829; 1066; 287; 269; 769; 701; 1118; 70; 946; 142; 109; 108 and mixtures thereof.

In one aspect of said personal care composition, said composition comprises a total of, based on total consumer product weight, from about 0.1% to about 7% of one or more of said malodor reduction materials and from about 3% to 30% of a surfactant, and, optionally, a miscellar phase and/or lamellar phase.

In one aspect of said personal care composition, said composition comprises a total, based on total consumer product weight, of from about 0.1% to about 50% of a material selected from structurants, humectants, fatty acids, inorganic salts, antimicrobial agents, antimicrobial agents actives and mixtures thereof.

In one aspect of said personal care composition, said composition comprises an adjunct ingredient selected from the group consisting of clay mineral powders, pearl pigments, organic powders, emulsifiers, distributing agents, pharmaceutical active, topical active, preservatives, surfactants and mixtures thereof.

A method of controlling malodors comprising: contacting a situs comprising a malodor and/or a situs that will become malodorous with a personal care composition selected from the group consisting of the personal care compositions disclosed herein is disclosed.

In one aspect of said method, said situs comprises the body or head of hair and said contacting step comprises contacting said body or hair containing a malodor with a sufficient amount of Applicants' personal care composition to provide said body or hair with a level of malodor reduction material at least 0.0001 mg of malodor reduction material per body or head of hair, preferably from about 0.0001 mg of malodor reduction material per body or head of hair to about 1 mg of malodor reduction material per body or head of hair, more preferably from about 0.001 mg of malodor reduction material per body or head of hair about 0.5 mg of malodor reduction material per body or head of hair, most preferably from about 0.01 of malodor reduction material per body or head of hair to about 0.2 mg of malodor reduction material per body or head of hair.

Adjunct Materials

While not essential for the purposes of the present invention, the non-limiting list of adjuncts illustrated hereinafter are suitable for use in the instant compositions and may be desirably incorporated in certain aspects of the invention, for example to assist or enhance performance, A variety of optional ingredients can also be added to personal care compositions.

Optional ingredients can include, but are not limited to, structurants, humectants, fatty acids, inorganic salts, and other antimicrobial agents or actives.

A personal care composition can also include hydrophilic structurants such as carbohydrate structurants and gums. Some suitable carbohydrate structurants include raw starch (corn, rice, potato, wheat, and the like) and pregelatinized starch. Some suitable gums include carregeenan and xanthan gum. A personal care composition can include from about 0.1% to about 30%, from about 2% to about 25%, or from about 4% to about 20%, by weight of the personal care composition, of a carbohydrate structurant.

A personal care composition can also include one or more humectants. Examples of such humectants can include polyhydric alcohols. Further, humectants such as glycerin can be included the personal care composition as a result of production or as an additional ingredient. For example, glycerin can be a by-product after saponification of the personal care composition. Including additional humectant can result in a number of benefits such as improvement in hardness of the personal care composition, decreased water activity of the personal care composition, and reduction of a weight loss rate of the personal care composition over time due to water evaporation.

A personal care composition can include inorganic salts. Inorganic salts can help to maintain a particular water content or level of the personal care composition and improve hardness of the personal care composition. The inorganic salts can also help to bind the water in the personal care composition to prevent water loss by evaporation or other means. A personal care composition can optionally include from about 0.01% to about 15%, from about 1% to about 12%, or from about 2.5% to about 10.5%, by weight of the personal care composition, of inorganic salt. Examples of suitable inorganic salts can include magnesium nitrate, trimagnesium phosphate, calcium chloride, sodium carbonate, sodium aluminum sulfate, disodium phosphate, sodium polymetaphosphate, sodium magnesium succinate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, calcium acetate, calcium nitrate, calcium phosphate, calcium sulfate, ferric sulfate, magnesium chloride, magnesium sulfate, and tetrasodium pyrophosphate.

A personal care composition can include one or more additional antibacterial agents that can serve to further enhance antimicrobial effectiveness of the personal care composition. A personal care composition can include, for example, from about 0.001% to about 2%, from about 0.01% to about 1.5%, or from about 0.1% to about 1%, by weight of the personal care composition, of additional antibacterial agent(s). Examples of suitable antibacterial agents can include carbanilides, triclocarban (also known as trichlorocarbanilide), triclosan, a halogenated diphenylether available as DP-300 TM from Ciba-Geigy, hexachlorophene, 3,4,5-tribromosalicylanilide, and salts of 2-pyridinethiol-1-oxide, salicylic acid, and other organic acids. Other suitable antibacterial agents are described in U.S. Pat. No. 6,488,943.

Scalp Active Material

In an embodiment of the present invention, the personal care composition may comprise a scalp active material, which may be an anti-dandruff active. In an embodiment, the anti-dandruff active is selected from the group consisting of: pyridinethione salts; zinc carbonate; azoles, such as ketoconazole, econazole, and elubiol; selenium sulfide; particulate sulfur; keratolytic agents such as salicylic acid; and mixtures thereof. In a further embodiment, the anti-dandruff active may be an anti-dandruff particulate. In an embodiment, the anti-dandruff particulate is a pyridinethione salt. Such anti-dandruff particulate should be physically and chemically compatible with the components of the composition, and should not otherwise unduly impair product stability, aesthetics or performance.

Pyridinethione particulates are suitable particulate anti-dandruff actives for use in composition of the present invention. In an embodiment, the anti-dandruff active is a 1-hydroxy-2-pyridinethione salt and is in particulate form. In an embodiment, the concentration of pyridinethione anti-dandruff particulate ranges from about 0.01% to about 5%, by weight of the composition, or from about 0.1% to about 3%, or from about 0.1% to about 2%. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"; zinc pyrithione), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

In an embodiment, in addition to the anti-dandruff active selected from polyvalent metal salts of pyrithione, the composition further comprises one or more anti-fungal and/or anti-microbial actives. In an embodiment, the anti-microbial active is selected from the group consisting of: coal tar, sulfur, fcharcoal, whitfield's ointment, castellani's paint, aluminum chloride, gentian violet, octopirox (piroctone olamine), ciclopirox olamine, undecylenic acid and its metal salts, potassium permanganate, selenium sulfide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, azelaic acid, lyticase, iodopropynyl butylcarbarnate (IPBC), isothiazalinones such as octyl isothiazalinone, and azoles, and mixtures thereof. In an embodiment, the anti-microbial is selected from the group consisting of: itraconazole, ketoconazole, selenium sulfide, coal tar, and mixtures thereof.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the composition, the azole anti-microbial active is included in an amount of from about 0.01% to about 5%, or from about 0.1% to about 3%, or from about 0.3% to about 2%, by total weight of the composition. In an embodiment, the azole anti-microbial active is ketoconazole. In an embodiment, the sole anti-microbial active is ketoconazole.

The present invention may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In an embodiment, the composition comprises an effective amount of a zinc-containing layered material. In an embodiment, the composition comprises from about 0.001% to about 10%, or from about 0.01% to about 7%, or from about 0.1% to about 5% of a zinc-containing layered material, by total weight of the composition.

(A.F. Wells "Structural Inorganic Chemistry" Clarendon Press, 1975).

Many ZLMs occur naturally as minerals. In an embodiment, the ZLM is selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

(Crepaldi, EL, Sava, PC, Tronto, J, Valim, JB *J. Colloid Interfac. Sci.* 2002, 248, 429-42).

(Morioka, H., Tagaya, H., Karasu, M, Kadokawa, J, Chiba, K *Inorg. Chem.* 1999, 38, 4211-6).

In an embodiment, the composition comprises basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

Liquid Personal Care Compositions

Exemplary liquid rinse-off personal care compositions can include an aqueous carrier, which can be present at a level of from about 5% to about 95%, or from about 60% to about 85%. The aqueous carrier may comprise water, or a miscible mixture of water and organic solvent. Non-aqueous carrier materials can also be employed.

Such rinse-off personal care compositions can include one or more detersive surfactants. The detersive surfactant component can be included to provide cleaning performance to the product. The detersive surfactant component in turn comprises anionic detersive surfactant, zwitterionic or amphoteric detersive surfactant, or a combination thereof. A representative, non-limiting, list of anionic surfactants includes anionic detersive surfactants for use in the compositions can include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In one example, the anionic surfactant can be sodium lauryl sulfate or sodium laureth sulfate. The concentration of the anionic surfactant component in the product can be sufficient to provide a desired cleaning and/or lather performance, and generally ranges from about 2% to about 50%.

Amphoteric detersive surfactants suitable for use in the rinse-off personal care compositions are well known in the art, and include those surfactants broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoactetate, disodium lauroamphoacetate disodium cocodiamphoacetate, and mixtures thereof. Amphoacetates and diamphoacetates can also be used.

Zwitterionic detersive surfactants suitable for use in the rinse-off personal care compositions are well known in the art, and include those surfactants broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include betaines, including cocoamidopropyl betaine.

The liquid rinse off personal care composition can comprise one or more phases. Such personal care compositions can include a cleansing phase and/or a benefit phase (i.e., a single- or multi-phase composition). Each of a cleansing phase or a benefit phase can include various components. The cleansing phase and the benefit phase can be blended, separate, or a combination thereof. The cleansing phase and the benefit phase can also be patterned (e.g. striped).

The cleansing phase of a personal care composition can include at least one surfactant. The cleansing phase can be an aqueous structured surfactant phase and constitute from about 5% to about 20%, by weight of the personal care composition. Such a structured surfactant phase can include sodium trideceth(n) sulfate, hereinafter STnS, wherein n can define average moles of ethoxylation. n can range, for example, from about 0 to about 3; from about 0.5 to about 2.7, from about 1.1 to about 2.5, from about 1.8 to about 2.2, or n can be about 2. When n can be less than 3, STnS can provide improved stability, improved compatibility of benefit agents within the personal care compositions, and increased mildness of the personal care compositions as disclosed in U.S. Pre-Grant Publication No. 2010/009285 A1.

The cleansing phase can also comprise at least one of an amphoteric surfactant and a zwitterionic surfactant. Suitable amphoteric or zwitterionic surfactants (in addition to those cited herein) can include, for example, those described in U.S. Pat. No. 5,104,646 and U.S. Pat. No. 5,106,609.

A cleansing phase can comprise a structuring system. A structuring system can comprise, optionally, a non-ionic emulsifier, optionally, from about 0.05% to about 5%, by weight of the personal care composition, of an associative polymer; and an electrolyte.

The personal care composition can optionally be free of sodium lauryl sulfate, hereinafter SLS, and can comprise at least a 70% lamellar structure. However, the cleansing phase could comprise at least one surfactant, wherein the at least one surfactant includes SLS. Suitable examples of SLS are described in U.S. Pre-Grant Publication No. 2010/0322878 A1.

Rinse-off personal care compositions can also include a benefit phase. The benefit phase can be hydrophobic and/or anhydrous. The benefit phase can also be substantially free of surfactant. A benefit phase can also include a benefit agent. In particular, a benefit phase can comprise from about 0.1% to about 50% benefit agent by weight of the personal care composition. The benefit phase can alternatively comprise less benefit agent, for example, from about 0.5% to about 20% benefit agent, by weight of the personal care composition. Examples of suitable benefit agents can include petrolatum, glyceryl monooleate, mineral oil, natural oils, and mixtures thereof. Additional examples of benefit agents can include water insoluble or hydrophobic benefit agents. Other suitable benefit agents are described in U.S. Pre-Grant Publication No. 2012/0009285 A1.

Non-limiting examples of glycerides suitable for use as hydrophobic skin benefit agents herein can include castor oil, safflower oil, corn oil, walnut oil, peanut oil, olive oil, cod liver oil, almond oil, avocado oil, palm oil, sesame oil, vegetable oils, sunflower seed oil, soybean oil, vegetable oil derivatives, coconut oil and derivatized coconut oil, cottonseed oil and derivatized cottonseed oil, jojoba oil, cocoa butter, and combinations thereof.

Non-limiting examples of alkyl esters suitable for use as hydrophobic skin benefit agents herein can include isopropyl esters of fatty acids and long chain esters of long chain (i.e. C10-C24) fatty acids, e.g., cetyl ricinoleate, non-limiting examples of which can include isopropyl palmitate, isopropyl myristate, cetyl riconoleate, and stearyl riconoleate. Other example can include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of polyglycerin fatty acid esters suitable for use as hydrophobic skin benefit agents herein can include decaglyceryl distearate, decaglyceryl diisostearate, decaglyceryl monomyriate, decaglyceryl monolaurate, hexaglyceryl monooleate, and combinations thereof.

The rinse-off personal care composition can be applied by a variety of means, including by rubbing, wiping or dabbing with hands or fingers, or by means of an implement and/or delivery enhancement device. Non-limiting examples of implements include a sponge or sponge-tipped applicator, a mesh shower puff, a swab, a brush, a wipe (e.g., wash cloth), a loofah, and combinations thereof. Non-limiting examples of delivery enhancement devices include mechanical, electrical, ultrasonic and/or other energy devices. Employment of an implement or device can help delivery of the particulate antimicrobial agent to target regions, such as, for example, hair follicles and undulations that can exist in the underarm. The rinse-off care product can be sold together with such an implement or device. Alternatively, an implement or device can be sold separately but contain indicium to indicate usage with a rinse-off care product. Implements and delivery devices can employ replaceable portions (e.g., the skin interaction portions), which can be sold separately or sold together with the rinse-off care product in a kit.

Solid Personal Care Compositions

As noted herein, personal care compositions can take on numerous forms. One suitable form is that of a solid personal care composition. Solid compositions can take many forms like powder, pellets, bars, etc. These forms will generally be described herein as bar soap, but it should be understood that the solid composition could be in another form or shape. One example of a bar soap personal care composition can include from about 0.1% to about 35%, by weight of the personal care composition, of water, from about 45% to about 99%, by weight of the personal care composition, of soap, and from about 0.01% to about 5%, by weight of the personal care composition, of a particulate antimicrobial agent. Another suitable antimicrobial bar soap can include, for example, from about 0.1% to about 30%, by weight of the personal care composition, of water, from about 40% to about 99%, by weight of the personal care composition, of soap, and from about 0.25% to about 3%, by weight of the personal care composition, of a particulate antimicrobial agent.

Bar soap compositions can be referred to as conventional solid (i.e. non-flowing) bar soap compositions. Some bar soap composition can comprise convention soap, while others can contain synthetic surfactants, and still others can contain a mix of soap and synthetic surfactant. Bar compositions can include, for example, from about 0% to about 45% of a synthetic anionic surfactant. An example of a suitable conventional soap can include milled toilet bars that are unbuilt (i.e. include about 5% or less of a water-soluble surfactancy builder).

A personal care bar composition can include soap. By weight, the soap can be, for example, from about 45% to about 99%, or from about 50% to about 75%, by weight of the personal care composition. Such soaps can include a typical soap, i.e., an alkali metal or alkanol ammonium salt of an alkane- or alkene monocarboxylic acid. Sodium, magnesium, potassium, calcium, mono-, di- and tri-ethanol ammonium cations, or combinations thereof, can be suitable for a personal care composition. The soap included in a personal care composition can include sodium soaps or a combination of sodium soaps with from about 1% to about 25% ammonium, potassium, magnesium, calcium, or a mixture of these soaps. Additionally, the soap can be well-known alkali metal salts of alkanoic or alkenoic acids having from about 12 to about 22 carbon atoms or from about 12 to about 18 carbon atoms. Another suitable soap can be alkali metal carboxylates of alkyl or alkene hydrocarbons having from about 12 to about 22 carbon atoms. Additional suitable soap compositions are described in U.S. Pre-Grant Publication No. 2012/0219610 A1.

A personal care composition can also include soaps having a fatty acid. For example, one bar soap composition could contain from about 40% to about 95% of a soluble alkali metal soap of $C_8$-$C_{24}$ or $C_{10}$-$C_{20}$ fatty acids. The fatty acid can, for example, have a distribution of coconut oil that can provide a lower end of a broad molecular weight range or can have a fatty acid distribution of peanut or rapeseed oil, or their hydrogenated derivatives, which can provide an upper end of the broad molecular weight range. Other such compositions can include a fatty acid distribution of tallow and/or vegetable oil. The tallow can include fatty acid mixtures that can typically have an approximate carbon chain length distribution of 2.5% $C_{14}$, 29% $C_{16}$, 23% $C_{18}$, 2% palmitoleic, 41.5% oleic, and 3% linoleic. The tallow can also include other mixtures with a similar distribution, such as fatty acids derived from various animal tallows and/or lard. In one example, the tallow can also be hardened (i.e., hydrogenated) such that some or all unsaturated fatty acid moieties can be converted to saturated fatty acid moieties.

Suitable examples of vegetable oil include palm oil, coconut oil, palm kernel oil, palm oil stearine, soybean oil, and hydrogenated rice bran oil, or mixtures thereof, since such oils can be among more readily available fats. One example of a suitable coconut oil can include a proportion of fatty acids having at least 12 carbon atoms of about 85%. Such a proportion can be greater when mixtures of coconut oil and fats such as tallow, palm oil, or non-tropical nut oils or fats can be used where principle chain lengths can be $C_{16}$ and higher. The soap included in a personal care composition can be, for example, a sodium soap having a mixture of about 67-68% tallow, about 16-17% coconut oil, about 2% glycerin, and about 14% water.

Soap included in a personal care composition can also be unsaturated in accordance with commercially acceptable standards. For example, a soap included in a personal care composition can include from about 37% to about 45% unsaturated saponified material.

Soaps included in a personal care composition can be made, for example, by a classic kettle boiling process or modern continuous soap manufacturing processes wherein natural fats and oils such as tallow or coconut oil or their equivalents can be saponified with an alkali metal hydroxide using procedures well known to those skilled in the art. Soap can also be made by neutralizing fatty acids such as lauric ($C_{12}$), myristic ($C_{14}$), palmitic ($C_{16}$), or stearic ($C_{18}$) acids, with an alkali metal hydroxide or carbonate.

Soap included in a personal care composition could also be made by a continuous soap manufacturing process. The soap could be processed into soap noodles via a vacuum flash drying process. One example of a suitable soap noodle comprises about 67.2% tallow soap, about 16.8% coconut soap, about 2% glycerin, and about 14% water, by weight of the soap noodle. The soap noodles can then be utilized in a milling process to finalize a personal care composition.

Test Methods

Malodor reduction materials may be separated from mixtures, including but not limited to finished products such as consumer products and identified, by analytical methods that include GC-MS and/or NMR.

Test Method for Determining Saturation Vapour Pressure (VP)

The saturation Vapour Pressure (VP) values are computed for each PRM in the perfume mixture being tested. The VP of an individual PRM is calculated using the VP Computational Model, version 14.02 (Linux) TM available from Advanced Chemistry Development Inc. (ACD/Labs) (Toronto, Canada) to provide the VP value at 25° C. expressed in units of torr. The ACD/Labs' Vapor Pressure model is part of the ACD/Labs model suite.

Test Method for Determining the Logarithm of the Octanol/Water Partition Coefficient (log P)

The value of the log of the Octanol/Water Partition Coefficient (log P) is computed for each PRM in the perfume mixture being tested. The log P of an individual PRM is calculated using the Consensus logP Computational Model, version 14.02 (Linux) TM available from Advanced Chemistry Development Inc. (ACD/Labs) (Toronto, Canada) to provide the unitless log P value. The ACD/Labs' Consensus log P Computational Model is part of the ACD/Labs model suite.

Test Method for the Generation of Molecular Descriptors

In order to conduct the calculations involved in the computed-value test methods described herein, the starting information required includes the identity, weight percent, and molar percent of each PRM in the perfume being tested, as a proportion of that perfume, wherein all PRMs in the perfume composition are included in the calculations. Additionally for each of those PRMs, the molecular structure, and the values of various computationally-derived molecular descriptors are also required, as determined in accordance with the Test Method for the Generation of Molecular Descriptors described herein.

For each PRM in a perfume mixture or composition, its molecular structure is used to compute various molecular descriptors. The molecular structure is determined by the graphic molecular structure representations provided by the Chemical Abstract Service ("CAS"), a division of the American Chemical Society, Columbus, Ohio, U.S.A. These molecular structures may be obtained from the CAS Chemical Registry System database by looking up the index name or CAS number of each PRM. For PRMs, which at the time of their testing are not yet listed in the CAS Chemical Registry System database, other databases or information sources may be used to determine their structures. For a PRM which has potentially more than one isomer present, the molecular descriptor computations are conducted using the molecular structure of only one of the isomers, which is selected to represent that PRM. The selection of isomer is determined by the relative amount of extension in the molecular structures of the isomers. Of all the isomers of a given PRM, it is the isomer whose molecular structure that is the most prevalent which is the one that is selected to represent that PRM. The structures for other potential isomers of that PRM are excluded from the computations. The molecular structure of the isomer that is the most prevalent is paired with the concentration of that PRM, where the concentration reflects the presence of all the isomers of that PRM that are present.

A molecule editor or molecular sketching software program, such as ChemDraw TM (CambridgeSoft / PerkinElmer Inc., Waltham, Mass., U.S.A.), is used to duplicate the 2-dimensional molecular structure representing each PRM. Molecular structures should be represented as neutral species (quaternary nitrogen atoms are allowed) with no disconnected fragments (e.g., single structures with no counter ions). The winMolconn TM program described below can convert any deprotonated functional groups to the neutral form by adding the appropriate number of hydrogen atoms and will discard the counter ion.

For each PRM, the molecular sketching software is used to generate a file which describes the molecular structure of the PRM. The file(s) describing the molecular structures of the PRMs is subsequently submitted to the computer software program winMolconn TM, version 1.0.1.3 (Hall Associates Consulting, Quincy, Mass.,), in order to derive various molecular descriptors for each PRM. As such, it is the winMolconn software program which dictates the structure notations and file formats that are acceptable options. These options include either a MACCS SDF formatted file (i.e., a Structure-Data File); or a Simplified Molecular Input Line Entry Specification (i.e., a SMILES string structure line notation) which is commonly used within a simple text file, often with a ".smi" ".txt" file name extension. The SIF file represents each molecular structure in the format of a multi-line record, while the syntax for a SMILES structure is a single line of text with no white space. A structure name or identifier can be added to the SMILES string by including it on the same line following the SMILES string and separated by a space, e.g.: C1=CC=CC=C1 benzene.

The winMolconn TM software program is used to generate numerous molecular descriptors for each PRM, which are then output in a table format. Specific molecular descriptors derived by winMolconn are subsequently used as inputs (i.e., as variable terms in mathematical equations) for a variety of computer model test methods in order to calculate values such as: saturation Vapour Pressure (VP); Boiling Point (BP); logarithm of the Octanol/Water Partition Coefficient (log P); Odour Detection Threshold (ODT); Malodour Reduction Value (MORV); and/or Universal Malodour Reduction Value (Universal MORV) for each PRM. The molecular descriptor labels used in the models' test method computations are the same labels reported by the winMolconn program, and their descriptions and definitions can be found listed in the winMolconn documentation. The following is a generic description of how to execute the winMolconn software program and generate the required molecular structure descriptors for each PRM in a composition.

Computing Molecular Structure Descriptors using winMolconn:

1) Assemble the molecular structure for one or more perfume ingredients in the form of a MACCS Structure-Data File, also called an SDF file, or as a SMILES file.
2) Using version 1.0.1.3 of the winMolconn program, running on an appropriate computer, compute the full complement of molecular descriptors that are available from the program, using the SDF or SMILES file described above as input.
   a. The output of winMolconn is in the form of an ASCII text file, typically space delimited, containing the structure identifiers in the first column and respective molecular descriptors in the remaining columns for each structure in the input file.
3) Parse the text file into columns using a spreadsheet software program or some other appropriate technique. The molecular descriptor labels are found on the first row of the resulting table.
4) Find and extract the descriptor columns, identified by the molecular descriptor label, corresponding to the inputs required for each model.
   a. Note that the winMolconn molecular descriptor labels are case-sensitive.

MORV and Universal MORV Calculation

1.) Input Molecular Descriptor values as determined via the method above into the following four equations:

$$MORV = -8.5096 + 2.8597 \times (dxp9) + 1.1253 \times (knotpv) - 0.34484 \times (e1C2O2) - 0.00046231 \times (idw) + 3.3509 \times (idcbar) + 0.11158 \times (n2pag22) \quad \text{a)}$$

$$MORV = -5.2917 + 2.1741 \times (dxvp5) - 2.6595 \times (dxvp8) + 0.45297 \times (e1C2C2d) - 0.6202 \times (c1C2O2) + 1.3542 \times (CdCH2) + 0.68105 \times (CaasC) + 1.7129 \times (idcbar) \quad \text{b)}$$

$$MORV = -0.0035 + 0.8028 \times (SHCsatu) + 2.1673 \times (xvp7) - 1.3507 \times (c1C1C3d) + 0.61496 \times (c1C1O2) + 0.00403 \times (idc) - 0.23286 \times (nd2). \quad \text{c)}$$

$$MORV = -0.9926 - 0.03882 \times (SdO) + 0.1869 \times (Ssp3OH) + 2.1847 \times (xp7) + 0.34344 \times (e1C3O2) - 0.45767 \times (c1C2C3) + 0.7684 \times (CKetone) \quad \text{d)}$$

Equation a) relates a material's effectiveness in reducing the malodor trans-3-methyl-2-hexenoic acid (carboxylic acid based malodors)

Equation b) relates a material's effectiveness in reducing the malodor trimethylamine (amine based malodors)

Equation c) relates a material's effectiveness in reducing the malodor 3-mercapto-3-methylhexan-1-ol (thiol based malodors)

Equation d) relates a material's effectiveness in reducing the malodor skatole (indole based malodors)

2.) For purpose of the present application, a material's MORV is the highest MORV value from equations 1.)a) through 1.)d).

3.) If all MORVvalues from equations 1.)a) through 1.)d) above are greater than 0.5, the subject material has a Universal MORV.

Method for assigning Fragrance Fidelity Index (FFI) and the Blocker Index (BI) for a Malodor Reduction Compound Blocker materials suitable for use in consumer products of the present invention are chosen for their ability to decrease malodor, while not interfering with perception of a fragrance. Material selection is done by assigning two indices to a test sample material from two reference scales in order to rank odor strengths. The two reference scales are the Fragrance Fidelity Index (FFI) scale and the Blocker Index (BI) scale. The FFI ranks the ability of the test sample material to impart a perceivable odor which could cause interference when combined with another fragrance and the BI ranks the ability of the test sample material to reduce malodor perception. The two methods for assigning the indices to a test sample on the FFI and the BI reference scales are given below.

Method for Assigning the FFI to Test Samples

The first step in the method for assigning an FFI on the FFI reference scale is to create the FFI reference swatches. The swatches for the scale are created by treating clean fabrics swatches with a known amount of a known concentration of an ethyl vanillin solution. Fabric swatches for this test are white knit polycotton (4 inch×4 inch) swatches from EMC ordered as PC 50/50. The supplier is instructed to strip the swatches first, stripping involves washing twice with a fragrance-free detergent and rinsing three times.

Making the FFI Reference Swatches

Make three solutions of ethyl vanillin using a 50%/50% EtOH/water as the diluent at the following concentrations: 25 ppm, 120 ppm and 1000 ppm. Pipette 13 μL of each of the three solutions into the middle of a clean swatch resulting in about a 1 cm diameter of the solution in the middle of the swatch. This will create a sensory scale of three swatches with three different odor levels based on the concentration of the solution pipetted onto the swatch. After drying for 30 minutes in a vented hood, the swatches are wrapped in aluminum foil to prevent odor contamination to the treated swatch. A clean untreated swatch is also included as the lowest anchor point of reference for odor strength on the FFI scale. The FFI reference scale swatches should be used within 0.5 to 12 hours and discarded after 12 hours. The swatches are used as scale anchor points when graders evaluate a test sample(s) and are assigned a Fragrance Fidelity Index (FFI) as show in Table 7.

At least four perfumers/expert graders are used to rank the ethyl vanillin swatches in the FFI scale. The perfumer/expert grader needs to demonstrate adequate discrimination on the scale. The perfumer/expert panel is asked to rank order swatches according to a scale between 0 and 3. The panel must demonstrate statistical differences between the swatches as seen in Table 7.

TABLE 7

Results FFI of reference swatches from six perfumers/expert graders.

| FFI | Swatch | Expert Grader | | | | | | Ave | Std Dev. |
|---|---|---|---|---|---|---|---|---|---|
| | | 1 | 2 | 3 | 4 | 5 | 6 | | |
| 0 | Control: stripped swatch NIL ethyl vanillin | 0 | 0 | 0.5 | 0 | 0 | 0 | 0.08 | 0.2 |
| 1 | Stripped swatch with 13 µL 25 ppm ethyl vanillin | 0.5 | 0.5 | 0.5 | 1.5 | 0.5 | 1.0 | 0.75 | 0.4 |
| 2 | Stripped swatch with 13 µL 120 ppm ethyl vanillin | 2.0 | 1.5 | 1.5 | 2.0 | 2.0 | 2.0 | 1.8 | 0.2 |
| 3 | Stripped swatch with 13 µL 1000 ppm ethyl vanillin | 3.0 | 2.0 | 3.0 | 3.0 | 3.0 | 3.0 | 2.8 | 0.4 |

The expert graders must demonstrate a full range of 2.5 over the 4 swatches to be acceptably discriminating. Grader 2 in table 1 has a range of only 2 and is eliminated from the panel. The panel of expert graders must also demonstrated the ability to statistically discriminate between swatches in the scale.

TABLE 8

This table demonstrates acceptable expert graders with an acceptable range and the panel meets the requirement for discriminating statistics.

| FFI | Swatch | Expert Grader | | | | | Ave | Std Dev. |
|---|---|---|---|---|---|---|---|---|
| | | 1 | 3 | 4 | 5 | 6 | | |
| 0 | Control: stripped swatch NIL ethyl vanillin | 0 | 0.5 | 0 | 0 | 0 | 0.08 | 0.2 |
| 1 | Stripped swatch with 13 µL 25 ppm ethyl vanillin | 0.5 | 0.5 | 1.5 | 0.5 | 1.0 | 0.80 | 0.4 |
| 2 | Stripped swatch with 13 µL 120 ppm ethyl vanillin | 2.0 | 1.5 | 2.0 | 2.0 | 2.0 | 1.9 | 0.2 |
| 3 | Stripped swatch with 13 µL 1000 ppm ethyl vanillin | 3.0 | 3.0 | 3.0 | 3.0 | 3.0 | 3.0 | 0.0 |

The reference swatches represent the 0, 1, 2, and 3 FFIs on the FFI reference scale, Table 9. The expert grader should familiarize them self with the strength of the odor on the FFI reference swatches by sniffing each one starting at 0 (the lowest odor strength) and ending at 3 (the highest odor strength). This should be done prior to evaluating the test sample material treated swatch.

TABLE 9

Swatch treatments comprising the Fragrance Fidelity Index (FFI) reference scale

| Swatch treatment | Conc. of ethyl vanillin | FFI |
|---|---|---|
| Clean fabric swatch w/ 13 µL ethyl vanillin | 1000 ppm ethyl vanillin | 3 |
| Clean fabric swatch w/ 13 µL ethyl vanillin | 120 ppm ethyl vanillin | 2 |
| Clean fabric swatch w/ 13 µL ethyl vanillin | 25 ppm ethyl vanillin | 1 |
| Clean fabric swatch NIL ethyl vanillin | NIL ethyl vanillin | 0 |

Making Swatches Treated with the Test Material

A clean swatch is treated with 13 µL of a known concentration of a test sample material resulting in an about 1 cm of the solution on the clean swatch. Just like the reference swatches, the test sample material swatch is dried in a vented hood for 30 minutes and then wrapped in aluminum foil to prevent contamination. The test material swatches and the FFI reference swatches should be made within 2 hrs of each other. The test material swatch must be used within 0.5 to 12 hours and discarded after 12 hours.

Assigning the FFI to the Test Material

At least two perfumers/expert graders are used to assign an FFI grade to a test sample. The perfumer/expert grader smells the test sample swatch by holding that swatch 1 inch from their nose with their nose centered over the area where the test sample was pipetted on to the fabric and then assigns the test sample an FFI grade using the FFI reference scale anchor swatches as references. The test sample swatch is assigned an FFI grade at or between numbers on the FFI scale shown in Table 9. In cases where the test sample material is graded greater than 3, the test material is not a blocker material or the concentration of the material needs to be lowered and reevaluated to determine if a lower level has a malodor blocker functionality.

Method for Assigning the BI to Test Sample

The first step in the method for assigning a BI to a test sample material on the BI reference scale is to create the BI reference swatches. The swatches for the scale are created by treating clean fabrics swatches with a known amount of a known volume of isovaleric acid solution at a known concentration. Fabric swatches for this test are white knit polycotton (4 inch×4 inch) swatches from EMC ordered as PC 50/50. The supplier is instructed to strip the swatches first, stripping involves washing twice with a fragrance-free detergent and rinsing three times.

Making the BI Reference Swatches

Make one solution of 0.08% isovaleric acid using 50%/50% EtOH/water as the diluent. The BI scale contains one clean swatch with no malodor applied. Three other swatches each have a different volume of the 0.08% isovaleric acid applied. Pipette 2 µL of the 0.08% isovaleric acid solution to one clean swatch, 5 µL of the 0.08% isovaleric acid solution to the next swatch and 20 µL of isovaleric acid to the final clean swatch. These solutions are pipetted to the middle of the swatches. This will create a sensory scale of three swatches with three different odor levels based on the volume of the 0.08% isovaleric acid solution pipetted onto the swatch. After drying for 30 minutes in a vented hood, the swatches are wrapped in aluminum foil to prevent odor contamination to the treated swatch. A clean untreated swatch is also included as the lowest anchor point of reference for malodor strength on the BI scale. The BI reference scale swatches should be used within 0.5 to 12 hours and discarded after 12 hours. The swatches are used as scale anchor points when graders evaluate a test sample(s) and are assigned a Blocker Index (BI) as show in Table 12.

At least four perfumers/expert graders are used to rank the isovaleric acid swatches in the BI scale. The perfumer/expert grader needs to demonstrate adequate discrimination on the scale. The perfumer/expert grader is asked to rank order swatches according to a scale between 0 and 3. The panel of graders must demonstrate statistical differences between the swatches as seen in Table 10.

TABLE 10

Results from six perfumers/expert graders to create the BI scale.

|    |                                             | Expert Grader |     |     |     |     |     | Std  |
|----|---------------------------------------------|---------------|-----|-----|-----|-----|-----|------|
| BI | Swatch                                      | 1             | 2   | 3   | 4   | 5   | Ave | Dev. |
| 0  | Control: stripped swatch NIL isovaleric acid | 0             | 0   | 0   | 0   | 0   | 0   | 0    |
| 1  | Stripped swatch with 2 µL 0.08% isovaleric acid | 0.5       | 2.0 | 1.0 | 1.0 | 0.5 | 1.0 | 0.5  |
| 2  | Stripped swatch with 5 µL 0.08% isovaleric acid | 2.0       | 2.5 | 2.0 | 2.0 | 2.0 | 2.1 | 0.2  |
| 3  | Stripped swatch with 20 µL 0.08% isovaleric acid | 3.0      | 3.0 | 3.0 | 3.0 | 2.5 | 2.8 | 0.2  |

The expert graders must demonstrate a full range of 2.5 over the 4 swatches to be acceptably discriminating. The panel of expert graders must also demonstrated the ability to statistically discriminate between swatches in the scale. Expert grader #2 did not demonstrate the ability to discriminate between the swatches and is eliminated from the panel, see Table 11.

TABLE 11

This table demonstrates acceptable expert graders with an acceptable range and the panel meets the requirement for discriminating statistics.

|    |                                             | Expert Grader |     |     |     |     | Std  |
|----|---------------------------------------------|---------------|-----|-----|-----|-----|------|
| BI | Swatch                                      | 1             | 3   | 4   | 5   | Ave | Dev. |
| 0  | Control: stripped swatch NIL isovaleric acid | 0            | 0   | 0   | 0   | 0   | 0    |
| 1  | Stripped swatch with 2 µL 0.08% isovaleric acid | 0.5      | 1.0 | 1.0 | 0.5 | 0.8 | 0.3  |
| 2  | Stripped swatch with 5 µL 0.08% isovaleric acid | 2.0      | 2.0 | 2.0 | 2.0 | 2.0 | 0    |
| 3  | Stripped swatch with 20 µL 0.08% isovaleric acid | 3.0     | 3.0 | 3.0 | 2.5 | 2.9 | 0.2  |

The reference swatches represent the 0, 1, 2, and 3 BIs on the BI reference scale, Table 12. The expert grader should familiarizes him/herself with the strength of the odor on the BI reference swatches by sniffing each one starting at 0 (the lowest odor strength) and ending at 3 (the highest odor strength). This should be done prior to evaluating the swatch treated with the test material.

TABLE 12

Swatch treatments comprising the Blocker Index (BI) reference scale.

| Swatch/treatment | Wt of isovaleric acid | BI |
|---|---|---|
| Clean fabric swatch w/ 20 µL 0.08% isovaleric acid | 16 mg isovaleric acid | 3 |
| Clean fabric swatch w/ 5 µL 0.08% isovaleric acid | 4 mg isovaleric acid | 2 |
| Clean fabric swatch w/ 2 µL 0.08% isovaleric acid | 1.6 mg isovaleric acid | 1 |
| Clean fabric swatch NIL isovaleric acid | NIL isovaleric acid | 0 |

Making the Malodorous Swatch and Treating it with a Test Material

To evaluate the BI, the test material is applied to a malodorous swatch to determine how well the test material blocks the malodor. The malodorous swatch is made by treating a clean swatch with 20 µL of a 0.08% solution of isovaleric acid. Dry the malodorous swatch treated with isovaleric acid in a vented hood for 30 minutes. After drying the malodorous swatch a known concentration of test material solution, between 1 ppm and 100 ppm is pipetted onto the malodorous swatch. Apply the test material solution right on top of the spot where the isovaleric acid solution was applied making an about 1 cm diameter spot. Just like the BI reference swatches, the isovaleric acid+test material swatch is dried in a vented hood for 30 minutes and then wrapped in aluminum foil to prevent contamination. The isovaleric acid+test material swatches and the BI reference swatches should be made within 2 hrs of each other. The isovaleric acid+test material swatch must be used between 1-12 hours just like the reference swatches. It is sometimes necessary to evaluate several levels of the test material between about 1 and about 100 ppm to determine the BI.

Assigning the BI to the Test Material

At least two perfumers/expert graders are used to assign the BI to the test sample. The expert grader smells the isovaleric acid+test material swatch by holding that swatch one inch from their nose with their nose centered over the area where the Test sample was pipetted on to the fabric and then assigns the isovaleric acid+test material swatch a BI based on ranking its odor strength against the odor strength of the swatches in the BI reference scale. The test sample swatch is assigned a BI at or between numbers on the BI in table. In cases where the isovaleric acid+test material swatch odor is greater than 3 on the BI reference scale, this indicates the material is not a blocker or the concentration of the test material needs to be lowered to achieve its blocker functionality.

| Malodor Reduction Compounds with FFI and BI Grades based on the aforementioned | | | | | |
|---|---|---|---|---|---|
| Table Ref # | CAS# | log P | Name | Conc | FFI | BI |
| 281 | 54830-99-8 | 3.11 | 3a,4,5,6,7,7a-hexahydro-4,7-methano-1H-indenyl acetate | 10 ppm | 0 | 2.0 |
|  |  |  |  | 50 ppm | 0.5 | 2.0 |

Malodor Reduction Compounds with FFI and
BI Grades based on the aforementioned

| Table Ref # | CAS# | log P | Name | Conc | FFI | BI |
|---|---|---|---|---|---|---|
| 677 | 139504-68-0 | 3.75 | 1-((2-(tert-butyl)cyclohexyl)oxy)butan-2-ol | 10 ppm | 0 | 2.3 |
|  |  |  |  | 50 ppm | 1.8 | 2.0 |
| 962 | 55066-48-3 | 3.17 | 3-methyl-5-phenylpentan-1-ol | 10 ppm | 0 | 2.3 |
|  |  |  |  | 50 ppm | 0.5 | 1.7 |
| 261 | 173445-65-3 | 3.29 | 3-(3,3-dimethyl-2,3-dihydro-1H-inden-5-yl)propanal | 10 ppm | 0 | 1.8 |
|  |  |  |  | 50 ppm | 1.3 | 1.3 |
| 1139 | 87731-18-8 | 2.11 | (Z)-cyclooct-4-en-1-yl methyl carbonate | 10 ppm | 0 | 2.0 |
|  |  |  |  | 50 ppm | 1.0 | 2.7 |
|  | 4430-31-3 | 1.43 | 3,4,4a,5,6,7,8,8a-octahydrochromen-2-one | 10 ppm | 0 | 2.0 |
|  |  |  |  | 50 ppm | 0 | 2.0 |
| 204 | 40379-24-6 | 3.89 | 7-methyloctyl acetate | 10 ppm | 0 | 2.0 |
|  |  |  |  | 50 ppm | 0 | 2.7 |
| 1005 | 93981-50-1 | 5.59 | ethyl (2,3,6-trimethylcyclohexyl) carbonate | 50 ppm | 0.5 | 2.6 |
| 391 | 106-33-2 | 5.73 | Ethyl laurate | 50 ppm | 0.3 | 2.2 |
| 1148 | 1139-30-6 | 4.06 | Caryophyllene Oxide | 50 ppm | 0.5 | 2.3 |
| 524 | 13877-91-3 3338-55-4 | 4.31 | 3,7-Dimethyl-1,3,6-Octatriene(cis-β ocimene 70%) | 50 ppm | 0 | 2.8 |
| 1149 | 23787-90-8 | 4 | 1,3,4,6,7,8alpha-hexahydro-1,1,5,5-tetramethyl-2H-2,4alpha-methanophtalen-8(5H)-one | 10 ppm | 0 | 1.5 |
|  |  |  |  | 50 ppm | 0.8 | 2.3 |
|  | 112-42-5 | 4.62 | Undecanol | 50 ppm | 0.8 | 2.3 |
| 174 | 112-53-8 | 5.17 | 1-dodecanol | 50 ppm | 0.5 | 2.3 |
|  | 98-52-2 | 2.78 | 4-tert-butyl cyclohexane | 10 ppm | 0 | 2.0 |
|  |  |  |  | 50 ppm | 0.3 | 2.0 |
| 109 | 112-39-0 | 6.41 | Methyl palmitate | 10 ppm |  | 2.0 |

Malodor Control Compounds with Improved Performance at Lower Levels.

Below are some non-limiting examples of preferred behavior by which the malodor control compound gives improved malodor control at lower concentration. These nonlimiting data provide additional compelling data that malodor is being blocked, not masked.

| Table Ref # | CAS# | Name | Conc | FFI | BI |
|---|---|---|---|---|---|
| N/A | 68912-13-0 | 8,8-dimethyl-3a,4,5,6,7,7a-hexahydro-1H-4,7-methanoinden-6-yl propionate | 10 ppm | 0 | 1.5 |
|  |  |  | 50 ppm | 0 | 2.2 |
| N/A | TBD | 4,8-dimethyl-1-(methylethyl)-7-oxybiciclo [4.3.0]nonane | 10 ppm |  | 2.0 |
|  |  |  | 50 ppm | 0.3 | 2.2 | about 0.001 Fragrance Fidelity

Retesting Malodor Reduction Compounds at Lower Levels.

The example below demonstrates that while a malodor control compound could fail to demonstrate odor blocking (BI >2.5) at a higher concentration it should be retested at a lower concentration to determine if it passes.

| Table Ref # | CAS # | Name | Conc | FFI | BI |
|---|---|---|---|---|---|
| N/A | 173445-65-3 | 1H-Indene-5-propanal, 2,3-dihydro-3,3-dimethyl- | 10 ppm | 0 | 1.5 |
|  |  |  | 50 ppm | 0.5 | 2.7 |

Example 1

Compositions Comprising Malodor Reduction Compounds

In the present invention blends enable more potent malodor reduction because blends are useful at a higher % of the product composition before becoming olfactively noticeable. Below are non-limiting examples of malodor reduction compounds.

| Component | CAS# | % wt Active | | | | |
|---|---|---|---|---|---|---|
|  |  | A | B | C | D | E |
| 2,2,8,8-tetramethyl-octahydro-1H-2,4a-methanonapthalene-10-one | 29461-14-1 | 35-45 | 15-25 | 5-20 | 10-30 | 15-25 |
| 1H-Indene-ar-propanal, 2,3-dihydro-1,1-dimethyl- | 300371-33-9 | 10-20 | 1-30 | NIL | 5-10 | 1-5 |
| Hexadecanoic acid, (2E)-3,7-dimethyl-2,6-octadien-1-yl ester | 3681-73-0 | 35-45 | 10-25 | NIL | 30-40 | 35-50 |
| 1-Pentanol-3-methyl-5-phenyl | 55066-48-3 | 10-20 | 10-25 | 2-10 | 5-17 | 10 |
| 4,7-Methano-1H-inden-5-ol, 3a,4,5,6,7,7a-hexahydro-, 5-acetate | 171102-41-3 | 0-5 | 10-25 | NIL | 1-6 | 1-5 |
| 4,8-dimethyl-1-(methylethyl)-7-oxybiciclo [4.3.0]nonane | N/A | 0-5 | NIL | NIL | NIL | 1-5 |

-continued

| Component | CAS# | % wt Active |||||
|---|---|---|---|---|---|---|
| | | A | B | C | D | E |
| (3Z)-3,7-dimethylocta-1,3,6-triene | 3338-55-4 | NIL | NIL | 10-20 | 2-5 | NIL |
| 1H-Indene-5-propanal, 2,3-dihydro-3,3-dimethyl- | 173445-65-3 | NIL | NIL | NIL | 7.5-16 | 1-15 |
| 3,4,4a,5,6,7,8,8a-octahydrochromen-2-one | 4430-31-3 | NIL | NIL | NIL | 3-7 | 1-15 |
| 1-(2-tert-butylcyclohexyl)oxybutan-2-ol | 139504-68-0 | NIL | NIL | NIL | 0.25-1.5 | NIL |
| ethyl (2,3,6-trimethylcyclohexyl) carbonate | 93981-50-1 | NIL | NIL | 15-30 | NIL | 2 |
| benzyl 2-hydroxypropanoate | 2051-96-9 | NIL | NIL | 2-5 | NIL | NIL |
| (3,5-dimethylcyclohex-3-en-1-yl)methanol | 67634-16-6 | NIL | NIL | 5-30 | NIL | NIL |
| 2-Dodecanol | 10203-28-8 | NIL | 0.25-1 | NIL | 0.5-3 | NIL |

Example 2

Compositions Comprising Malodor Reduction Compounds

| Ingredient | CAS # | % wt Active ||||||
|---|---|---|---|---|---|---|---|
| | | A | B | C | B | D | E |
| (E)-1-(2,6,6-trimethyl-1-cyclohex-2-enyl)pent-1-en-3-one | 127-42-4 | 4 | 8 | 2 | 8 | 3 | 2 |
| ethyl dodecanoate | 106-33-2 | NIL | 1 | NIL | 3 | NIL | NIL |
| 3a,4,5,6,7,7a-hexahydro-1H-4,7-methanoinden-1-yl propanoate | 68912-13-0 | 8 | 30 | 1 | 4 | 1 | 3.5 |
| [1R-(1R*,4R*,6R*,10S*)]-4,12,12-trimethyl-9-methylene-5-oxatricyclo[8.2.0.04,6]dodecane | 1139-30-6 | NIL | 0.3 | 2 | 0.5 | NIL | 0.5 |
| (8E)-cyclohexadec-8-en-1-one | 3100-36-5 | NIL | 5 | NIL | 7 | NIL | NIL |
| 3,5,5-trimethylhexyl acetate | 58430-94-7 | 25 | 15 | 50 | 35 | 60 | 56 |
| ethyl (2,3,6-trimethylcyclohexyl) carbonate | 93981-50-1 | NIL | 1 | NIL | 5 | NIL | NIL |
| 2,4-dimethyl-4,4a,5,9b-tetrahydroindeno[1,2-d][1,3]dioxine | 27606-09-3 | 25 | 10 | 15 | 15 | 16 | 15 |
| 2,2,7,7-tetramethyltricyclo[6.2.1.01,6]undecan-5-one | 23787-90-8 | 8 | 9 | 5 | 7 | 5 | 5 |
| (3,5-dimethylcyclohex-3-en-1-yl)methanol | 67634-16-6 | NIL | 0.7 | NIL | 0.5 | NIL | NIL |
| 3-(7,7-dimethyl-4-bicyclo[3.1.1]hept-3-enyl)-2,2-dimethylpropanal | 33885-52-8 | 30 | 20 | 25 | 15 | 15 | 18 |
| Total | | 100 | 100 | 100 | 100 | 100 | 100 |

Example 3

Malodor Reduction Composition

| Ingredient | CAS # | % wt Active |||
|---|---|---|---|---|
| | | A | B | C |
| 5-Cyclohexadecen-1-One | 37609-25-9 | 15.0 | 2.00 | 2.00 |
| decahydro-2,2,7,7,8,9,9-heptamethylindeno(4,3a-b)furan | 476332-65-7 | 0.005 | 0.01 | 0.01 |
| 2,3-Dihydro-5,6-dimethoxy-2-(4-piperidinylmethylene)-1H-inden-1-one | 33704-61-9 | 0.3 | 0.5 | 0.5 |
| Cedryl Methyl Ether | 19870-74-7 | 6.0 | 10.0 | 4.0 |
| Trans-4-Decenal | 65405-70-1 | 0.005 | 0.002 | 0.002 |

-continued

| Ingredient | CAS # | % wt Active A | B | C |
|---|---|---|---|---|
| Decyl Aldehyde | 112-31-2 | 3.74 | 2.0 | 2.0 |
| 3-methyl cyclopentadecenone | 63314-79-4 | 0.4 | 1.0 | 1.0 |
| Diphenyl Oxide | 101-84-8 | 0.5 | 1.0 | 1.0 |
| 3a,4,5,6,7,7a-hexahydro-4,7-methano-1H-indenyl acetate | 54830-99-8 | 5.0 | 8.0 | 8.0 |
| 3a,4,5,6,7,7a-hexahydro-1H-4,7-methanoinden-1-yl propanoate | 68912-13-0 | 6.0 | 8.0 | 8.0 |
| 2-(5-methyl-2-propan-2-yl-8-bicyclo[2.2.2]oct-5-enyl)-1,3-dioxolane | 68901-32-6 | 10.0 | 15.0 | 15.0 |
| (E)-3,7-dimethyl-2,6-octadienylhexadecanoate | 3681-73-0 | 10.0 | 10.0 | 16.0 |
| Iso Nonyl Acetate | 58430-94-7 | 6.65 | 8.0 | 3.0 |
| 2,2,7,7-tetramethyltricyclo[6.2.1.01,6]undecan-5-one | 23787-90-8 | 10.0 | 8.0 | 8.0 |
| (1-Methyl-2-(1,2,2-trimethylbicyclo[3.1.0]-hex-3-ylmethyl)cyclopropyl)methanol | 198404-98-7 | 0.1 | 0.3 | 0.3 |
| Lauric Aldehyde | 112-54-9 | 0.625 | 1.0 | 0.7 |
| Methyl Iso Eugenol | 93-16-3 | 18.000 | 10.0 | 13.0 |
| Methyl hexadecanoate | 112-39-00 | 3.000 | 10.0 | 12.0 |
| 2,3-dihydro-1,1-1H-dimethyl-indene-ar-propanal | 300371-33-9 | 0.400 | 0.0 | 0.3 |
| 4-tert-butylcyclohexanol | 98-52-2 | 0.400 | 0.1 | 0.1 |
| 2-isobutyl-4-hydroxy-4-methyltetrahydropyran | 63500-71-0 | 1.600 | 2.0 | 2.0 |
| Undecyl Aldehyde | 112-44-7 | 1.725 | 2.888 | 1.888 |
| Undecylenic Aldehyde | 112-45-8 | 0.550 | 0.2 | 1.2 |
| Total | | 100 | 100.0 | 100.0 |

Examples 4.1-4.3

Body Wash with Malodor Reducing Composition

An example of Body Wash compositions prepared with malodor reduction composition, according to the compositions shown in Example 1.

| | 4.1 Body Wash | 4.2 Body Wash | 4.3 BodyWash |
|---|---|---|---|
| Sodium Laureth-3 Sulfate (as 28% active) | 27.85% | 27.85% | 27.85% |
| Water | Q.S. | Q.S. | Q.S. |
| Sodium Lauryl Sulfate (as 29% active) | 10.34 | 10.34 | 10.34 |
| Cocamidopropyl Betaine B (30% active) | 4.01 | 4.01 | 4.01 |
| Citric Acid | 0.18 | 0.18 | 0.18 |
| Sodium Benzoate | 0.3 | 0.3 | 0.3 |
| Disodium EDTA | 0.12 | 0.12 | 0.12 |
| Methylchloroisothiazolinone/Methylisothiazolinone | 0.04 | 0.04 | 0.04 |
| Sodium Chloride | 2.35 | 1.7 | 1.6 |
| Neat Perfume | 1.25 | 1 | 2 |
| Malodor reducing composition | 0.25 | 0.175 | 0.25 |

QS - indicates that this material is used to bring the total to 100%

Examples 5.1-5.6

Shampoo with Malodor Reducing Composition

An example of Shampoo compositions prepared with malodor reduction composition, according to the compositions shown in Example 1.

| Ingredient | 5.1 | 5.2 | 5.3 |
|---|---|---|---|
| | Wt % | | |
| Ammonium Laureth Sulfate[1] | 14.1 | 14.1 | 14.1 |
| Ammonium Lauryl Sulfate[2] | 3.1 | 3.1 | 3.1 |
| Ammonium Xylenesulfonate[3] | 0.45 | 0.45 | 0.45 |
| TWEEN 60[4] | 3.0 | 3.0 | 3.0 |
| Polyquaternium-10[5] | 0.35 | 0.35 | 0.35 |
| Cetrimonium Chloride[6] | 0.5 | 0.5 | 0.5 |
| Selenium Sulfide[7] | 1.0 | 1.0 | 1.0 |
| Dimethicone[8] | 0.60 | 0.60 | 0.60 |
| Ethylene Glycol Distearate[9] | 3.0 | 3.0 | 3.0 |
| Cocamide MEA[10] | 3.0 | 3.0 | 3.0 |
| Zinc Pyrithione[11] | — | 0.2 | 0.2 |
| Zinc Carbonate[12] | — | — | 1.61 |
| Neat Fragrance | 1.1 | 0.75 | 0.75 |
| Malodor reducing composition | 0.25 | 0.25 | 0.175 |
| Cetyl Alcohol[13] | 0.42 | 0.42 | 0.42 |
| DMDM Hydantoin | 0.40 | 0.40 | 0.40 |
| Sodium Chloride | 0.30 | 0.30 | 0.30 |
| Stearyl Alcohol[14] | 0.20 | 0.20 | 0.20 |
| Hydroxypropyl Methylcellulose[15] | 0.02 | 0.02 | 0.02 |
| Water | Q.S. | Q.S. | Q.S. |

[1]Ammonium Laureth Sulfate at 25% active, supplier: P&G
[2]Ammonium Lauryl Sulfate at 25% active, supplier: P&G
[3]Ammonium Xylene Sulfonate 40% active, supplier: Stepan
[4]Polysorbate 60 TM, supplier: Croda
[5]UCARE Polymer LR400 TM, supplier - Dow Chemical
[6]cetrimonium chloride, supplier - Croda
[7]Selenium disulfide, supplier Eskay
[8]Viscasil 330M TM from Momentive Performance Materials with a viscosity of 330,000 cSt (centistokes).
[9]Ethylene Glycol Disterate, supplier: Stepan
[10]Ninol COMF TM from the Stepan Company
[11]Zinc Pyrithione, supplier Lonza
[12]Zinc Carbonate Basic, supplier Pan Continental Chemical
[13]Cetyl Alcohol, supplier P&G
[14]Stearyl Alcohol, supplier P&G
[15]Methocel TM, supplier Dow Chemical

| Ingredients | 5.4 | 5.5 Wt % | 5.6 |
|---|---|---|---|
| Ammonium Laureth Sulfate[1] | 14.1 | 14.1 | 14.1 |
| Ammonium Lauryl Sulfate[2] | 3.1 | 3.1 | 3.1 |
| Ammonium Xylenesulfonate[3] | 0.45 | 0.45 | 0.45 |
| TWEEN 60[4] | 3.0 | 3.0 | 3.0 |
| Polyquaternium-10[5] | 0.35 | 0.35 | 0.35 |
| Cetrimonium Chloride[6] | 0.5 | 0.5 | 0.5 |
| Selenium Sulfide[7] | 1.0 | 0.2 | 0.2 |
| Dimethicone[8] | 0.60 | 0.60 | 0.60 |
| Ethylene Glycol Distearate[9] | 3.0 | 3.0 | 3.0 |
| Cocamide MEA[10] | 3.0 | 3.0 | 3.0 |
| Zinc Pyrithione[11] | — | 1.0 | 1.0 |
| Zinc Carbonate[12] | — | — | 1.61 |
| Neat Fragrance | 0.65 | 0.85 | 1.0 |
| Malodor reducing composition | 0.175 | 0.175 | 0.175 |
| Cetyl Alcohol[13] | 0.42 | 0.42 | 0.42 |
| DMDM Hydantoin | 0.40 | 0.40 | 0.40 |
| Sodium Chloride | 0.30 | 0.30 | 0.30 |
| Stearyl Alcohol[14] | 0.20 | 0.20 | 0.20 |
| Hydroxypropyl Methylcellulose[15] | 0.02 | 0.02 | 0.02 |
| Water | Q.S. | Q.S. | Q.S. |

[1]Ammonium Laureth Sulfate at 25% active, supplier: P&G
[2]Ammonium Lauryl Sulfate at 25% active, supplier: P&G
[3]Ammonium Xylene Sulfonate 40% active, supplier: Stepan
[4]Polysorbate 60 TM, supplier: Croda
[5]UCARE Polymer LR400 UTM, supplier - Dow Chemical
[6]cetrimonium chloride, supplier - Croda
[7]Selenium disulfide, supplier Eskay
[8]Viscasil 330M TM from Momentive Performance Materials with a viscosity of 330,000 cSt (centistokes).
[9]Ethylene Glycol Disterate, supplier: Stepan
[10]Ninol COMF TM from the Stepan Company
[11]Zinc Pyrithione, supplier Lonza
[12]Zinc Carbonate Basic, supplier Pan Continental Chemical
[13]Cetyl Alcohol, supplier P&G
[14]Stearyl Alcohol, supplier P&G
[15]Methocel TM, supplier Dow Chemical In an embodiment of the present invention, the example of Shampoo compositions (Example 5) may also be prepared with the malodor reduction composition according to the compositions shown in Example 2 and/or Example 3.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed:

1. A liquid rinse-off personal care composition comprising, based on total composition weight,
    a) from about 0.001% to about 0.025%, by weight of the composition of a malodor reduction material comprising 1, 3, 4, 6, 7, 8 alpha-hexahydro-1, 1, 5, 5-tetramethyl-2H-2, 4 alpha-methanophthalen-8(5H)-one; and
    b) from about 0% to about 12% of a perfume;
    c) from about 60% to about 95% of an aqueous carrier; and
    d) from about 3% to about 30% of a surfactant.

2. The personal care composition according to claim 1, wherein the ratio by weight of said perfume to said malodor reduction material being from about 1000:1 to about 1:1.

3. The personal care composition according to claim 1, said composition comprising an adjunct ingredient selected from the group consisting of clay mineral powders, pearl pigments, organic powders, emulsifiers, distributing agents, pharmaceutical active, topical active, preservatives, surfactants and mixtures thereof.

4. The personal care composition according to claim 1, comprising from about 0.001% to about 0.005%, by weight of the composition of the 1, 3, 4, 6, 7, 8 alpha-hexahydro-1, 1, 5, 5-tetramethyl-2H-2, 4 alpha-methanophthalen -8(5H)-one.

* * * * *